(12) United States Patent
Danek et al.

(10) Patent No.: US 12,011,535 B2
(45) Date of Patent: Jun. 18, 2024

(54) ELECTRONIC DEVICES AND LIQUIDS FOR AEROSOLIZING AND INHALING THEREWITH

(71) Applicant: QNOVIA, INC., Richmond, VA (US)

(72) Inventors: Mario Danek, Los Angeles, CA (US); Ian Kovacevich, Carlsbad, CA (US); Andrew Heinrich, Denair, CA (US); Christopher Kar-Heng Cheng, Los Angeles, CA (US); Joseph Gene Walsh, Los Angeles, CA (US)

(73) Assignee: QNOVIA, INC., Richmond, VA (US)

( * ) Notice: Subject to any disclaimer, the term of this patent is extended or adjusted under 35 U.S.C. 154(b) by 0 days.

(21) Appl. No.: 18/072,656

(22) Filed: Nov. 30, 2022

(65) Prior Publication Data

US 2023/0121005 A1 Apr. 20, 2023

Related U.S. Application Data

(63) Continuation of application No. 17/075,679, filed on Oct. 20, 2020.

(Continued)

(51) Int. Cl.
*A24F 40/10* (2020.01)
*A24B 15/167* (2020.01)
(Continued)

(52) U.S. Cl.
CPC .......... *A61M 11/003* (2014.02); *A24B 15/167* (2016.11); *A24F 40/05* (2020.01);
(Continued)

(58) Field of Classification Search
CPC .......... A24F 40/05; A24F 40/10; A24F 40/42; A24F 40/48; A24B 15/167; A24B 15/283;
(Continued)

(56) References Cited

U.S. PATENT DOCUMENTS 6,138,669 A  10/2000  Rocci, Jr. et al.
6,915,962 B2  7/2005  Power et al.
(Continued)

FOREIGN PATENT DOCUMENTS

CN  106714974 A  5/2017
EP  0002234 A1  6/1979
(Continued)

OTHER PUBLICATIONS

"Innokin Adept: Unboxing Experience" (Kai's Virgin Vapor), Jul. 27, 2021, retrieved from https://web.archive.org/web/20210727211502/https://www.kaisvirginvapor.com/pages/innokin-adept-unboxing-experience.

(Continued)

*Primary Examiner* — Abdullah A Riyami
*Assistant Examiner* — Thang H Nguyen
(74) *Attorney, Agent, or Firm* — TILLMAN WRIGHT, PLLC; Chad D. Tillman

(57) ABSTRACT

An electronic device includes a mouthpiece, a bladder, and a mesh assembly having a mesh material and a piezoelectric material. The mesh material is in contact with a liquid of the bladder. The mouthpiece, the bladder, and the mesh assembly are located in-line along a longitudinal axis of the device between opposite longitudinal ends of the device, with the mesh assembly extending between and separating the mouthpiece and the bladder. A liquid-filled cartridge also is disclosed for use with an electronic device for delivery of a substance into a body through respiration includes a liquid container; and a liquid contained within the container for aerosolizing and inhaling by a person using the electronic device. The liquid includes a plurality of nanoparticles in a nanoemulsion, the nanoparticles including the encapsulation of the substance to be delivered into the body through (Continued)

respiration. The nanoemulsion preferably is produced using a microfluidizing machine.

17 Claims, 35 Drawing Sheets

Related U.S. Application Data

(60) Provisional application No. 62/924,171, filed on Oct. 21, 2019, provisional application No. 62/924,168, filed on Oct. 21, 2019, provisional application No. 62/923,563, filed on Oct. 20, 2019, provisional application No. 62/923,602, filed on Oct. 20, 2019, provisional application No. 62/923,604, filed on Oct. 20, 2019.

(51) Int. Cl.
*A24F 40/05* (2020.01)
*A24F 40/42* (2020.01)
*A61K 9/00* (2006.01)
*A61K 9/107* (2006.01)
*A61K 9/127* (2006.01)
*A61K 31/00* (2006.01)
*A61K 31/05* (2006.01)
*A61K 31/352* (2006.01)
*A61K 31/4439* (2006.01)
*A61K 31/465* (2006.01)
*A61K 47/02* (2006.01)
*A61K 47/26* (2006.01)
*A61M 11/00* (2006.01)
*B05B 17/06* (2006.01)

(52) U.S. Cl.
CPC .............. *A24F 40/10* (2020.01); *A24F 40/42* (2020.01); *A61K 9/0078* (2013.01); *A61K 9/1075* (2013.01); *A61K 9/127* (2013.01); *A61K 31/05* (2013.01); *A61K 31/352* (2013.01); *A61K 31/4439* (2013.01); *A61K 31/465* (2013.01); *A61K 31/658* (2023.05); *A61K 47/02* (2013.01); *A61K 47/26* (2013.01); *B05B 17/0653* (2013.01); *A61M 2205/0294* (2013.01); *A61M 2205/12* (2013.01); *A61M 2205/587* (2013.01); *A61M 2205/8206* (2013.01)

(58) Field of Classification Search
CPC .. A61K 31/05; A61K 31/352; A61K 31/4439; A61K 47/02; A61K 47/26; A61K 9/0078; A61K 9/1075; A61K 9/127; A61M 11/001; A61M 11/003; A61M 11/005; A61M 15/0085; A61M 15/06; A61M 2202/0007; A61M 2202/0468; A61M 2205/0294; A61M 2205/12; A61M 2205/583; A61M 2205/587; A61M 2205/8206; B05B 17/0646; B05B 17/0653; B05B 17/0676; B05B 9/047
See application file for complete search history.

(56) References Cited

U.S. PATENT DOCUMENTS

| | | | |
|---|---|---|---|
| 7,013,894 B2 | 3/2006 | McFarland |
| 7,243,648 B2 | 7/2007 | Yang et al. |
| 7,380,729 B2 | 6/2008 | Wendt et al. |
| 7,387,265 B2 | 6/2008 | Hess et al. |
| 7,458,372 B2 | 12/2008 | Feiner et al. |
| 7,470,547 B2 | 12/2008 | Tisone et al. |
| 7,712,466 B2 | 5/2010 | Addington |
| 7,726,306 B2 | 6/2010 | Addington |
| 7,771,642 B2 | 8/2010 | Power et al. |
| 7,832,410 B2 | 11/2010 | Hon |
| 7,861,943 B2 | 1/2011 | Feriani et al. |
| 7,883,031 B2 | 2/2011 | Collins, Jr. |
| 7,934,703 B2 | 5/2011 | Tomono et al. |
| 7,950,595 B2 | 5/2011 | Feriani et al. |
| 8,012,136 B2 | 9/2011 | Collins, Jr. et al. |
| 8,109,266 B2 | 2/2012 | Addington |
| 8,187,554 B2 | 5/2012 | Panagiotou |
| 8,328,115 B2 | 12/2012 | Feriani et al. |
| 8,336,545 B2 | 12/2012 | Fink |
| 8,418,690 B2 | 4/2013 | Power et al. |
| 8,545,463 B2 | 10/2013 | Collins, Jr. et al. |
| 8,555,874 B2 | 10/2013 | Fink |
| 8,616,195 B2 | 12/2013 | Power |
| 8,684,980 B2 | 4/2014 | Hunter |
| 8,794,742 B2 | 8/2014 | Yamaguchi |
| 8,888,548 B2 | 11/2014 | Yi |
| 8,888,925 B2 | 11/2014 | Sato et al. |
| 8,910,625 B2 | 12/2014 | Mullinger |
| 8,936,021 B2 | 1/2015 | Collins, Jr. |
| 9,022,027 B2 | 5/2015 | Addington |
| 9,061,303 B2 | 6/2015 | Waldner et al. |
| 9,168,556 B2 | 10/2015 | Pumm et al. |
| 9,220,294 B2 | 12/2015 | McCullough |
| 9,260,849 B2 | 2/2016 | Frey et al. |
| 9,339,838 B2 | 5/2016 | Moran |
| 9,358,569 B2 | 6/2016 | Burt |
| 9,439,455 B2 | 9/2016 | Alarcon |
| 9,533,323 B2 | 1/2017 | Sauzade |
| 9,539,589 B2 | 1/2017 | Araki |
| 9,539,604 B2 | 1/2017 | Wilkerson et al. |
| 9,572,950 B2 | 2/2017 | Power et al. |
| 9,592,524 B2 | 3/2017 | Fritz et al. |
| 9,636,431 B2 | 5/2017 | Teeling et al. |
| 9,718,078 B1 | 8/2017 | Chau et al. |
| 9,744,319 B2 | 8/2017 | Denyer |
| 9,757,528 B2 | 9/2017 | Rubin |
| 9,956,360 B2 | 5/2018 | Germinario |
| 9,962,507 B2 | 5/2018 | Germinario et al. |
| 10,029,053 B2 | 7/2018 | Casey et al. |
| 10,076,140 B2 | 9/2018 | Silvestrini |
| 10,080,736 B2 | 9/2018 | Kleidon |
| 10,292,436 B2 | 5/2019 | Cirillo |
| 10,300,228 B2 | 5/2019 | Minskoff |
| 10,349,674 B2 | 7/2019 | Sur |
| 10,350,556 B2 | 7/2019 | Xiong |
| 10,412,997 B2 | 9/2019 | Cameron et al. |
| 10,449,314 B2 | 10/2019 | Germinario et al. |
| 10,464,095 B2 | 11/2019 | Fritz et al. |
| 10,531,687 B2 | 1/2020 | Liu |
| 10,548,349 B2 | 2/2020 | Sur |
| 10,561,803 B2 | 2/2020 | Liu |
| 10,609,962 B2 | 4/2020 | Zhu |
| 10,617,834 B2 | 4/2020 | Gould |
| 10,661,036 B2 | 5/2020 | McCullough |
| 10,667,559 B2 | 6/2020 | Bessant |
| 10,737,042 B2 | 8/2020 | Minskoff |
| 10,786,010 B2 | 9/2020 | Hubbard |
| 10,792,455 B2 | 10/2020 | Power et al. |
| 10,821,240 B2 | 11/2020 | McCullough |
| 10,856,572 B2 | 12/2020 | Sur |
| 10,857,313 B2 | 12/2020 | Fink |
| 10,888,117 B2 | 1/2021 | Danek |
| 10,918,127 B2 | 2/2021 | Fuisz |
| 11,011,270 B2 | 5/2021 | Hunter et al. |
| 11,027,076 B2 | 6/2021 | Casey et al. |
| 11,027,077 B2 | 6/2021 | Porter et al. |
| 11,039,641 B2 | 6/2021 | Liu |
| 11,077,261 B2 | 8/2021 | Liu |
| 11,131,000 B1 | 9/2021 | Lahoud et al. |
| 11,247,003 B2 | 2/2022 | Rubin |
| 11,253,885 B2 | 2/2022 | Paunescu |
| 11,254,979 B2 | 2/2022 | Alshaiba |
| 11,260,416 B2 | 3/2022 | Wilkerson et al. |
| 11,274,352 B2 | 3/2022 | Lahoud et al. |
| 11,285,274 B2 | 3/2022 | Germinario et al. |

(56) References Cited

U.S. PATENT DOCUMENTS

| | | | |
|---|---|---|---|
| 11,285,283 B2 | 3/2022 | Germinario et al. | |
| 11,285,284 B2 | 3/2022 | Germinario et al. | |
| 11,285,285 B2 | 3/2022 | Germinario et al. | |
| 11,317,476 B2 | 4/2022 | Schmidt | |
| 11,325,149 B2 | 5/2022 | Tan | |
| 11,376,380 B2 | 7/2022 | Biette | |
| 11,445,574 B2 | 9/2022 | Cameron et al. | |
| 11,458,267 B2 | 10/2022 | Hebrank | |
| 11,478,019 B2 | 10/2022 | Qiu | |
| 11,517,039 B2 | 12/2022 | Cameron et al. | |
| 11,517,685 B2 | 12/2022 | Danek | |
| 11,529,476 B2 | 12/2022 | Hunter | |
| 11,553,730 B2 | 1/2023 | Cameron et al. | |
| 11,558,934 B2 | 1/2023 | Ouyang | |
| 11,571,022 B2 | 2/2023 | Lahoud et al. | |
| 11,589,610 B2 | 2/2023 | Lahoud et al. | |
| 11,602,165 B2 | 3/2023 | Lahoud et al. | |
| 11,653,152 B1 | 5/2023 | Lahoud | |
| 11,654,448 B2 | 5/2023 | Aherne et al. | |
| 11,665,483 B1 | 5/2023 | Lahoud | |
| 11,666,713 B2 | 6/2023 | Lahoud | |
| 11,672,928 B2 * | 6/2023 | Lahoud | A61M 15/0085 128/200.16 |
| 11,690,963 B2 * | 7/2023 | Danek | A61M 15/0085 131/328 |
| 11,730,191 B2 | 8/2023 | Lahoud | |
| 11,730,193 B2 | 8/2023 | Lahoud | |
| 11,785,985 B2 | 10/2023 | Lahoud | |
| 2011/0226236 A1 | 9/2011 | Buchberger | |
| 2013/0220315 A1 | 8/2013 | Conley et al. | |
| 2014/0007874 A1 | 1/2014 | Ellwanger et al. | |
| 2015/0238723 A1 | 8/2015 | Knudsen | |
| 2016/0050976 A1 | 2/2016 | Righetti | |
| 2016/0051582 A1 | 2/2016 | Li et al. | |
| 2016/0192708 A1 | 7/2016 | Demeritt | |
| 2016/0374397 A1 | 12/2016 | Jordan et al. | |
| 2018/0043114 A1 | 2/2018 | Bowen et al. | |
| 2018/0043115 A1 * | 2/2018 | Gould | A61M 11/042 |
| 2018/0289907 A1 * | 10/2018 | Marmur | A24F 40/485 |
| 2019/0364957 A1 | 12/2019 | Fu et al. | |
| 2020/0155786 A1 | 5/2020 | Power et al. | |
| 2020/0324066 A1 * | 10/2020 | Potter | A61M 15/06 |
| 2020/0367553 A1 | 11/2020 | Hejazi | |
| 2020/0405995 A1 | 12/2020 | Power et al. | |
| 2021/0001381 A1 | 1/2021 | Qiu | |
| 2021/0052014 A1 * | 2/2021 | Hejazi | A61M 11/04 |
| 2021/0076734 A1 | 3/2021 | Minami et al. | |
| 2021/0084970 A1 * | 3/2021 | Hejazi | A24F 40/10 |
| 2021/0112882 A1 | 4/2021 | Hejazi | |
| 2021/0113783 A1 | 4/2021 | Danek et al. | |
| 2021/0121908 A1 | 4/2021 | Sidawi et al. | |
| 2021/0177055 A1 | 6/2021 | Lahoud | |
| 2021/0178090 A1 | 6/2021 | Lahoud et al. | |
| 2021/0195947 A1 | 7/2021 | Lahoud | |
| 2021/0212370 A1 * | 7/2021 | Moloney | A24F 40/485 |
| 2021/0260312 A1 | 8/2021 | Lacour-gayet et al. | |
| 2021/0282465 A1 | 9/2021 | Cristian | |
| 2021/0283345 A1 | 9/2021 | Porter et al. | |
| 2021/0307376 A1 | 10/2021 | Lahoud et al. | |
| 2021/0310913 A1 | 10/2021 | Lahoud et al. | |
| 2021/0361889 A1 * | 11/2021 | Selby | A61M 11/003 |
| 2021/0402114 A1 | 12/2021 | Lahoud | |
| 2021/0404594 A1 | 12/2021 | Hanson et al. | |
| 2022/0001121 A1 | 1/2022 | Lahoud | |
| 2022/0031975 A1 * | 2/2022 | Selby | A61M 11/003 |
| 2022/0040418 A1 * | 2/2022 | Blick | B05B 17/0646 |
| 2022/0040423 A1 | 2/2022 | Marmur | |
| 2022/0047818 A1 | 2/2022 | Reinhart et al. | |
| 2022/0062565 A1 | 3/2022 | Reinhart et al. | |
| 2022/0062942 A1 | 3/2022 | Greenenko et al. | |
| 2022/0072182 A1 | 3/2022 | Freeman | |
| 2022/0072578 A1 | 3/2022 | Meacham et al. | |
| 2022/0105284 A1 | 4/2022 | Lahoud et al. | |
| 2022/0110362 A1 | 4/2022 | Lahoud et al. | |
| 2022/0132920 A1 | 5/2022 | Danek et al. | |
| 2022/0132935 A1 | 5/2022 | Lahoud | |
| 2022/0175036 A1 | 6/2022 | Hazani et al. | |
| 2022/0218020 A1 | 7/2022 | Lahoud et al. | |
| 2022/0218863 A1 | 7/2022 | Edwards et al. | |
| 2022/0218921 A1 | 7/2022 | Lahoud et al. | |
| 2022/0218922 A1 | 7/2022 | Lahoud et al. | |
| 2022/0218923 A1 | 7/2022 | Lahoud et al. | |
| 2022/0225664 A1 | 7/2022 | Lahoud et al. | |
| 2022/0226587 A1 | 7/2022 | Hunter | |
| 2022/0226856 A1 | 7/2022 | Anzenberger et al. | |
| 2022/0243289 A1 | 8/2022 | Lahoud et al. | |
| 2022/0296823 A1 | 9/2022 | Lahoud et al. | |
| 2022/0338535 A1 | 10/2022 | Danek | |
| 2022/0361564 A1 | 11/2022 | Lahoud et al. | |
| 2022/0361565 A1 | 11/2022 | Lahoud et al. | |
| 2022/0361567 A1 | 11/2022 | Lahoud et al. | |
| 2022/0362490 A1 | 11/2022 | Lahoud et al. | |
| 2022/0362494 A1 | 11/2022 | Lahoud et al. | |
| 2022/0369698 A1 | 11/2022 | Lahoud et al. | |
| 2022/0369699 A1 | 11/2022 | Lahoud et al. | |
| 2022/0370737 A1 | 11/2022 | Lahoud et al. | |
| 2022/0370739 A1 | 11/2022 | Lahoud | |
| 2022/0370740 A1 | 11/2022 | Lahoud et al. | |
| 2022/0400745 A1 | 12/2022 | Lahoud | |
| 2022/0400746 A1 | 12/2022 | Lahoud | |
| 2023/0001107 A1 | 1/2023 | Connolly et al. | |
| 2023/0028847 A1 | 1/2023 | Lee et al. | |
| 2023/0118045 A1 | 4/2023 | Danek et al. | |
| 2023/0166284 A1 | 6/2023 | Aherne et al. | |
| 2023/0337735 A1 | 10/2023 | Danek | |

FOREIGN PATENT DOCUMENTS

| | | |
|---|---|---|
| EP | 1154815 | 7/2004 |
| WO | 2021203038 A1 | 10/2021 |
| WO | 2022/051496 | 3/2022 |
| WO | 2022/079037 | 4/2022 |
| WO | 2022/096589 | 5/2022 |
| WO | 2022/129906 | 6/2022 |
| WO | 2022/179854 | 9/2022 |
| WO | 2022/200151 | 9/2022 |
| WO | 2023111495 A1 | 6/2023 |
| WO | 2023111496 A1 | 6/2023 |

OTHER PUBLICATIONS

"Biocompatibility of Medicinal Product Medical Device Combination for Airway Delivery" (Turner), May 17, 2021, retrieved from https://ondrugdelivery.com/biocompatibility-of-medicinal-product-medical-device-combinations-for-airway-delivery.

* cited by examiner exit port for aerosol

30 exit port for aerosol

30 usb port for charging battery

*FIG. 3a* exit port for aerosol

30 usb port for charging battery

*FIG. 3c*

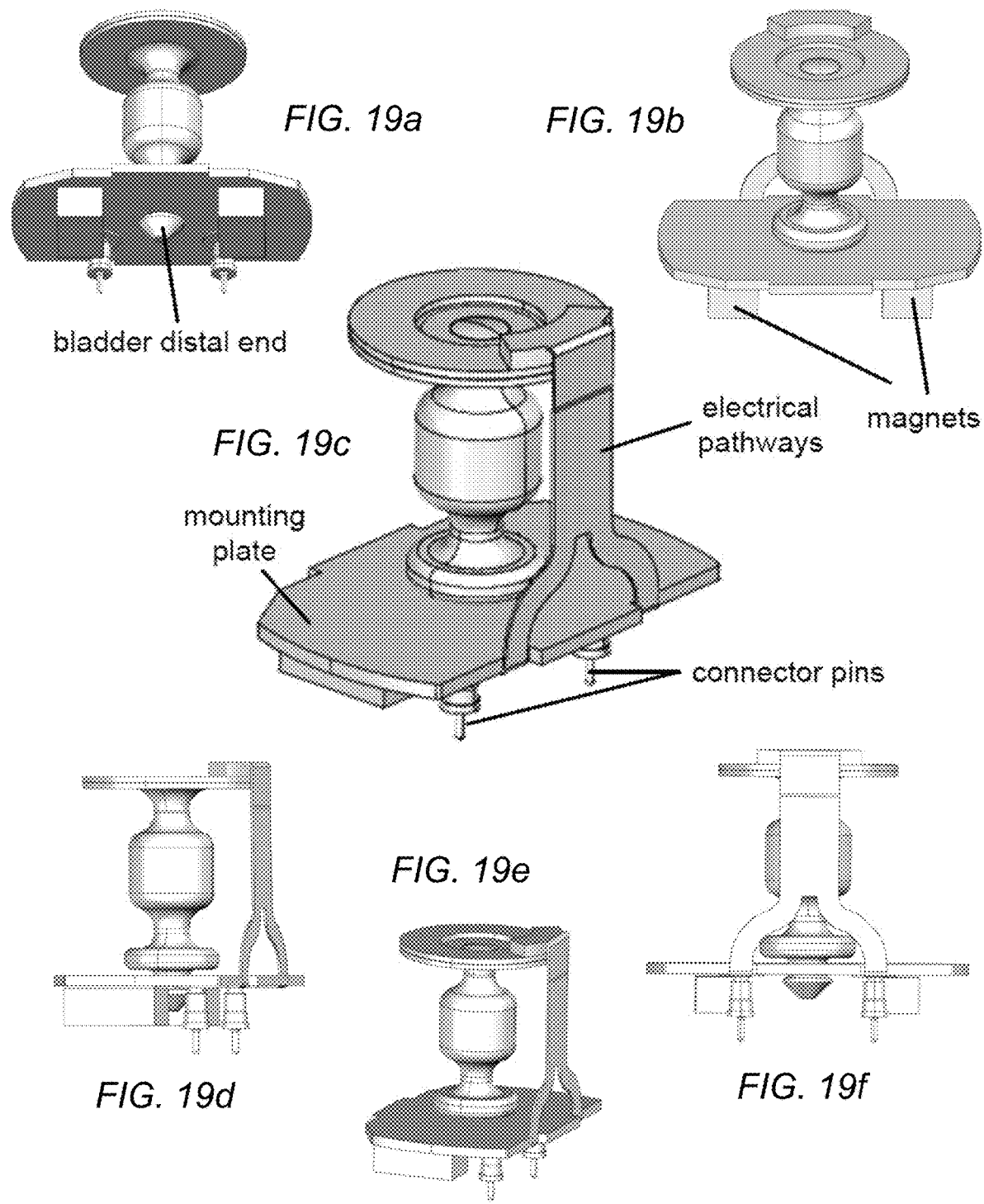

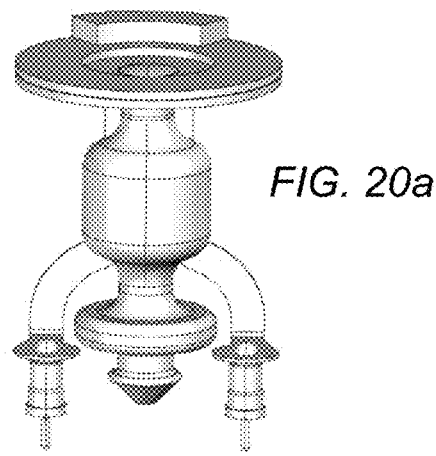
FIG. 20a
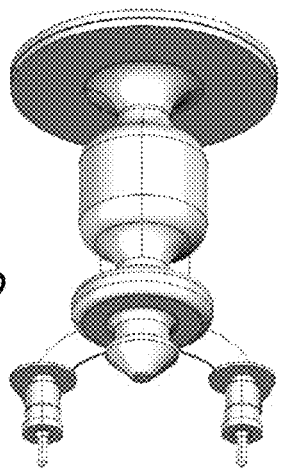
FIG. 20b
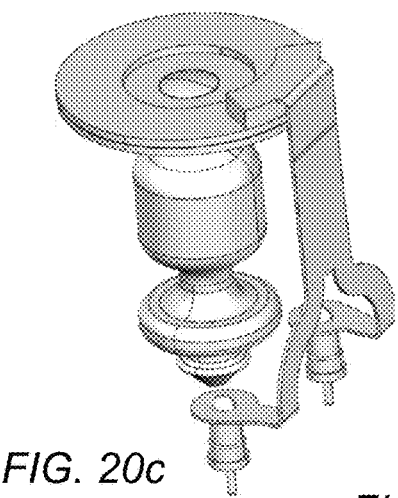
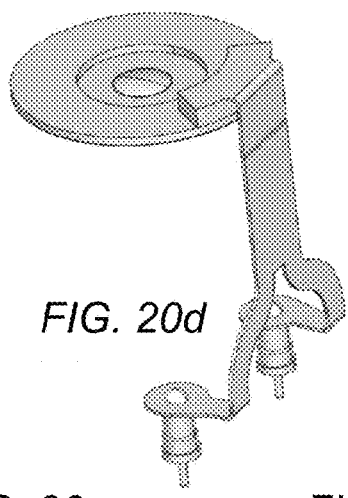
FIG. 20d
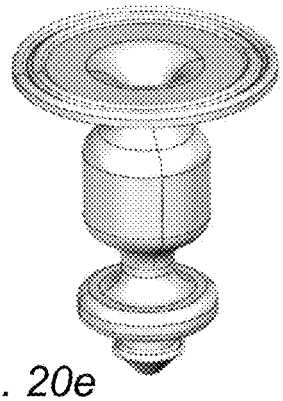
FIG. 20c
FIG. 20e
FIG. 20g
FIG. 20h
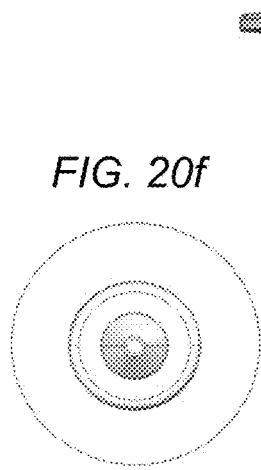
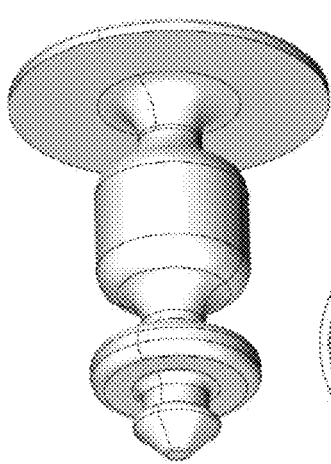
FIG. 20f
FIG. 20i
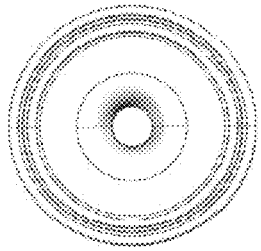

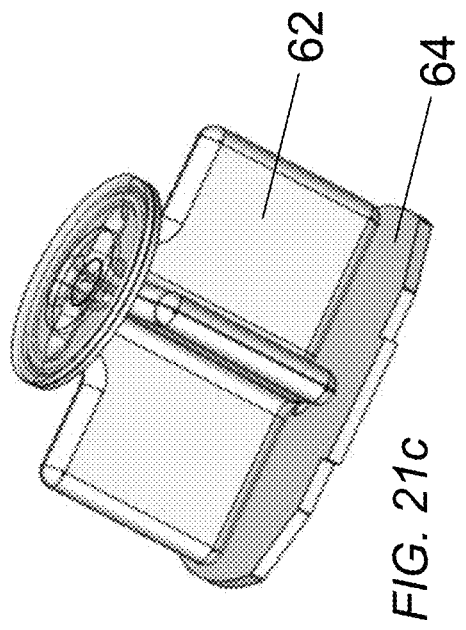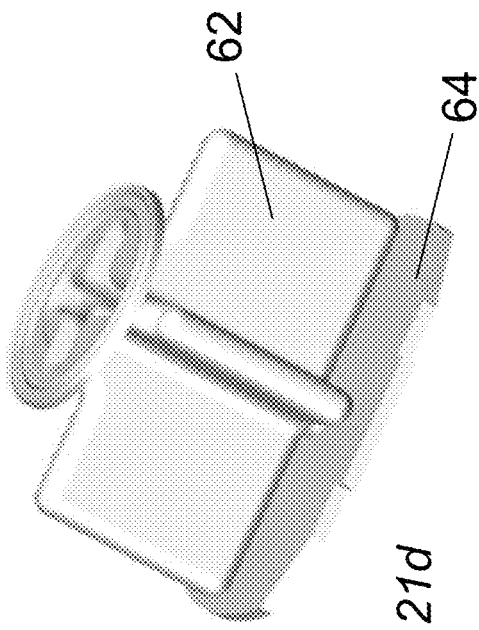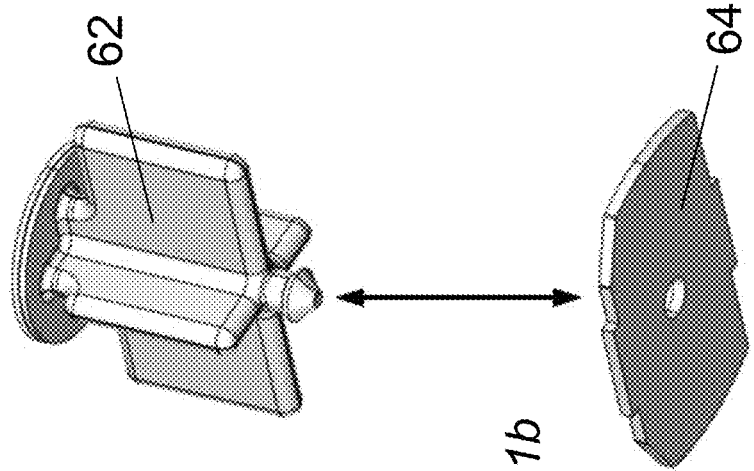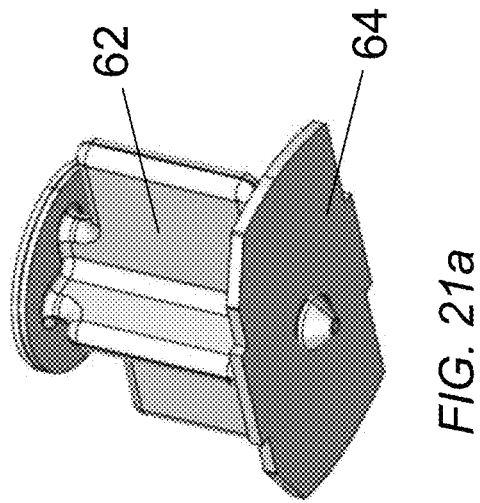

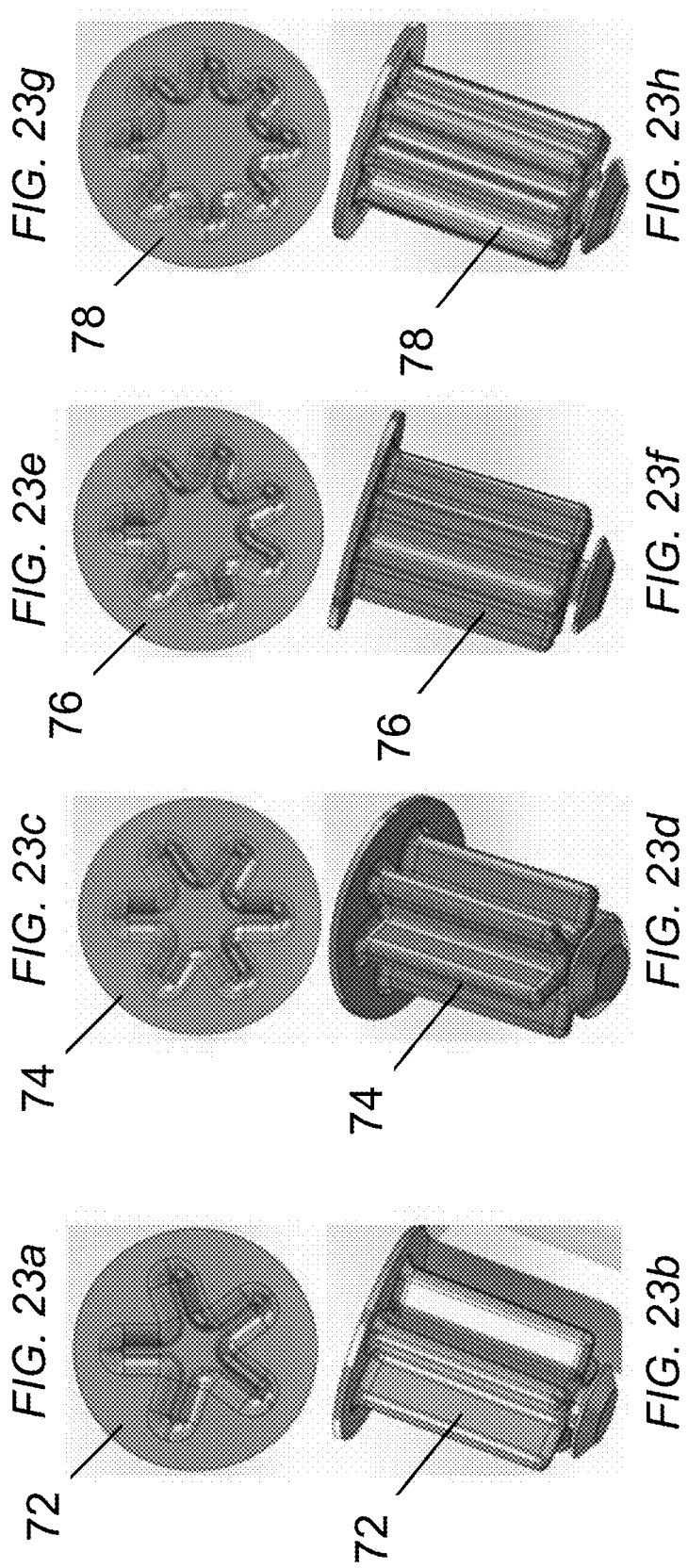

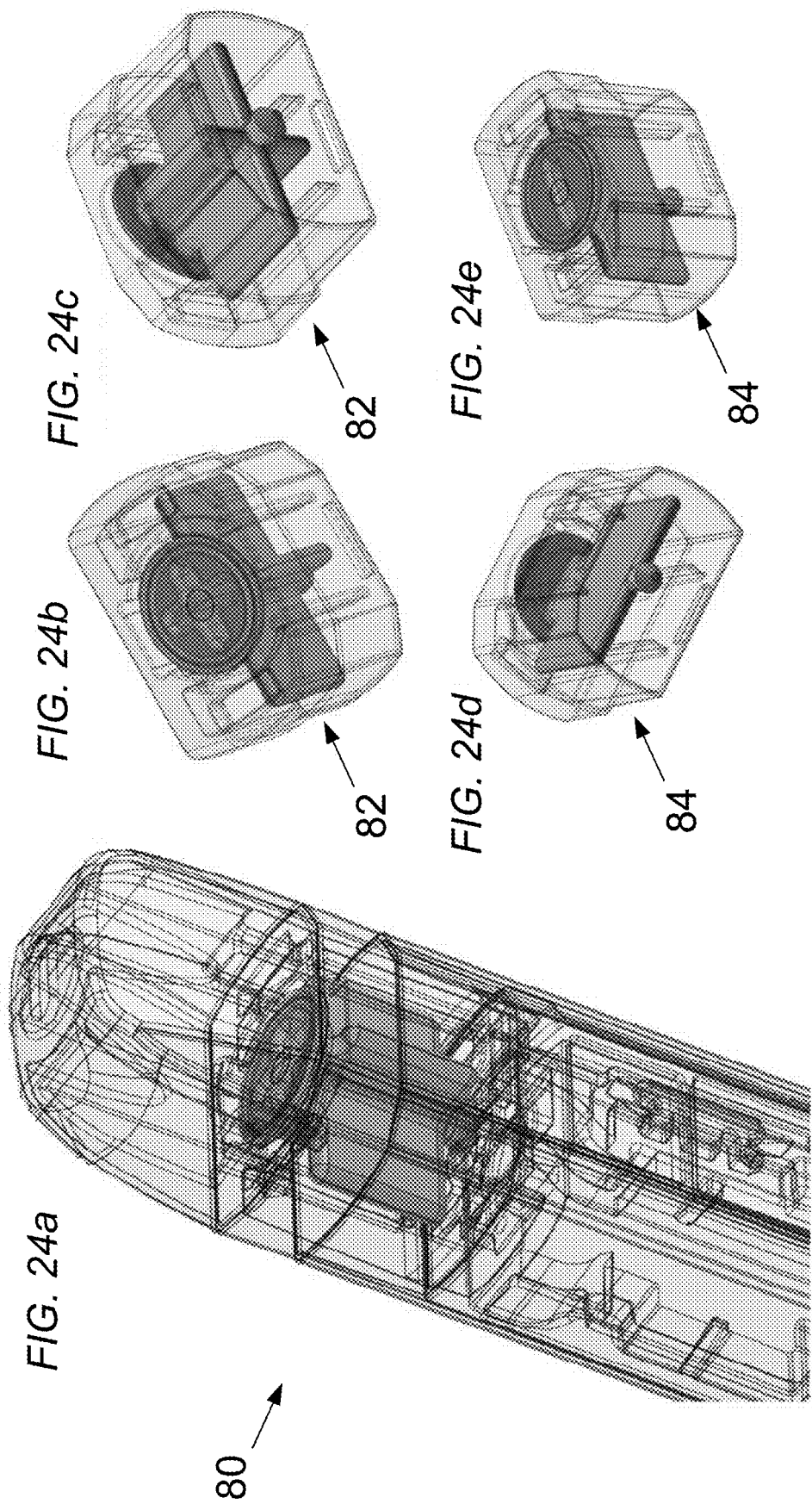

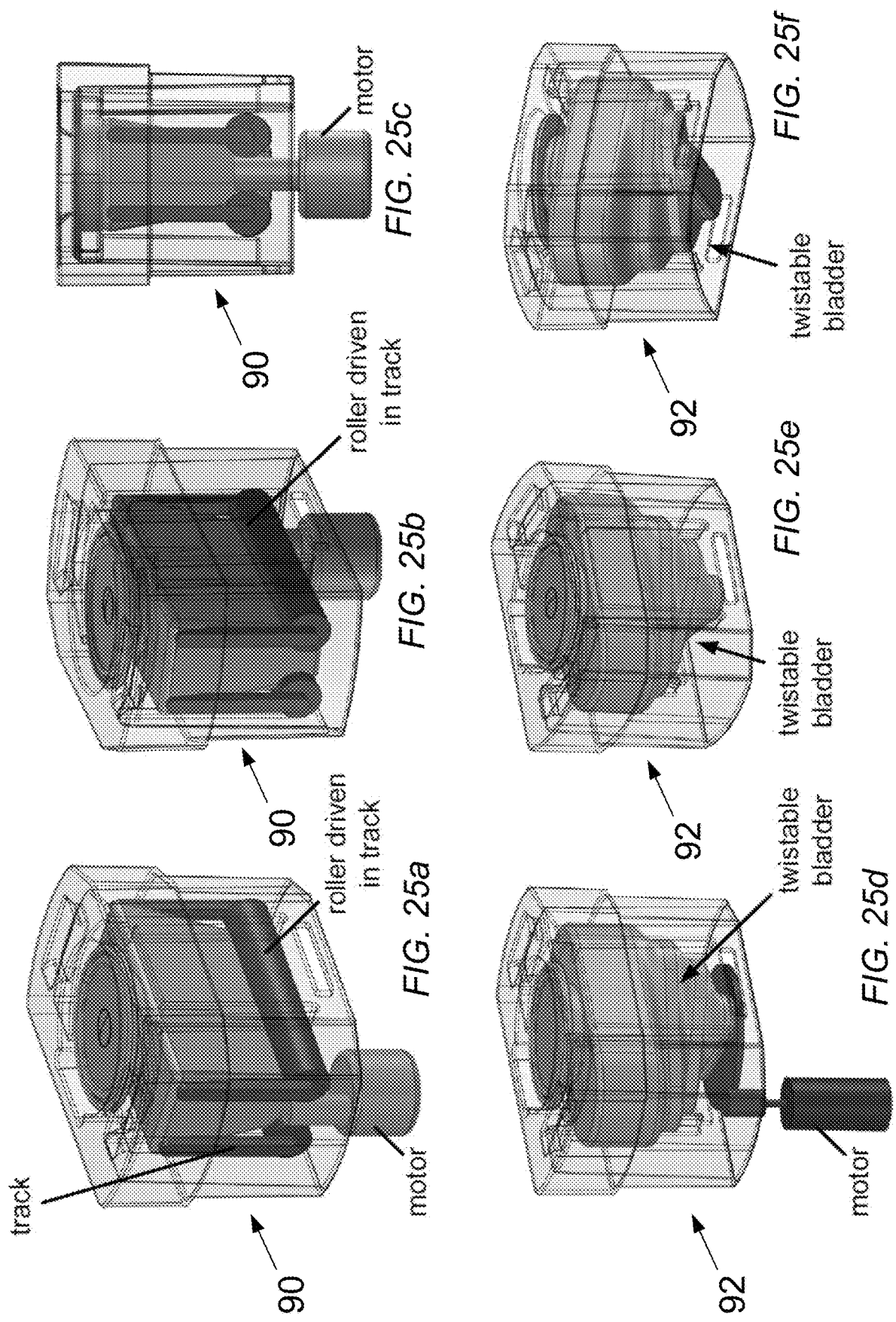

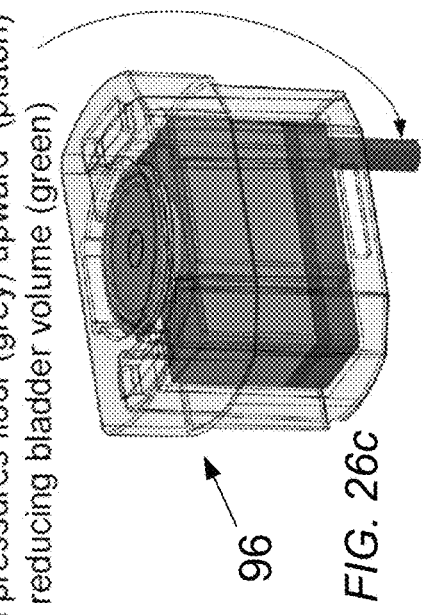

FIG. 26c floor (grey) of chamber containing bladder is moved upward (piston), reducing volume of bladder (green)

secondary fluid (air or liquid) pumped via pipe to chamber containing bladder; secondary liquid pressures floor (grey) upward (piston) reducing bladder volume (green)

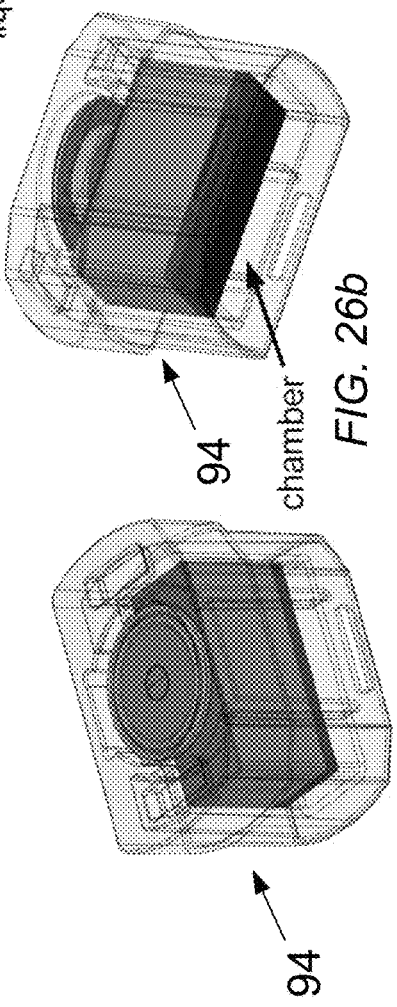

FIG. 26d springs (red) bias floor (grey) upward like piston as liquid is aerosolized, reducing volume of bladder (green)

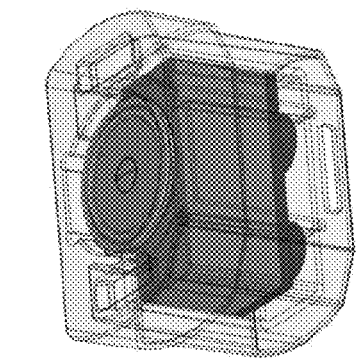

FIG. 26e

FIG. 26f peristaltic pump me

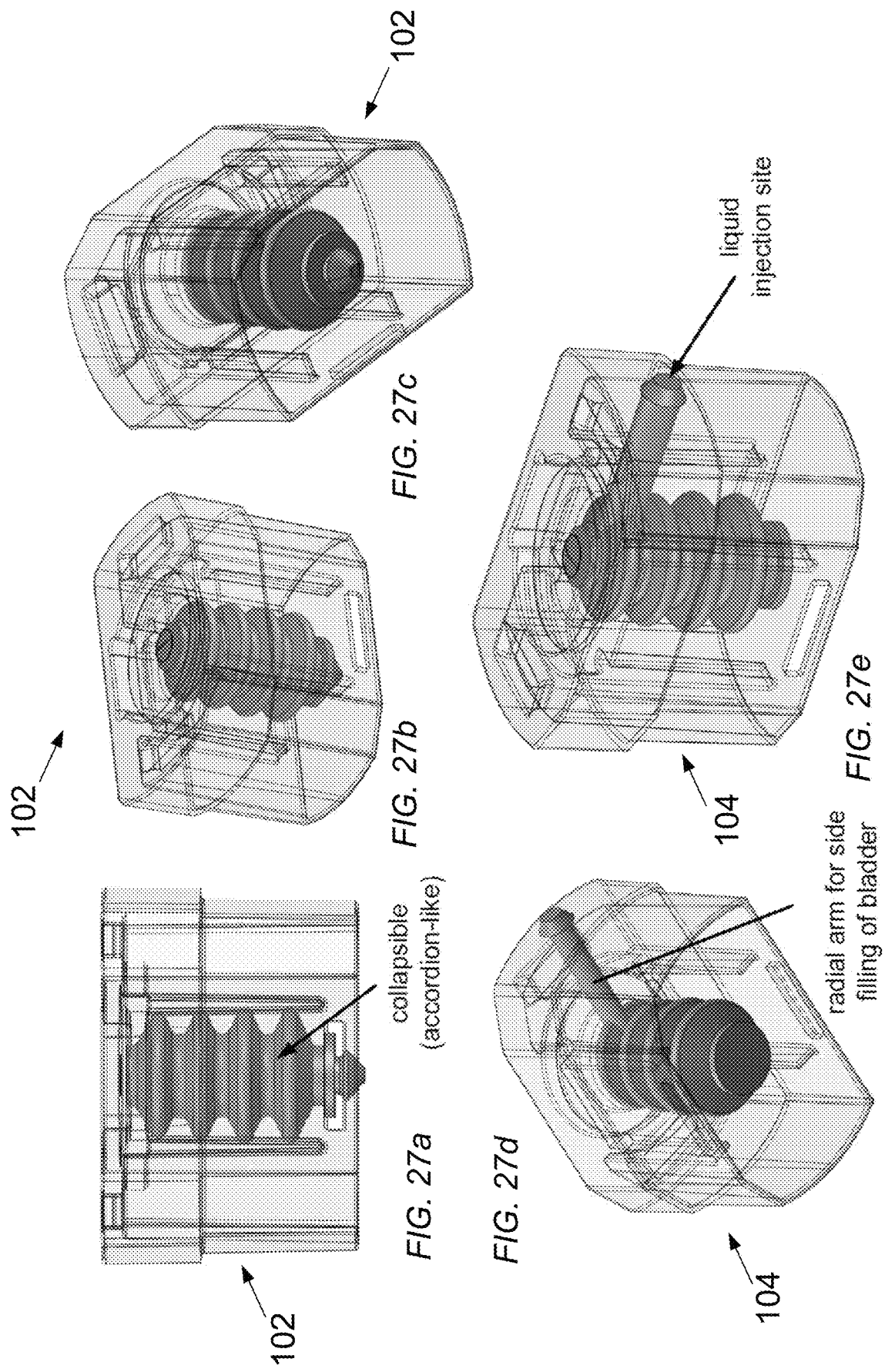

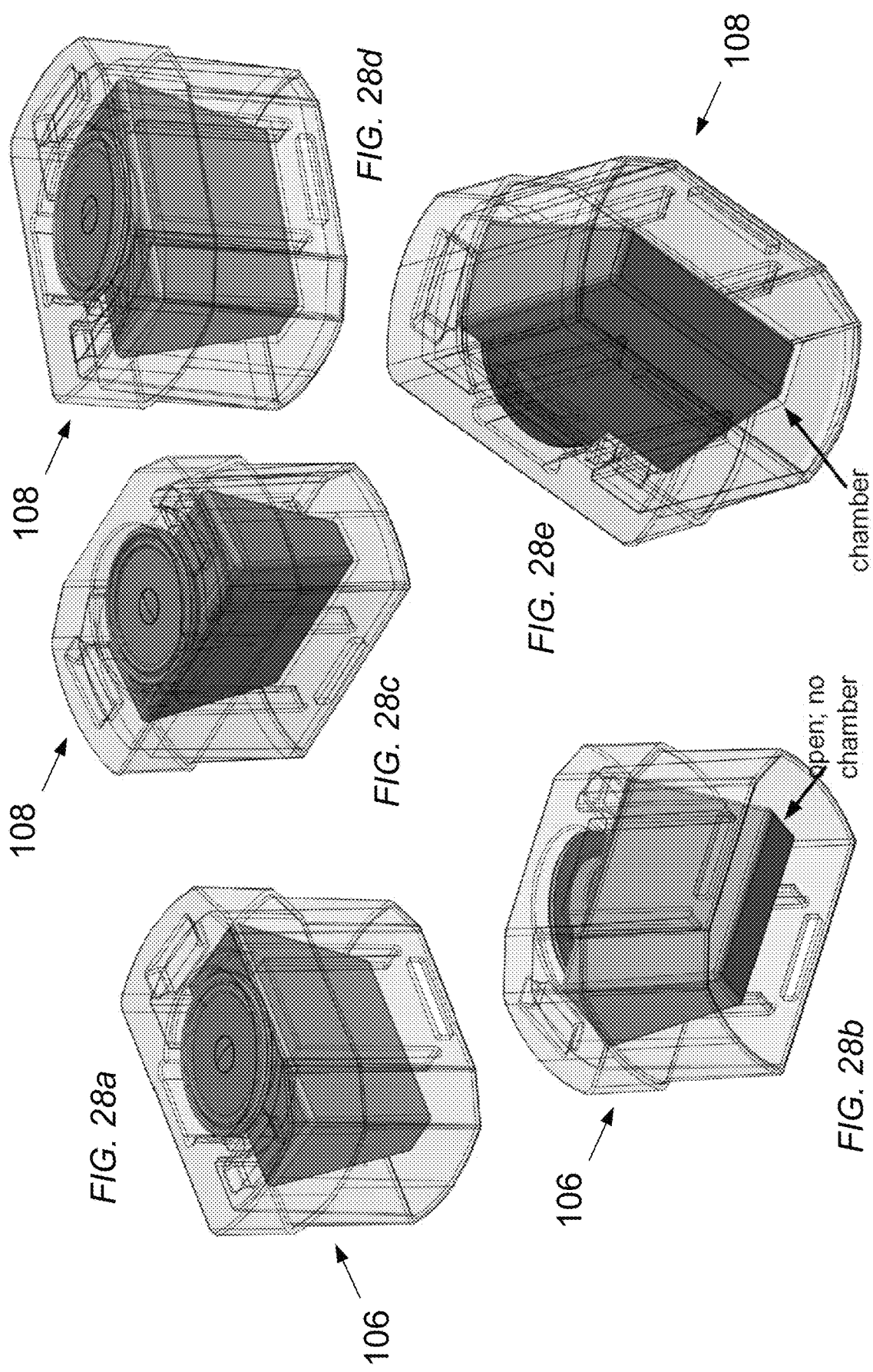

compressed foam pressures bladder

112 compressed foam pressures bladder

112

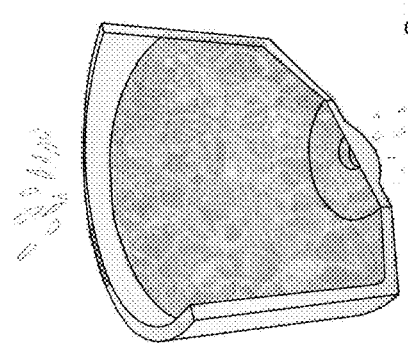
Gravity Fed
Pros: minimal parts
Cons: orientation specific, condensation through inhalation path

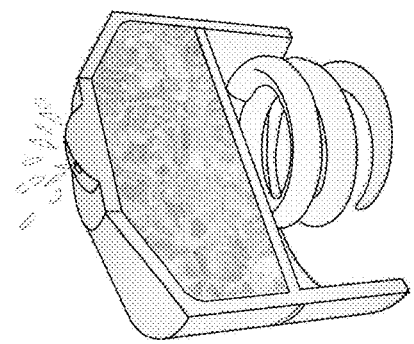
Spring Pressure Control
Pros: feed rate control works in any orientation
Cons: high tolerance on parts needed to achieve functionality

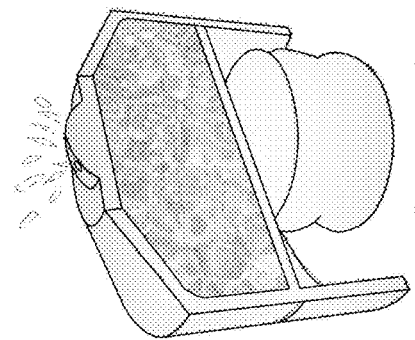
Compressed Open Cell Foam
Pros: same as spring with safety net for leakage
Cons: same as spring

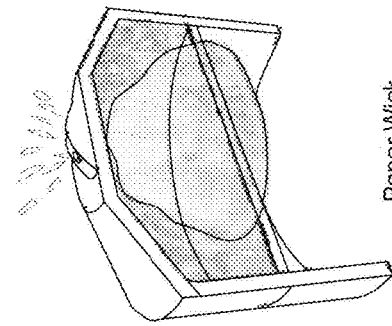
Paper Wick
Pros: Works in any orientation, minimal parts
Cons: Reduced dispersion rate, possibly of material separation in liquid

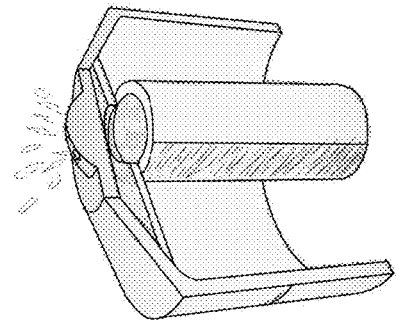
Capillary Tube
Pros: Works in any orientation, simple design
Cons: Small volume and long tube length

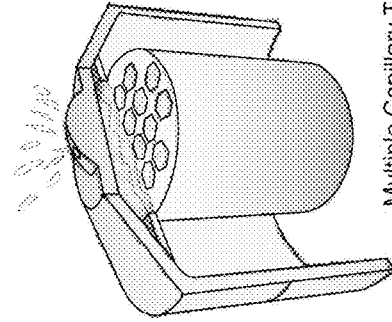
Multiple Capillary Tubes
Pros: Same as capillary tube
Cons: large volume needed to accommodate tubes and liquid

FIG. 31

ELECTRONIC DEVICES AND LIQUIDS FOR AEROSOLIZING AND INHALING THEREWITH

CROSS-REFERENCE TO APPLICATIONS

This application is a continuation of, and claims the benefit under 35 U.S.C. § 120 to, U.S. nonprovisional patent application Ser. No. 17/075,679, filed Oct. 20, 2020, which '679 application and publication thereof 2021/0113783 are incorporated herein by reference, and which '679 application claims the benefit under 35 U.S.C. § 119(e) to each of U.S. provisional patent applications: 62/923,563, filed Oct. 20, 2019; 62/923,602, filed Oct. 20, 2019; 62/923,604, filed Oct. 20, 2019; 62/924,168, filed Oct. 21, 2019; and 62/924,171, filed Oct. 21, 2019, each of which is incorporated herein by reference. This application also incorporates by reference Applicant's U.S. patent application Ser. Nos. 16/548,831; 16/657,732; and Ser. No. 16/657,755, and any U.S. patent application publication thereof and any U.S. patent issuing therefrom, including publication 2020/0060338, publication 2020/0060349, and patent 10,888,117. United States patent application publication 2023/0121005 representing the publication of the present application also is incorporated berein by reference ("the '005 Publication"), Aspects and features of the invention are believed to be improvements and enhancements over the devices and methods of Applicant's '831, '732, and '755 applications.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.
Computer Program Listing Submitted concurrently herewith via the USPTO's electronic filing system, and incorporated herein by reference, are computer program files. A table setting forth the name and size of files included in this computer program listing is included below.

| File Name | Creation Date | File Size (bytes) |
|---|---|---|
| ascify.txt | Oct. 21, 2019 12:42 | 37,473 |
| readme.txt | Oct. 21, 2019 12:40 | 2,741 |
| files1.txt | Oct. 20, 2019 19:25 | 22,478,505 |
| files2.txt | Oct. 20, 2019 19:25 | 11,960,834 |

One of these files, "readme.txt", contains instructions for extracting information from files "files1.txt" and "files2.txt". Files "files1.txt" and "files2.txt" collectively represent a compressed binary file that has been converted to ascii format. These files can be converted back to a compressed .zip archive utilizing an assembly conversion program source code for which is contained in file "ascify.txt". The readme file includes instructions for compiling and running this conversion program, and instructions for converting the other text files to a compressed, binary file.

This compressed, binary file includes eDrawings files for a computer model illustrating aspects and features in accordance with one or more preferred embodiments, as well as a .pdf file illustrating aspects and features in accordance with one or more preferred embodiments.

BACKGROUND OF THE INVENTION

The invention generally relates to apparatus, systems, and methods for producing an aerosol for inhalation by a person, whether intended for personal or recreational use, or for the administration of medicines.

Vaping has been rapidly increasing in popularity, primarily because vaping provides a convenient, discreet, and presumably benign way to self-administer nicotine, *cannabis*, drugs or other micronutrients. Indeed, there is a common belief that vaping is healthier than smoking cigarettes; vaping purportedly lets smokers avoid dangerous chemicals inhaled from regular cigarettes while still getting nicotine. Vaping also can be used for *cannabis*.

Vaping is performed using a vaporizer. A vaporizer includes a vape pen or a cigarette style vape, referred to by many as an e-cigarette or "eCig". A vape pen generally is an elongate, thin, and stylized tube that resembles a fancy pen. In contrast, an e-cigarette resembles an actual cigarette. The e-cigarette is usually small in size (usually smaller and more discreet than vape pens), easily portable, and easy to use.

A common vaporizer comprises a container, which may be a tank—which is typically refillable, or a cartridge—which is typically single-use and not refillable. The tank or cartridge holds a liquid often referred to as an e-liquid or e-juice. Tanks are made out of polycarbonate plastic, glass, or stainless steel. The vaporizer also includes a mouthpiece for inhaling by a person through the mouth; an atomizer comprising a tiny heating element that converts the liquid into tiny, airborne droplets that are inhaled; and a controller for turning on the atomizer. Many vape pens are mouth-activated and turn on automatically when a person inhales. Others vape pens are button activated and require the person to push a button to activate the atomizer. Vaporizers are electrically powered using one or more batteries. The batteries typically are lithium ion batteries that are rechargeable and primarily are used to heat the heating element of the atomizer. A charger usually accompanies a vaporizer when purchased for charging the batteries. The charger may be a USB charger, car charger, or wall charger, and such chargers are generally similar to phone chargers.

The battery-powered vaporizer produces vapor from any of a variety of liquids and liquid mixtures, especially those containing nicotine or cannabinoids. Many different types and flavors are available. Moreover, the liquids can be non-medicated (i.e., containing no nicotine or other substances— just pure vegetable glycerin and flavoring), or the liquids can contain nicotine or even in some instances if and where legal, the liquids can contain THC/CBD. The liquids also may contain one or more of a variety of flavors as well as micronutrients such as, for example, vitamin B12. A person can mix the liquids for use with a vape pen. E-cigarettes typically are purchased with prefilled cartridges. The heating element turns the contents of the liquids into an aerosol—the vapor—that is inhaled into the lungs and then exhaled by the person. Perhaps one of the most popular vaporizers today is known as the "JUUL", which is a small, sleek device that resembles a computer USB flash drive.

It is believed that while promoted as healthier than traditional cigarette use, vaping actually may be more dangerous. Propylene glycol, vegetable glycerin and combinations or methylations thereof, are chemicals that are often mixed with nicotine, *cannabis*, or hemp oil for use in vaporizers. Propylene glycol is the primary ingredient in a majority of nicotine-infused e-cigarette liquids. Unfortunately, at high temperatures propylene glycol converts into tiny polymers that can wreak havoc on lung tissue. In particular, scientists know a great deal about propylene glycol. It is found in a plethora of common household items—cosmetics, baby wipes, pharmaceuticals, pet food, antifreeze, etc. The U.S. Food and Drug Administration and Health Canada have deemed propylene glycol safe for human ingestion and topical application. But exposure by inhalation is another matter. Many things are safe to eat but dangerous to breathe. Because of low oral toxicity, propylene glycol is classified by the FDA as "generally recognized as safe" (GRAS) for use as a food additive, but this assessment was based on toxicity studies that did not involve heating and breathing propylene glycol. Indeed, a 2010 study published in the International Journal of Environmental Research and Public Health concluded that airborne propylene glycol circulating indoors can induce or exacerbate asthma, eczema, and many allergic symptoms. Children were said to be particularly sensitive to these airborne toxins. An earlier toxicology review warned that propylene glycol, ubiquitous in hairsprays, could be harmful because aerosol particles lodge deep in the lungs and are not respirable.

Moreover, when propylene glycol is heated, whether by a red-hot metal coil of a heating element of a vaporizer or otherwise, the potential harm from inhalation exposure increases. It is believed that high voltage heat transforms the propylene glycol and other vaping additives into carbonyls. Carbonyls are a group of cancer-causing chemicals that includes formaldehyde, which has been linked to spontaneous abortions and low birth weight. A known thermal breakdown product of propylene glycol, formaldehyde is an International Agency for Research on Cancer group 1 carcinogen!

Prevalent in nicotine e-cig products and present in some vape oil cartridges, FDA-approved flavoring agents pose additional risks when inhaled rather than eaten. The flavoring compounds smooth and creamy (diacetyl and acetyl propionyl) are associated with respiratory illness when inhaled in tobacco e-cigarette devices. Another hazardous-when-inhaled-but-safe-to-eat flavoring compound is Ceylon cinnamon, which becomes cytotoxic when aerosolized.

When a heating element gets red hot in a vaporizer, the liquid undergoes a process called "smoldering", which is a technical term for what is tantamount to "burning"; while much of the liquid is vaporized and atomized, a portion of the liquid undergoes pyrolysis or combustion. In that sense, most of the vaporizers that have flooded the commercial market may not be true vaporizers.

Additionally, clearance mechanisms of the lung, like all major points of contact with the external environment, have evolved to prevent the invasion of unwanted airborne particles from entering the body. Airway geometry, humidity and clearance mechanisms contribute to this filtration process.

In view of the foregoing, it is believed that a need exists for a vaporizer that provides an aerosol of the desired chemicals without the harmful byproducts that arise from smoldering. It is also believed that a need exists for a vaporizer that effectively and efficiently produces a vapor cloud that is not inhibited by the body's natural filtration process. This and other needs are believed to be met by embodiments in accordance with one or more aspects and features of the invention.

Furthermore, the invention also generally relates to apparatus, systems, formulations, and methods pertaining to liquids that are aerosolized and inhaled by persons using electronic devices, whether intended for personal or recreational use, or for the administration of medicines.

Inhalation delivery systems now play an increasing role in the targeted delivery of active ingredients to the human pulmonary system. This is true both for medical purposes, such as the targeted delivery of anti-cancer medications to the lungs, as well as for recreational/personal purposes, such as vaping, in which a liquid that includes the active ingredient is vaporized using heating so that the active ingredient can be inhaled into the human body.

Unfortunately, as inhalation delivery systems using heating have increased in prominence, concerns about their short and long term safety have come into focus. This is particularly true for vaping where there exist ongoing concerns about the possible presence of harmful and potentially harmful constituents (HPHCs) in the inhaled vapor. Moreover, inhalation delivery systems are often unable to provide the desired effect to a user. This may be attributable to the pre-vaporized liquid becoming unstable over time or the active ingredient itself not being properly sized or dispersed for deposition in the alveolar lung.

Accordingly, a need exists for an active ingredient delivery system that enhances the shelf-life of the pre-vaporized liquid component and enhances the efficacy of the desired treatment/effect, while avoiding the presence of undesired HPHCs in the inhaled vapor. This, and other needs, are believed to also be addressed by one or more aspects and features of the invention.

SUMMARY OF THE INVENTION

The invention includes many aspects and features. Moreover, while many aspects and features relate to, and are described in, the context of vaping, the invention is not limited to use only in such context. Indeed, depending on the context of use, the electronic device of the invention may be considered a vaporizer and may be in the form of a vape pen or e-cigarette. Indeed, those who vape may come to refer to embodiments of the invention as a vape pen even though heat is not utilized to create the aerosol that is inhaled. In the delivery of pharmaceuticals, patients may come to refer to embodiments of the invention as a nebulizer even though a gas transport (e.g., compressed gas) is not utilized and even though the aerosol that is produced in accordance with the invention may have a smaller particle size than the mist produced by common nebulizers. Other separate and distinct contexts of use of embodiments of the invention may similarly result in different nomenclature of the embodiments of the invention. Nonetheless, while the appearance and form factor of embodiments of the invention may vary depending on such contexts of use, the basic components and operation remain the same, except where otherwise described below.

Some embodiments in accordance with aspects and features of the present invention preferably utilize a bladder for supplying the liquid to the mesh assembly, the piezoelectric material of which aerosolizes the liquid for inhalation by a person. The bladder may be used in replacement of the "liquid container" of Applicant's '831, '732, and '755 applications, with the bladder preferably forming a part of a disposable cartridge. Additionally, the bladder preferably is formed from a self-healing material such as silicone and is filled with the fluid by injection. The injection process preferably occurs during the manufacture of the cartridge after the bladder has been formed and installed into the cartridge. the injection site of the bladder preferably is the end of the bladder distally located to the port of the mouthpiece through which the aerosol is inhaled. Alternatively, the injection site of the bladder may be located to a side of the bladder. Various shapes and sizes of bladders are disclosed in the current application, including collectively the drawings and the eDrawings and PDF files of the computer program listing, which is incorporated herein by reference and which forms part of the disclosure of the present application.

Aspects of the invention also comprises using an electronic device of the present invention to produce an aerosol for inhalation by a person using such electronic device.

Additional features of the invention are set forth in any and each incorporated application of Applicant, including any incorporated U.S. patent application publication thereof and any incorporated U.S. patent issuing therefrom.

In another aspect, a liquid-filled cartridge for use with an electronic device for delivery of a substance into a body through respiration comprises: a liquid container; and (b) a liquid contained within the container for aerosolizing and inhaling by a person using the electronic device, the liquid comprising a plurality of nanoparticles in a nanoemulsion, each nanoparticle comprising an encapsulation of the substance to be delivered into the body through respiration.

In a feature, the liquid is an oil-in-water nanoemulsion.

In a feature, each nanoparticle is a micelle.

In a feature, each nanoparticle is a liposome.

In a feature, the substance is encapsulated by a polymer.

In a feature, the substance is encapsulated by a surfactant. The surfactant preferably comprises high purity polyoxyethylene sorbitan monooleate.

In a feature, the encapsulated substance comprises tetrahydrocannabinol.

In a feature, the encapsulated substance comprises cannabidiol.

In a feature, the encapsulated substance comprises tetrahydrocannabinol and cannabidiol.

In a feature, the encapsulated substance comprises a pharmaceutical compound.

In a feature, the encapsulated substance comprises nicotine.

In a feature, wherein the nanoparticles are suspended within an aqueous solution. The aqueous solution preferably comprises a saline; the aqueous solution preferably comprises sodium chloride; and, the nanoparticles preferably are suspended within an aqueous solution of 0.9% sodium chloride.

In a feature, a pH of the liquid is between about 5.5 and about 8.

In a feature, wherein a pH of the liquid is between about 6.5.

In a feature, a molecular ratio of the encapsulated substance to an encapsulating agent of the nanoparticle between about 0.1:1 to about 10:1.

In a feature, a polydispersity index measurement of the liquid is less than 0.3.

In a feature, the cartridge is a single-use, disposable cartridge.

In a feature, the cartridge is refillable.

In another aspect, a method of manufacturing cartridges for use with an electronic device for delivery of a substance into a body through respiration comprises filling a liquid container of the cartridge with a liquid for aerosolizing and inhaling by a person using the electronic device, the liquid comprising a plurality of nanoparticles in a nanoemulsion, each nanoparticle comprising an encapsulation of the substance to be delivered into the body through respiration.

In a feature, the method further comprises a preliminary step of producing the nanoemulsion by processing the substance to be delivered together with the encapsulating agent using a microfluidizing machine.

In a feature, the method further comprises operating the microfluidizing machine such that a temperature of the processing does not exceed 65° C. while producing the nanoemulsion.

In a feature, the method further comprises the step of adjusting pH of the nanoemulsion so as to be between about 5.5 and 8.

In a feature, the method further comprises the step of chemically bonding the substance to be encapsulated with another molecule prior to processing the substance with the encapsulating agent using the microfluidizing machine. The polydispersity index measurement of the nanoemulsion after processing using the microfluidizing machine preferably is less than 0.3.

In another aspect, a method of manufacturing a liquid for aerosolizing and inhaling by a person using an electronic device for the delivery of a substance to the body of the person through respiration, the method comprising producing a liquid comprising a plurality of nanoparticles in a nanoemulsion by processing the substance together with an encapsulating agent using a microfluidizing machine such that the plurality of nanoparticles of the liquid comprises the encapsulated substance.

In a feature, the method further comprises operating the microfluidizing machine such that a temperature of the processing does not exceed 65° C. while producing the liquid.

In a feature, the method further comprises adjusting pH of the nanoemulsion so as to be between about 5.5 and 8.

In a feature, the method further comprises the step of chemically bonding the substance to be encapsulated with another molecule prior to processing the substance with the encapsulating agent using the microfluidizing machine.

In a feature, a polydispersity index measurement of the nanoemulsion after processing using the microfluidizing machine is less than 0.3.

Another aspect of the invention relates to a liquid formulation for aerosolization. The liquid formulation includes an aqueous solution, one or more encapsulating agents, and an active ingredient.

In a feature of this aspect, the active ingredient is encapsulated by one or more encapsulating agents to form a nanoparticle. In another feature of this aspect, the nanocarrier comprises a liposome. In still another feature of this aspect, the nanocarrier comprises a micelle.

In another feature of this aspect, the nanoparticles have an average diameter of less than 1,000 nanometers.

In another feature of this aspect, the one or more encapsulating agents comprise a polymer. In another feature of this aspect, the one or more encapsulating agents comprise a surfactant. In still another feature of this aspect, the surfactant comprises a high purity polyoxyethylene sorbitan monooleate, such as "SUPER REFINED Polysorbate 80".

In another feature of this aspect, the aqueous solution comprises a saline solution. In another feature of this aspect, the saline solution comprises a 0.9% saline solution.

In another feature of this aspect, the active ingredient comprises tetrahydrocannabinol. In another feature of this aspect, the active ingredient comprises cannabidiol. In another feature of this aspect, the active ingredient comprises tetrahydrocannabinol and cannabidiol. In another feature of this aspect, the active ingredient comprises nicotine. In still another feature of this aspect, the active ingredient comprises a pharmaceutical compound.

In another feature of this aspect, a ratio of the one or more encapsulating agents to the active ingredient is between about 0.1:1 to about 10:1.

In another feature of this aspect, a pH measurement of the liquid formulation is between about 5.5 and about 8. In another feature of this aspect, a pH measurement of the liquid formulation is about 6.5.

In another feature of this aspect, a polydispersity index measurement of the liquid formulation is less than 0.3.

In another feature of this aspect, the active ingredient is chemically bonded to another molecule.

Another aspect of the invention relates to a method of preparing a liquid formulation for aerosolization. The method comprises the steps of mixing nanoparticles that include an active ingredient in a solution to form a liquid mixture and processing the liquid mixture with a microfluidizer.

In a feature of this aspect, a temperature of the liquid mixture does not exceed 65° C. during the processing step.

In another feature of this aspect, the method further comprises the step of adjusting the pH of the liquid mixture.

In another feature of this aspect, the method further comprises the step of chemically bonding the active ingredient with another molecule.

In another feature of this aspect, nanoparticles of the microfluidized liquid mixture have an average diameter less than 1,000 nanometers.

In another feature of this aspect, a polydispersity index measurement of the microfluidized liquid mixture is less than 0.3.

In another feature of this aspect, the solution comprises an aqueous solution. In another feature of this aspect, the aqueous solution comprises a 0.9% saline solution.

In another feature of this aspect, the nanoparticles comprise encapsulated nanoparticles. In another feature of this aspect, the active ingredient is contained within the encapsulated nanoparticles. In another feature of this aspect, the nanocarrier comprises a liposome. In still another feature of this aspect, the nanocarrier comprises a micelle.

In another feature of this aspect, the active ingredient comprises tetrahydrocannabinol. In another feature of this aspect, the active ingredient comprises cannabidiol. In another feature of this aspect, the active ingredient comprises tetrahydrocannabinol and cannabidiol. In another feature of this aspect, the active ingredient comprises nicotine. In still another feature of this aspect, the active ingredient comprises a pharmaceutical compound.

In addition to the aforementioned aspects and features of the invention, it should be noted that the invention further encompasses the various logical combinations and subcombinations of such aspects and features. Thus, for example, claims in this or a divisional or continuing patent application or applications may be separately directed to any aspect, feature, or embodiment disclosed herein, or combination thereof, without requiring any other aspect, feature, or embodiment.

BRIEF DESCRIPTION OF THE DRAWINGS

One or more preferred embodiments of the invention now will be described in detail with reference to the accompanying drawings, wherein the same elements are referred to with the same reference numerals.

Figures 1A, 1B, 1C:
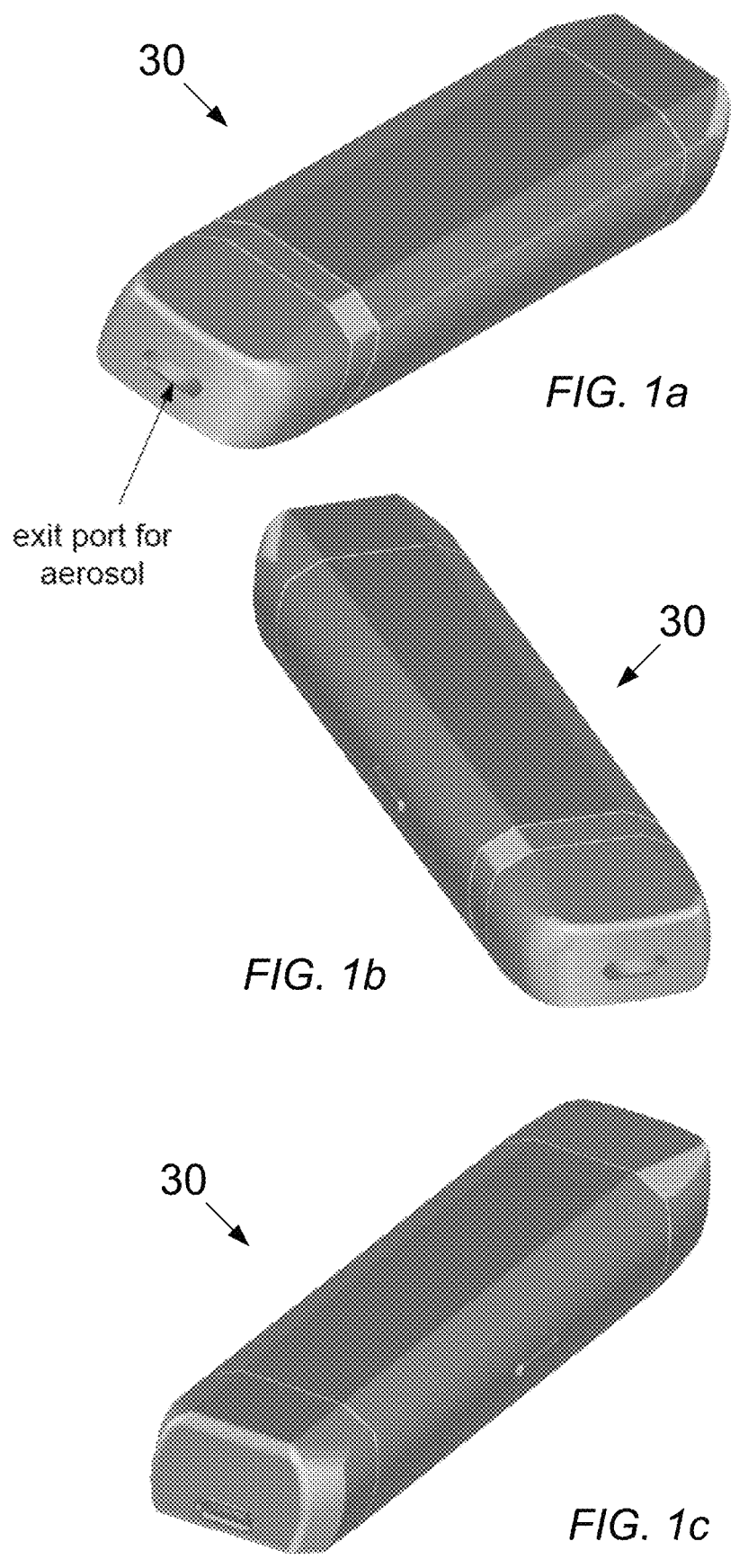

FIG. 1a is a solid, perspective view of an end of a second preferred embodiment of a vaporizer in accordance with one or more aspects and features of the invention.

FIG. 1b is another solid, perspective view of the vaporizer of FIG. 1a.

FIG. 1c is a solid, perspective view of an end of the vaporizer opposite to the end shown in FIGS. 1a and 1b.

FIG. 2a is a solid line drawing of the view seen in FIG. 1a.

FIG. 2b is a solid line drawing of the view seen in FIG. 1b.

FIG. 2c is a solid line drawing of the view seen in FIG. 1c.

FIG. 3a is a line drawing of the view seen in FIG. 1a.

FIG. 3b is a line drawing of the view seen in FIG. 1b.

FIG. 3c is a line drawing of the view seen in FIG. 1c.

FIG. 4b is another solid, perspective view of the end of the vaporizer of FIG. 4a.

FIG. 4c is another solid, perspective view of the end of the vaporizer of FIG. 4a.

FIG. 5a is a solid line drawing of the view seen in FIG. 4a.

FIG. 6a is a line drawing of the view seen in FIG. 4a.

FIG. 7b is a solid, plan view of a top end of the vaporizer of FIG. 4a.

FIG. 7c is a solid, plan view of the bottom end of the vaporizer of FIG. 4a.

FIG. 8a is a solid line drawing of the view seen in FIG. 7a.

FIG. 9a is a line drawing of the view seen in FIG. 7a.

FIG. 10a is a solid perspective view of the vaporizer of FIG. 4a.

FIG. 10b is another solid side view of the vaporizer of FIG. 4a.

FIG. 11a is a solid line drawing of the view seen in FIG. 10a.

FIG. 12a is a line drawing of the view seen in FIG. 10a.

As seen in FIG. 14a, the piezo mesh disk is received with a cartridge body.

FIG. 17b is a bottom plan view of the cartridge as seen in FIG. 17a.

FIG. 18b is an elevational front view of the vaporizer as seen in FIG. 18a.

FIG. 18c is an elevational first side view of the vaporizer as seen in FIG. 18a.

FIG. 18d is an elevational back view of the vaporizer as seen in FIG. 18a.

FIG. 18e is an elevational second side view of the vaporizer as seen in FIG. 18a.

FIG. 19a is a bottom perspective view of the bladder and mesh assembly, the cartridge mounting plate, and magnets by which the mounting plate is secured to the main body chassis.

FIG. 19b is a top perspective view of the bladder and mesh assembly, the cartridge mounting plate, and magnets of the cartridge seen in FIG. 19a.

FIG. 19c is a back perspective view of the bladder and the mesh assembly, the cartridge mounting plate, and magnets of the cartridge of FIG. 19a.

FIG. 19d is a perspective elevational view of the bladder and the mesh assembly, the cartridge mounting plate, and magnets of the cartridge of FIG. 19a.

FIG. 19e is another back perspective view of the bladder and the mesh assembly, the cartridge mounting plate, and magnets of the cartridge of FIG. 19a.

FIG. 19f is a back elevational view of the bladder and the mesh assembly, the cartridge mounting plate, and magnets of the cartridge of FIG. 19a.

FIG. 20a is a front perspective view of the bladder and the mesh assembly of FIG. 19a without the cartridge mounting plate and magnets.

FIG. 20b is a bottom perspective view of the bladder and the mesh assembly of FIG. 20a.

FIG. 20c is a back perspective view of the bladder and the mesh assembly of FIG. 20a.

FIG. 20d is a back perspective view of the mesh assembly of FIG. 20a without the bladder.

FIG. 20e is a back perspective view of the bladder of FIG. 20a without the mesh assembly.

FIG. 20f is a bottom plan view of the bladder of FIG. 20e.

FIG. 20g is a side elevational view of the bladder of FIG. 20e.

FIG. 20h is a bottom perspective view of the bladder of FIG. 20e.

FIG. 20i is a top plan view of the bladder of FIG. 20a.

FIG. 21a is a bottom perspective view of an alternative bladder secured to the cartridge mounting plate of FIG. 19a.

FIG. 21b is an exploded view of the alternative bladder and mounting plate of FIG. 21a.

FIG. 21c is yet another alternative bladder secured to the cartridge mounting plate of FIG. 19a, which view is a shaded line drawing.

FIG. 21d is a solid view of the view of FIG. 21c.

FIG. 22a is a top perspective view of another alternative bladder for use with the cartridge mounting plate of FIG. 19a.

FIG. 22b is a bottom perspective view of the bladder of FIG. 22a.

FIG. 22c is a top perspective view of another alternative bladder for use with the cartridge mounting plate of FIG. 19a.

FIG. 22e is a top perspective view of another alternative bladder for use with the cartridge mounting plate of FIG. 19a.

FIG. 23a is a top plan view of another alternative bladder for use with the cartridge mounting plate of FIG. 19a.

FIG. 23b is a bottom perspective view of the bladder of FIG. 23a.

FIG. 23c is a top plan view of another alternative bladder for use with the cartridge mounting plate of FIG. 19a.

FIG. 23d is a bottom perspective view of the bladder of FIG. 23c.

FIG. 23e is a top plan view of another alternative bladder for use with the cartridge mounting plate of FIG. 19a.

FIG. 23f is an elevational side view of the bladder of FIG. 23e.

FIG. 23g is a top plan view of another alternative bladder for use with the cartridge mounting plate of FIG. 19a.

FIG. 23h is a bottom perspective view of the bladder of FIG. 23g.

FIG. 24a is a wire frame illustration of a vaporizer illustrating in solid view use of the bladder of FIG. 21a.

FIG. 24b is a transparent, top perspective view of a cartridge body including mesh assembly illustrating in solid view use of the bladder of FIG. 21a.

FIG. 24c is a bottom perspective view of the cartridge of FIG. 24b.

FIG. 24d is a bottom perspective view of a cartridge illustrating in solid view use of the bladder of FIG. 21c.

FIG. 24e is a top perspective view of the cartridge of FIG. 24d.

FIG. 25a is a perspective view of an alternative cartridge for use with the vaporizer of FIG. 13 illustrating in solid view a piezoelectric material, mesh material, bladder, and a mechanism for driving fluid from the bladder to the mesh material for aerosolizing.

FIG. 25b is a perspective view of the other side of the cartridge of FIG. 25a.

FIG. 25c is a side elevational view of the cartridge of FIG. 25a.

FIG. 25d is a perspective view of an alternative cartridge for use with the vaporizer of FIG. 13 illustrating in solid view a piezoelectric material, mesh material, bladder, and a mechanism for driving fluid from the bladder to the mesh material for aerosolizing.

FIG. 25e is a view of the cartridge of FIG. 25d without the mechanism of FIG. 25d.

FIG. 25f is another view of the cartridge of FIG. 25e from a side opposite to the side of the view of FIG. 25e.

FIG. 26a is a top perspective view of an alternative cartridge for use with the vaporizer of FIG. 13 illustrating in solid view a piezoelectric material, mesh material, bladder, and a mechanism for driving fluid from the bladder to the mesh material for aerosolizing.

FIG. 26b is a bottom perspective view of the cartridge of FIG. 26a.

FIG. 26c is a top perspective view of an alternative cartridge for use with the vaporizer of FIG. 13 illustrating in solid view a piezoelectric material, mesh material, bladder, and a mechanism for driving fluid from the bladder to the mesh material for aerosolizing.

FIG. 26d is a bottom perspective view of yet another alternative cartridge for use with the vaporizer of FIG. 13 illustrating in solid view a piezoelectric material, mesh material, bladder, and a mechanism for driving fluid from the bladder to the mesh material for aerosolizing.

FIG. 26e is a top perspective view of the cartridge of FIG. 26d without the mechanism of FIG. 26d.

FIG. 26f is a top perspective view of yet another alternative cartridge for use with the vaporizer of FIG. 13 illustrating in solid view a piezoelectric material, mesh material, bladder, and a mechanism for driving fluid from the bladder to the mesh material for aerosolizing.

FIG. 27a is an elevational view of an alternative cartridge for use with the vaporizer of FIG. 13 illustrating in solid view a bladder thereof.

FIG. 27b is a top perspective view of the cartridge of FIG. 27a.

FIG. 27c is a bottom perspective view of the cartridge of FIG. 27a.

FIG. 27d is a bottom perspective view of yet another alternative cartridge for use with the vaporizer of FIG. 13 illustrating in solid view a bladder thereof which is similar to the bladder of FIG. 27a, but which includes a radial arm for side filling of liquid through injection.

FIG. 27e is a top perspective view of the cartridge of FIG. 27d.\

FIG. 28a is top perspective view of an alternative cartridge for use with the vaporizer of FIG. 13 illustrating in solid view a piezoelectric material, mesh material, and bladder thereof.

FIG. 28b is a bottom perspective view of the cartridge of FIG. 28a.

FIG. 28c is top perspective view of yet another alternative cartridge for use with the vaporizer of FIG. 13 illustrating in solid view a piezoelectric material, mesh material, and bladder thereof.

FIG. 28d is another top perspective view of the cartridge of FIG. 28c.

FIG. 28e is a bottom perspective view of the cartridge of FIG. 28c.

FIG. 29b is a bottom perspective view of the cartridge of FIG. 29a.

FIG. 30b is a bottom perspective view of the cartridge of FIG. 30a.

FIG. 31 additionally sets forth other potential means for causing the liquid to contact the mesh material, which are shown in contrast to gravity fed systems.

Figure 4A:
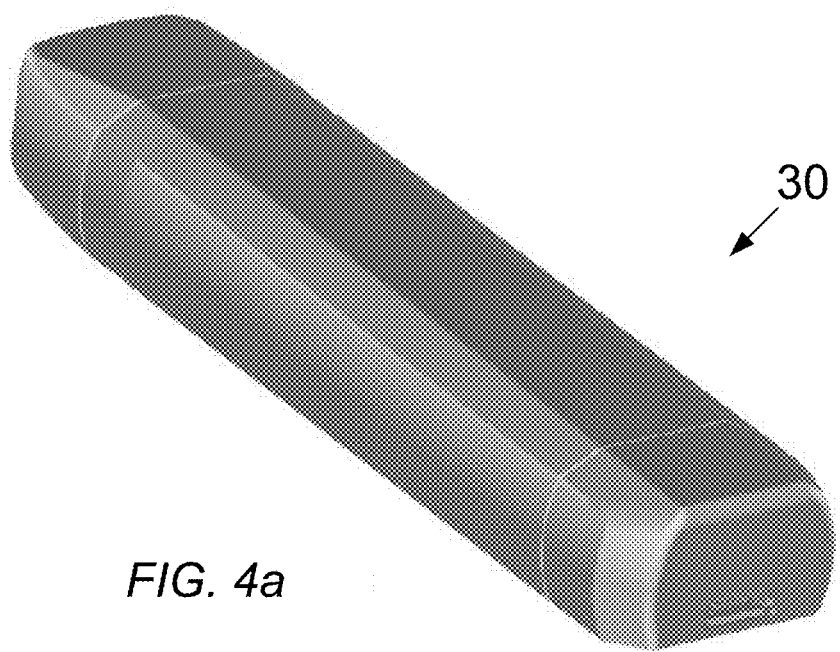
FIG. 4a is a solid, perspective view of the opposite end of the second preferred embodiment, which end is the subject of focus in FIG. 1c.
Figure 4B:
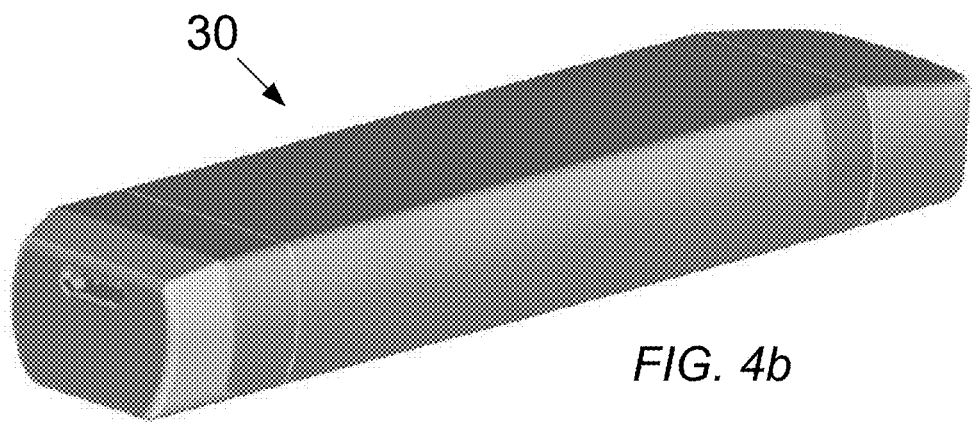
Figure 4C:
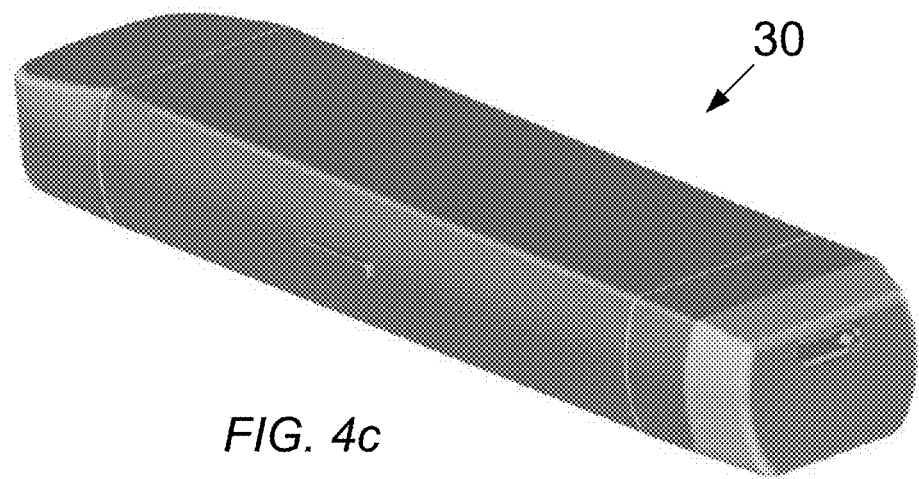
Figure 5A:
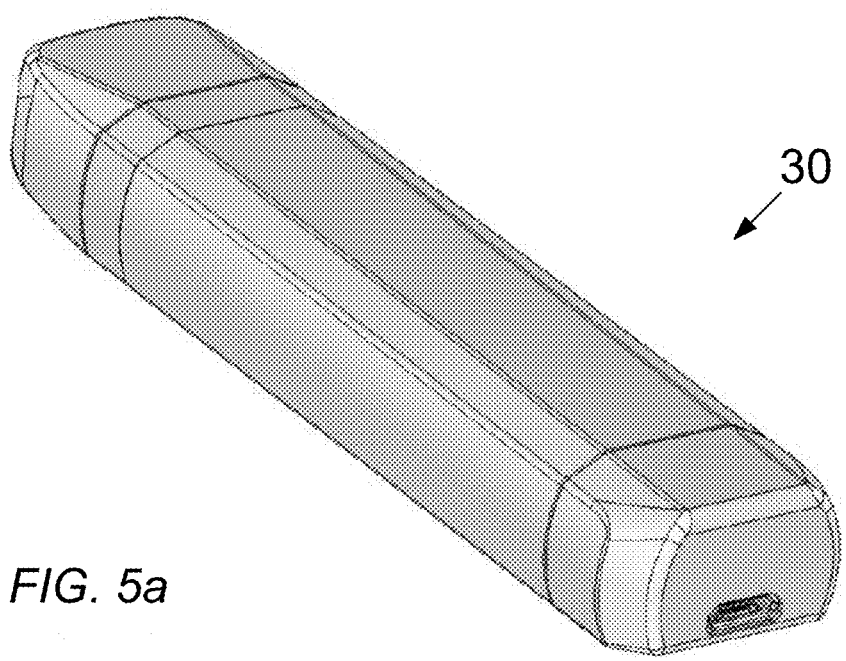
Figure 5B:
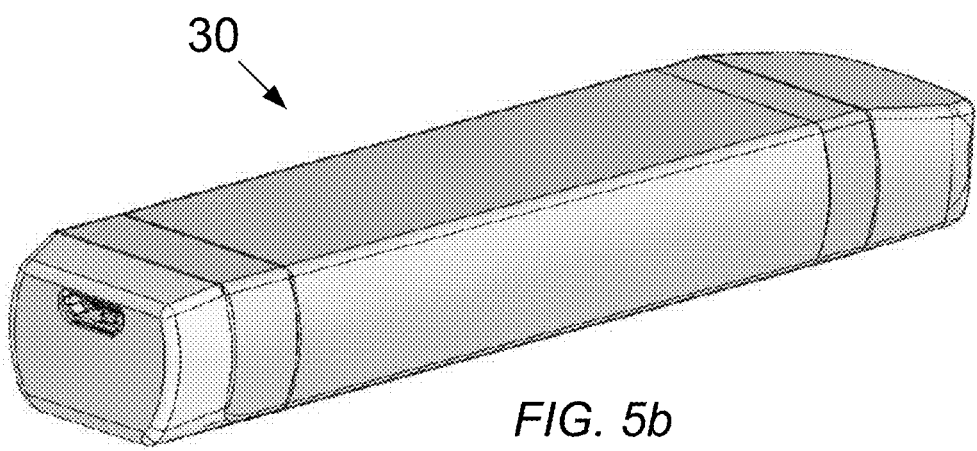
FIG. 5b is a solid line drawing of the view seen in FIG. 4b.
Figure 5C:
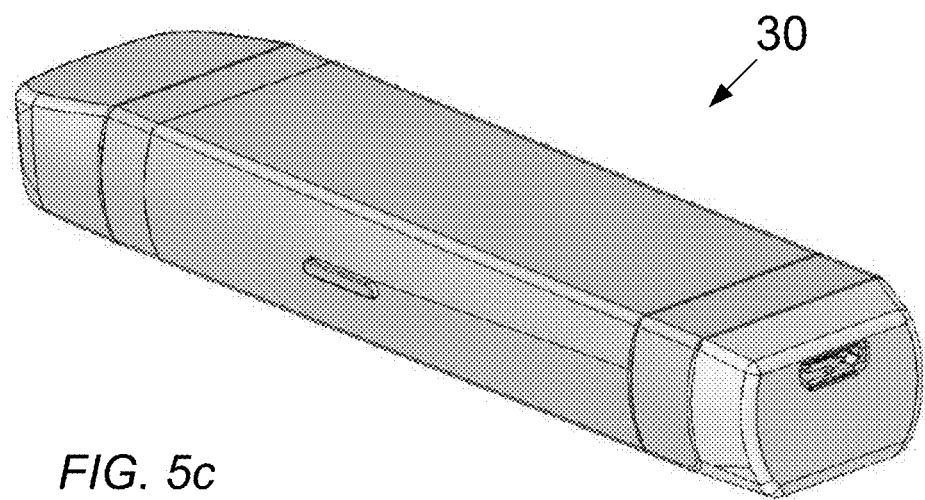
FIG. 5c is a solid line drawing of the view seen in FIG. 4c.
Figure 6A:
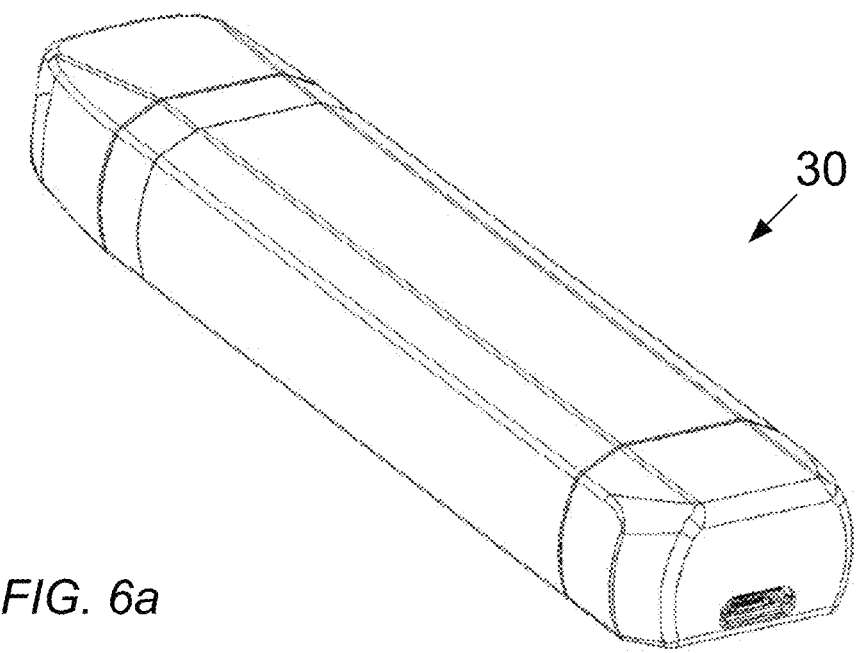
Figure 6B:
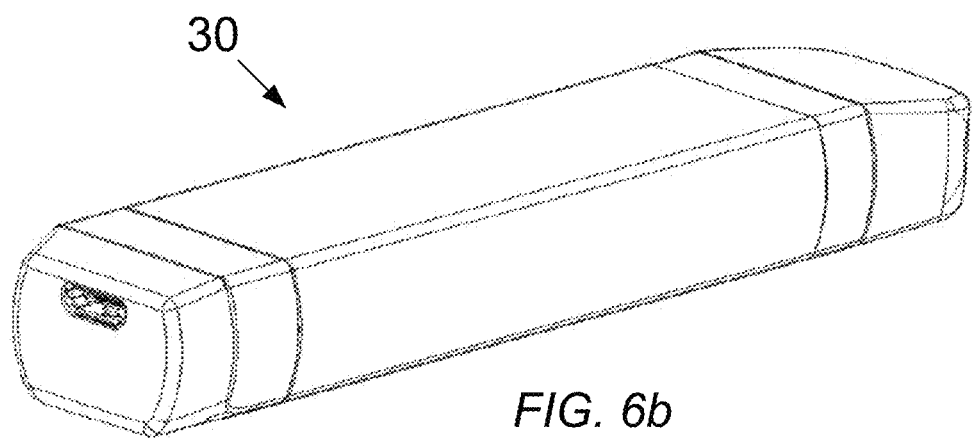
FIG. 6b is a line drawing of the view seen in FIG. 4b.
Figure 6C:
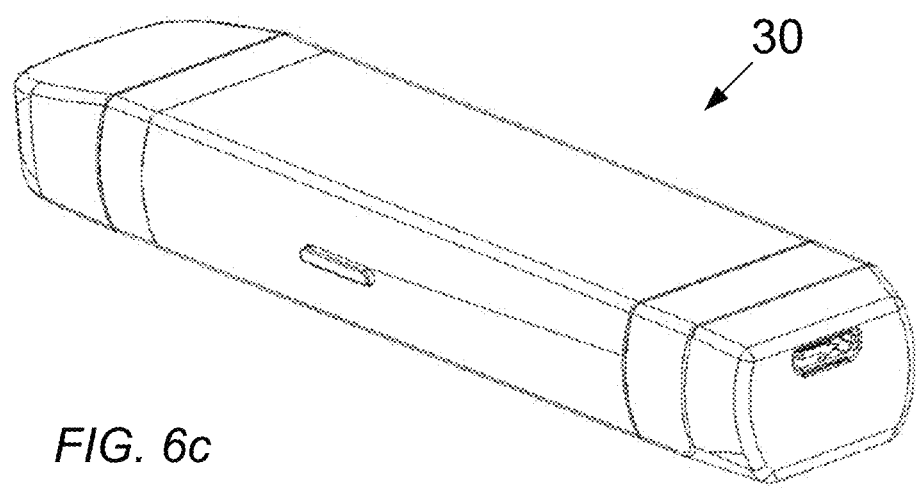
FIG. 6c is a line drawing of the view seen in FIG. 4c.
Figure 7A:
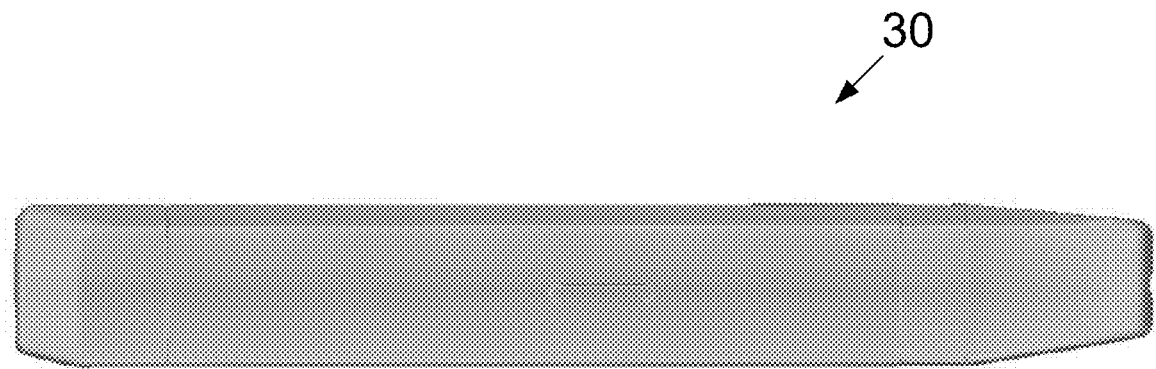
FIG. 7a is a solid, perspective view of a side of the vaporizer of FIG. 4a, which side includes the button.
Figure 7B:
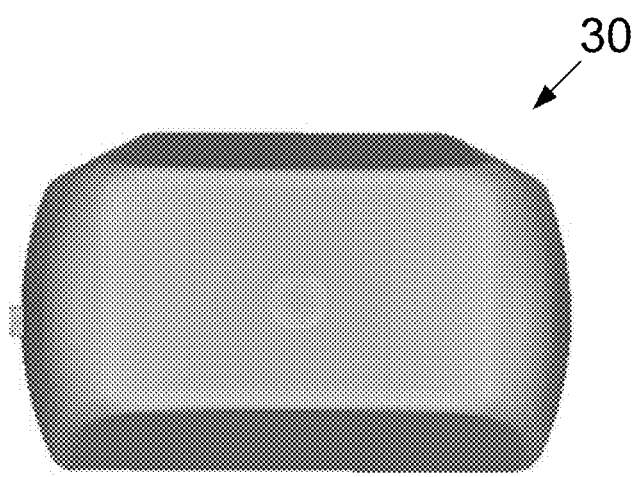
Figure 7C:
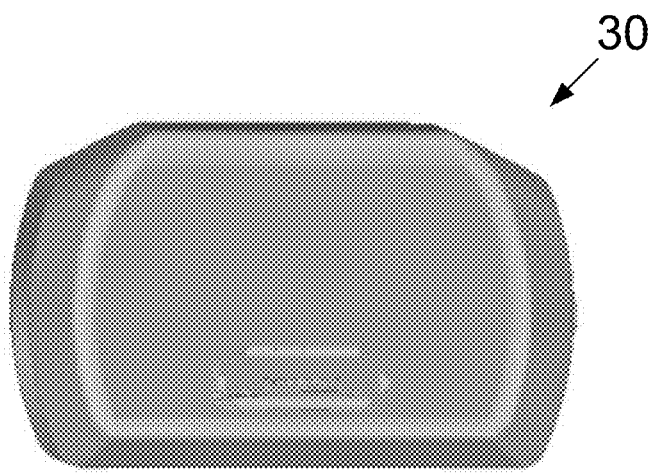
Figure 8A:
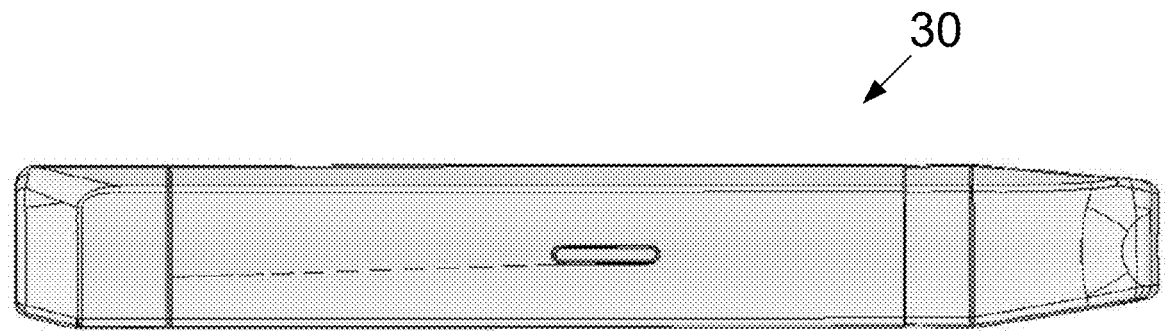
Figure 8B:
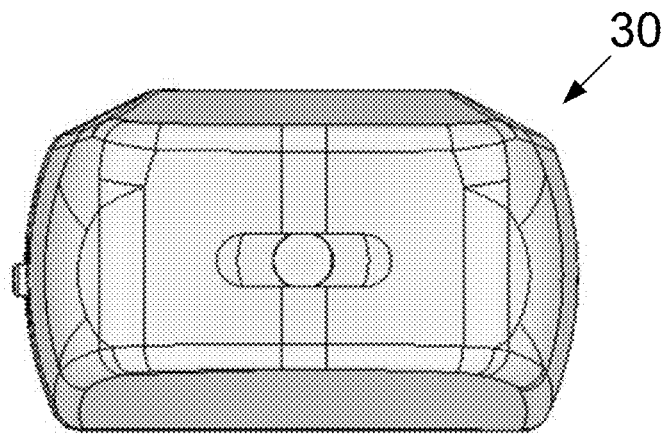
FIG. 8b is a solid line drawing of the view seen in FIG. 7b.
Figure 8C:
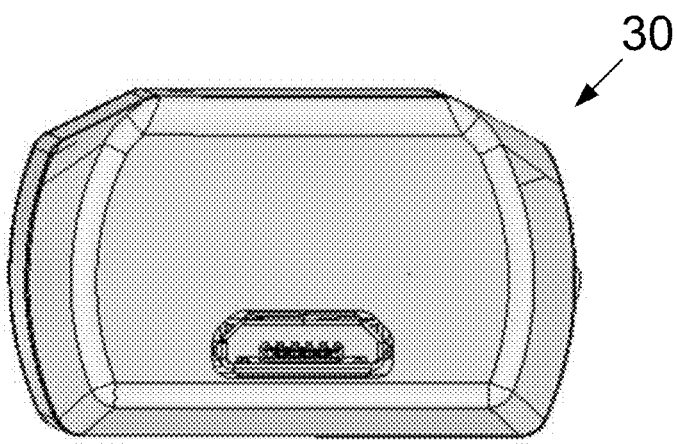
FIG. 8c is a solid line drawing of the view seen in FIG. 7c.
Figure 9A:
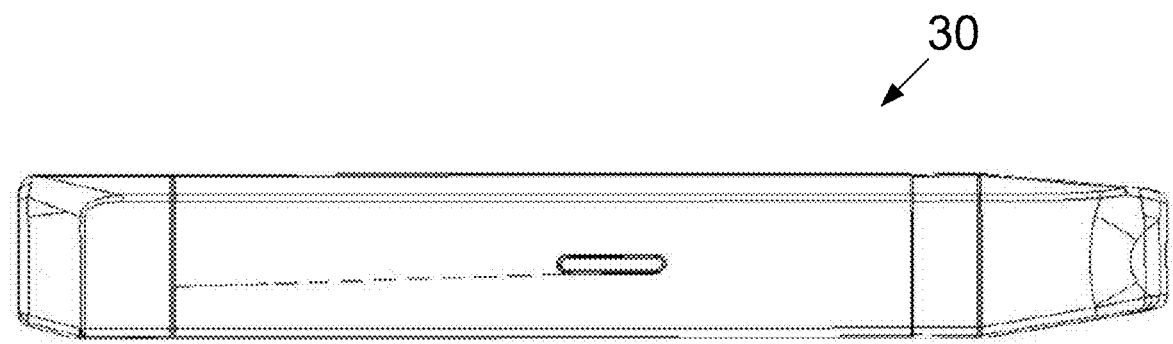
Figure 9B:
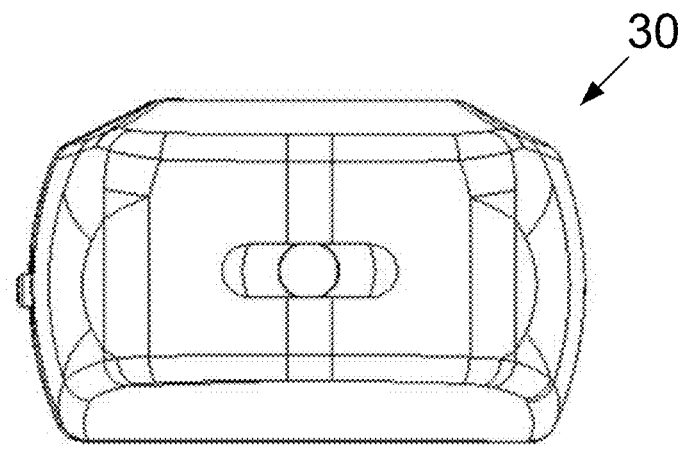
FIG. 9b is a line drawing of the view seen in FIG. 7b.
Figure 9C:
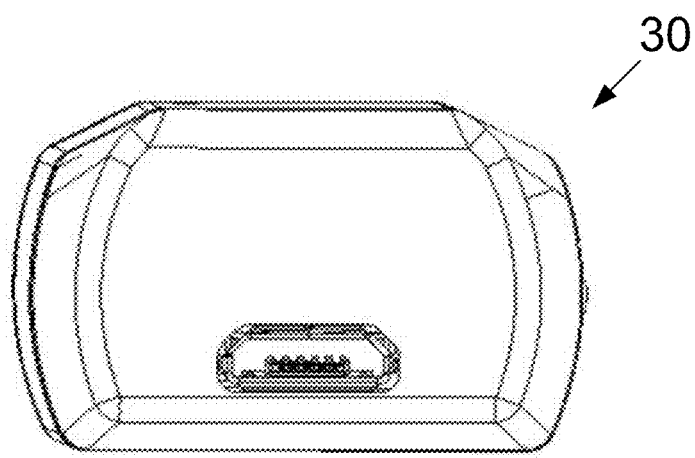
FIG. 9c is a line drawing of the view seen in FIG. 7c.

Additional views of many of these cartridges and bladders, and alternative thereof, are disclosed in files of the computer program listing incorporated herein by reference. These files present three-dimensional interactive views using an eDrawing viewer and an Acrobat viewer.

DETAILED DESCRIPTION

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Furthermore, an embodiment of the invention may incorporate only one or a plurality of the aspects of the invention disclosed herein; only one or a plurality of the features disclosed herein; or combination thereof. As such, many embodiments are implicitly disclosed herein and fall within the scope of what is regarded as the invention.

Accordingly, while the invention is described herein in detail in relation to one or more embodiments, it is to be understood that this disclosure is illustrative and exemplary of the invention and is made merely for the purposes of providing a full and enabling disclosure of the invention. The detailed disclosure herein of one or more embodiments is not intended, nor is to be construed, to limit the scope of patent protection afforded the invention in any claim of a patent issuing here from, which scope is to be defined by the claims and the equivalents thereof. It is not intended that the scope of patent protection afforded the invention be defined by reading into any claim a limitation found herein that does not explicitly appear in the claim itself Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

With regard to the construction of the scope of any claim in the United States, no claim element is to be interpreted under 35 U.S.C. 112(f) unless the explicit phrase "means for" or "step for" is actually used in such claim element, whereupon this statutory provision is intended to and should apply in the interpretation of such claim element. With regard to any method claim including a condition precedent step, such method requires the condition precedent to be met and the step to be performed at least once but not necessarily every time during performance of the claimed method.

Furthermore, it is important to note that, as used herein, "comprising" is open-ended insofar as that which follows such term is not exclusive. Additionally, "a" and "an" each generally denotes "at least one" but does not exclude a plurality unless the contextual use dictates otherwise. Thus, reference to "a picnic basket having an apple" is the same as "a picnic basket comprising an apple" and "a picnic basket including an apple", each of which identically describes "a picnic basket having at least one apple" as well as "a picnic basket having apples"; the picnic basket further may contain one or more other items beside an apple. In contrast, reference to "a picnic basket having a single apple" describes "a picnic basket having only one apple"; the picnic basket further may contain one or more other items beside an apple. In contrast, "a picnic basket consisting of an apple" has only a single item contained therein, i.e., one apple; the picnic basket contains no other item.

When used herein to join a list of items, "or" denotes "at least one of the items" but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers"; the picnic basket further may contain one or more other items beside cheese and crackers.

When used herein to join a list of items, "and" denotes "all of the items of the list". Thus, reference to "a picnic basket having cheese and crackers" describes "a picnic basket having cheese, wherein the picnic basket further has crackers", as well as describes "a picnic basket having crackers, wherein the picnic basket further has cheese"; the picnic basket further may contain one or more other items beside cheese and crackers.

The phrase "at least one" followed by a list of items joined by "and" denotes an item of the list but does not require every item of the list. Thus, "at least one of an apple and an orange" encompasses the following mutually exclusive scenarios: there is an apple but no orange; there is an orange but no apple; and there is both an apple and an orange. In these scenarios if there is an apple, there may be more than one apple, and if there is an orange, there may be more than one orange. Moreover, the phrase "one or more" followed by a list of items joined by "and" is the equivalent of "at least one" followed by the list of items joined by "and".

Additionally, as used herein unless context dictates otherwise, the following terms have the following meanings.

"Liquid" means a substance that flows freely but is of constant volume, generally having a consistency like that of water (lower viscosity) or oil (higher viscosity). Liquid is generic to and encompasses a solution, a suspension, and an emulsion.

"Solution" means a homogeneous mixture of two or more components. The dissolving agent is the solvent. The substance that is dissolved is the solute. The components of a solution are atoms, ions, or molecules, and the components are usually a nanometer or less in any dimension. An example of a solution is sugar mixed with water.

"Suspension" means a mixture of components that can be evenly distributed by mechanical methods such as shaking or stirring, but that will eventually settle out over an extended period of time. The components in a suspension are generally larger than those in solutions. An example of a suspension is oil mixed with water.

"Colloidal dispersion" means a heterogenous liquid mixture in which a component is dispersed in another component and does not tend to settle out over an extended period of time. The dispersed components generally is larger than components of a solution and smaller than components of a suspension.

"Aerosol" means a colloidal dispersion of a solid or liquid in a gas.

"Emulsion" means a colloidal dispersion of a liquid in a liquid. An example of an emulsion is milk.

"Nanoemulsion" means an emulsion in which the dispersed component comprises nanoparticles.

"Nanoparticle" means a molecule has—or aggregate of molecules have—having no dimension greater than about a micrometer (1,000 nanometers). In accordance with preferred embodiments of aspects and features of the invention, nanoparticles preferably have a dimension of between about 50 and about 200 nanometers.

"Micelle" means a vesicle having a layer of molecules that encapsulate and transport a substance to cells of a body. The encapsulating molecules in a micelle may be surfactants or polymers, for example. A typical micelle in an aqueous solution forms an aggregate with the hydrophilic "head" regions in contact with the surrounding solvent, creating a hydrophobic tail region in the interior of the aggregate.

"Liposome" means a vesicle having at least one bilayer of molecules that encapsulates and transports a substance to cells of a body.

"Microfluidizing machine" means an apparatus that uses microreactor technology to make nanoemulsions through the interaction of liquid streams in defined microchannels. Such technology is described, for example, in U.S. patent application publications 2012/0236680 and 2019/0299171, each incorporated herein by reference. Microfluidizing machines principally utilize high shear forces and impact to emulsify a liquid-liquid system, dispersing one immiscible liquid into another within an interaction chamber. A "Y" chamber preferably is used and may be single-slotted or multi-slotted. Fundamentally, such microreactor technology comprises a large pump that forces a formulation through a very small orifice (i.e., microchannel) at pressures ranging from as low as 3.4 MPa (500 psi) to as high as 275 MPa (40,000 psi). Preferred microfluidizing machines correspond to the processors manufactured, sold, or distributed by Mircofluidics of Newton or Westwood, Massachusetts, under the registered trademark MICROFLUIDIZER, and any and all other apparatus that have the same or equivalent structure for performing the same or equivalent function with the same or equivalent result. The appendix includes a user guide from 2014 for MICROFLUIDIZER processors distributed by Microfluidics, which appendix is incorporated herein by reference.

Referring now to the drawings, as well as to the drawings of the incorporated disclosures of Applicant's other applications, and any U.S. patent application publications thereof and U.S. patents issuing therefrom, one or more preferred embodiments in accordance with one or more aspects and features of the invention are next described. The following description of one or more preferred embodiments is merely exemplary in nature and is in no way intended to limit the invention, its implementations, or uses.

In accordance with electronic devices of the invention, a vibrating mesh is provided for aerosolizing a liquid without smoldering. The aerosolized liquid preferably is in the form of a vapor cloud similar to what a person or observer would surmise to be "vapor" when vaping. In the context of vaping, such preferred devices of the invention therefore are believed to produce an aerosol that is carcinogen free. This is in stark contrast to vaporizers used today to aerosolize e-liquids by heating the e-liquids and desired compounds contained therein (e.g., nicotine) or supplements such as B12, THC/CBD and other drugs or stimulants. As a result of using heating to aerosolize the e-liquids, these vaporizers produce toxic byproducts like formaldehyde, a recognized Group 1 carcinogen for caner, which toxic byproducts then are unfortunately inhaled by a person using the vaporizer. For example, when the liquids are heated, the liquids undergo a thermochemical reaction producing unwanted emissions. The unwanted emissions of the toxic byproducts may cause bodily harm from extended inhalation exposure.

By utilizing a vibrating mesh, preferred electronic devices in accordance with one or more aspects and features of the invention produce an aerosol without using heat and thus advantageously avoid such toxic byproducts created by the vaporizes currently on the market. The electronic devices thereby advantageously produce a carcinogen free aerosol free of harmful emission byproducts.

One of the primary performance metrics evaluated for aerosols is the residual aerodynamic particle size distribution ("APSD") of the aerosolized drug product. The residual APSD is characterized by the residual mass median aerodynamic diameter ("MMAD") and the geometric standard deviation ("GSD"). The MMAD signifies the aerodynamic diameter at which half of the aerosolized drug mass lies below the stated diameter.

The $MMADR=MMDI \times pI \times CNV 1/3 \times pR\ 1/6$, where $MMADR$ ($\mu m$) 1s the mass median aerodynamic diameter of the residual particles, $MMDI$ ($\mu m$) is the mass median diameter (MMD) of the initial droplets, CNV (weight fraction) is the concentration of the non-volatile components (e.g., dissolved drug and excipients) in the formulation, and $pI$ and $pR$ are the densities (g/cm3) of the formulation and the residual particles, respectively.

The vibrating mesh may be configured and arranged to produce an aerosol for various applications. For example, the arrangement and geometry of various features of the vibrating mesh, such as the design of the vibrating mesh and more specifically the design of the aperture holes of the vibrating mesh, may be adapted to produce an aerosol with various particle sizes, flow properties, and fine particle fractions. The size (e.g., diameter), shape (e.g., oval, circular, triangular, etc.), spacing (e.g., distance between aperture holes, aperture hole density), etc. of the aperture holes may be configured and modified to adjust the size of the aerosol particles for specific applications. Additionally, the thickness of the mesh, especially when in the form of a plate, may also be configured to optimize aerosol properties. For example, the thickness of the plate may impart different properties and characteristics to the aerosol. Depending on the thickness of the plate, the holes may taper with a chamfer such that the entrance and/or exit diameter is larger than the bore diameter of the aperture hole. In another example, the aperture holes may have a constant diameter without a taper.

In another example, the rigidity of the mesh assembly may be configured to prevent oscillations of varying amplitude across the surface of the mesh, which could result in inconsistent aerosolization performance. For example, the thickness, geometry, and material selection for the vibrating mesh material may enhance the rigidity to prevent unwanted oscillations thereof. In some embodiments, the mesh material may be constructed from a metal alloy, to provide adequate rigidity, mass, durability and inert chemical properties for the aerosolization of different drug formulations. Indeed, the design and dimensions of the mesh material may be selected to optimize the device based on the intended application or use case. For example, the vibrating mesh may be configured to adjust the MMADR, fine particle fraction, air/particle velocity, etc. Additionally, the mesh material may also determine the resulting particle properties such as volume diameter, bulk density, tap density, shape, charge, etc.

In addition to the mechanical aspects of the mesh material and its operation, it is believed that the material substrate from which the mesh is constructed and the way in which the holes are generated have important implications for the aerosolization of different drug formulations. In some embodiments, the aperture holes may be electro formed or laser formed. It should be appreciated that other manufacturing methods may be used to form the aperture holes. Example methods for mesh production include electroplating and laser cutting, which may be used to produce a tapered hole. A tapered hole may optimize mesh performance by amplifying flow at the nozzle while reducing viscose losses. The electroplating method makes use of a lithographic plate and the eventual size of the mesh holes may be determined by the duration of the electroplating process. The holes become smaller as the metal is deposited on the edge of the hole over time. Laser cutting involves the use of a laser beam to cut the mesh holes into a thin sheet of metal or polymer material. Laser cutting metal may result in molten material being deposited around the hole, which may be removed by polishing.

In some embodiments, the liquid delivery system may be adapted for a specific liquid. For example, viscosity may be a controlling variable in the size of the aperture holes of the vibrating mesh. Some preferred liquids comprise nicotine, which is less viscous than a cannabinoid derivative (e.g., tetrahydrocannabinol ("THC") and cannabidiol ("CBD")), which has a higher viscosity. Other considerations may include water solubility, surface tension, acidity and/or basicity, and whether the liquid contains a liquid carrier. Some preferred liquids indeed comprise liquid carriers and, in particular, liposomal carriers. Various liquids and formulations may be used to form aerosols from electronic devices of the invention. These formulations may have widely different physiochemical properties, such as surface tension, density, viscosity, characteristics of intramolecular forces within the formulation and whether the formulation is a pure liquid or a suspension of particles within a liquid. Each of the above-mentioned physiochemical properties may affect the functionality, consistency, efficacy, and end properties of the resulting aerosol or vapor cloud.

The liquid delivery system also may be designed to provide different flow rates. For example, the pump may be an active pump or a passive pump. Additionally, in some preferred embodiments the output rate, pressure supplied by the pump, or both, may be adjusted to provide different flow rates.

In some embodiments, the geometry of the mesh may be the form of a dome-like structure. In some embodiments, the mesh may be flat and may be in the form of a plate. Other orientations and geometries also are contemplated within the scope of the invention.

Additionally, in electronic devices of the invention, the vibrating mesh assembly may include a single layer oscillating piezoelectric material to aerosolize the liquid. In an example, the mesh assembly may have a double or multi-layer structure, and multiple mesh membranes may be arranged to induce an optimum MMAD and/or APSD for the aerosolized liquid. A plurality of vibrating meshes also may be used in the mesh assembly in some embodiments.

Additionally, the mesh assembly may be constructed from one or more different piezoelectric materials to optimize the MMAD and/or APSD.

Additionally, the arrangement and design of the mesh assembly (e.g., placement of the holes, angstrom size) and hygroscopic effects of the lungs may be considered for optimum deposition and diffusion into the bloodstream.

In some embodiments, the electronic device is configured to create a fine particle low velocity aerosol. The resulting aerosol or vapor cloud may be configured to reduce or soften the potential irritation of the airways and lungs. In some embodiments, the encapsulation techniques may create the ideal personal experience. As mentioned above, the lungs have clearance mechanisms to prevent invasion of unwanted airborne particles from entering the body. To ensure that the fine particle, low velocity aerosol that achieves central and deep lung deposition, the electronic device and/or formulation may be adapted such that an aerosol is produced that eludes the lung's various lines of defense.

For example, progressive branching and narrowing of the airways encourage impaction of particles. Larger the particle sizes, greater velocities of incoming air, and more abrupt bend angles of bifurcations and the smaller the airway radius increase the probability of deposition by impaction. In essence, the end person may sense/feel more or less impaction based on the above parameters.

Additionally, the lung has a relative humidity of approximately 99.5%. The addition and removal of water can significantly affect the particle size of a hygroscopic aerosol and thus deposition itself. Drug particles are known to be hygroscopic and grow or shrink in size in high humidity, such as in the lung. A hygroscopic aerosol that is delivered at relatively low temperature and humidity into one of high humidity and temperature may increase in size when inhaled into the lung. For example, the rate of growth may be a function of the initial diameter of the particle. As it relates to size and diameter, particles may be deposited by inertial impaction, gravitational sedimentation or diffusion (Brownian motion) depending on their size. While deposition occurs throughout the airways, inertial impaction usually occurs in the first ten generations of the lung, where air velocity is high and airflow is turbulent.

In the therapeutic/medical environment, most particles larger than 10 micrometers are deposited in the oropharyngeal region with a large amount impacting on the larynx, particularly when the drug is inhaled from devices requiring a high inspiratory flow rate (e.g., as with dry powder inhalers ("DPIs")) or when the drug is dispensed from a device at a high forward velocity. The large particles are subsequently swallowed and contribute minimally, if at all, to the therapeutic response. In the tracheobronchial region, inertial impaction may also play a significant role in the deposition of particles, particularly at bends and airway bifurcations. Deposition by gravitational sedimentation may typically predominate in the last five to six generations of airways (smaller bronchi and bronchioles), where air velocity is low. Due to the low velocity, large volume aerosol that is produced in accordance with preferred embodiments of the invention, the aerosol may be less irritating to a person.

In the alveolar region, air velocity is typically negligible, and thus the contribution to deposition by inertial impaction is typically nonexistent. Particles in this region may have a longer residence time and may be deposited by both sedimentation and diffusion. Particles not deposited during inhalation may be exhaled. Deposition due to sedimentation affects particles down to 0.5 micrometers in diameter, whereas below 0.5 micrometers, the main mechanism for deposition is by diffusion.

Targeting the aerosol to conducting or peripheral airways may be accomplished by altering the particle size of the aerosol and/or the inspiratory flow rate. For example, aerosols with a MMAD of approximately 5 micrometers to 10 micrometers may be deposited in the large conducting airways and oropharyngeal region. Particles ranging from approximately 1 micrometer to 5 micrometers in diameter may be deposited in the small airways and alveoli with more than 50% of the particles having a diameter of three micrometers being deposited in the alveolar region.

In some embodiments, the electronic device includes a piezoelectric crystal that vibrates at a high frequency when electrical current is applied. In some embodiments, the vibration may be in the range of 0.5 to 5.0 MHz, and more specifically within the range of 1.2 to 2.4 MHz. The vibration of the crystal is transmitted to a transducer horn that is in contact with the liquid to be aerosolized. Vibrations transmitted by the transducer horn cause upward and downward movement of a mesh in the form, for example, of a plate, and the liquid passes through the apertures in the mesh plate to form an aerosol. In some embodiments, the mesh plate consists of a plurality of tapered holes (e.g., 500 holes; 1,000 holes; 6,000 holes). Each tapered hole may have a diameter of approximately 3 micrometers. In other examples, larger or smaller diameters may be appropriate for different liquids or applications. The aperture holes advantageously amplify the vibration of the transducer horn throughout the liquid and reduce the amount of power required to generate the aerosol. For example, using a low frequency of vibration with a mesh plate containing numerous minute holes allows efficient generation of a fine particle mist.

In some embodiments, aqueous liquids may be more suitable to generating an aerosol with electronic devices of the invention when compared to other more viscous liquids. In some embodiments, the aqueous liquids may include ethanol, which itself may be a primary liquid carrier of the liquid.

Additionally, in some preferred embodiments ultrasonicated a liposomal nanoemulsions comprises the liquid carrier of the liquid delivery system. Nanoemulsions may be sonicated where liposomes work as carriers for active agents. In some embodiments, liposomes may be prepared and formed (e.g., by ultrasound) for the entrapment of active agents. In some instances, emulsifiers are added to the liposomal dispersions to stabilize higher amounts of lipids; however, additional emulsifiers may cause a weakening on the barrier affinity of a liquid (e.g., phosphatidylcholine). Nanoparticles (e.g., nanoparticles composed of phosphatidylcholine and lipids) preferably are used to solve this. Thus, in some embodiments, nanoparticles are used that preferably are formed by an oil droplet that is covered by a monolayer of phosphatidylcholine. It is believed that the use of nanoparticles allows formulations which are capable of absorbing more lipids and which remain stable whereby additional emulsifiers may not be needed.

As discussed above, ultrasonication is a method for the production of nanoemulsions and nanodispersions. In some embodiments, an intensive ultrasound supplies the power needed to disperse a liquid phase (dispersed phase) in small droplets in a second phase (continuous phase). In the dispersing zone, imploding cavitation bubbles cause intensive shock waves in the surrounding liquid and result in the formation of liquid jets of high liquid velocity. In order to stabilize the newly formed droplets of the disperse phase against coalescence, emulsifiers (surface active substances, surfactants) and stabilizers are added to the emulsion. As coalescence of the droplets after disruption influences the final droplet size distribution, efficiently stabilizing emulsifiers may be used to maintain the final droplet size distribution at a level that is equal to the distribution immediately after the droplet disruption in the ultrasonic dispersing zone.

Some liposomal dispersions (e.g., those based on unsaturated phosphatidylcholine) may lack in stability against oxidation. The stabilization of the dispersion can be achieved by antioxidants, such as by a complex of vitamins C and E. For example, the entrapment of the essential oil in liposomes may increase the oil stability.

Figure 10A:
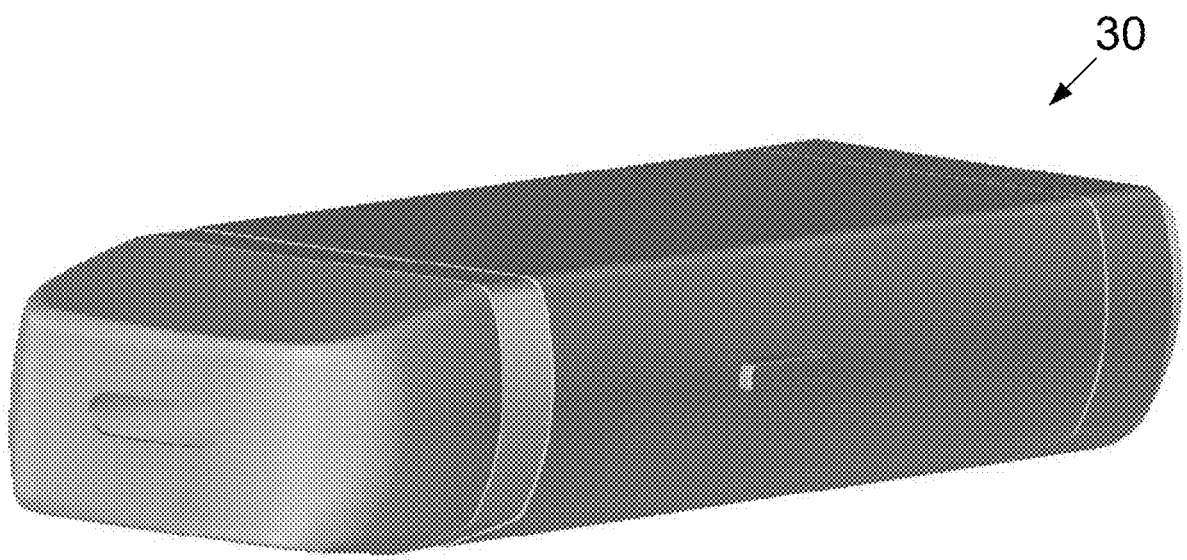
Figure 10B:
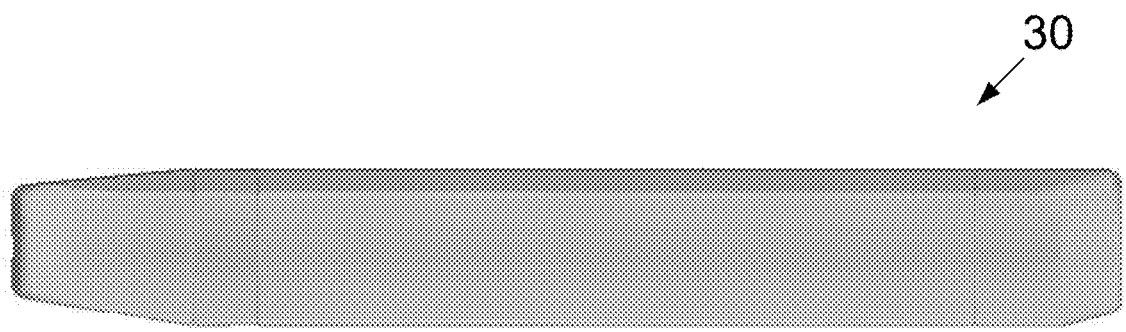
Figure 11A:
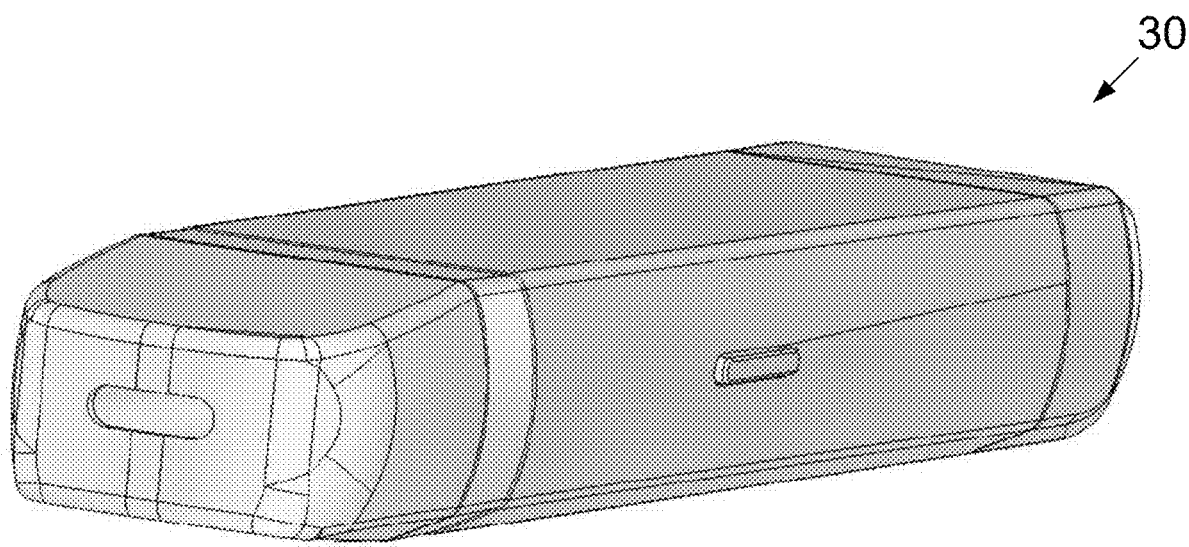
Figure 11B:
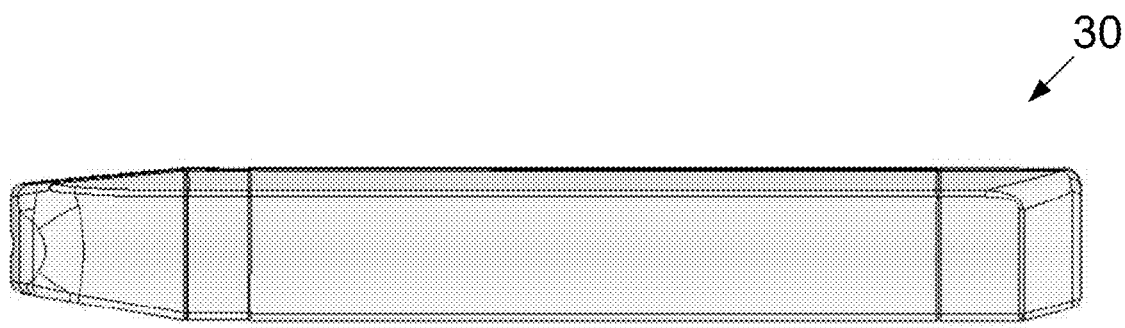
FIG. 11b is a solid line drawing of the view seen in FIG. 10b.
Figure 12A:
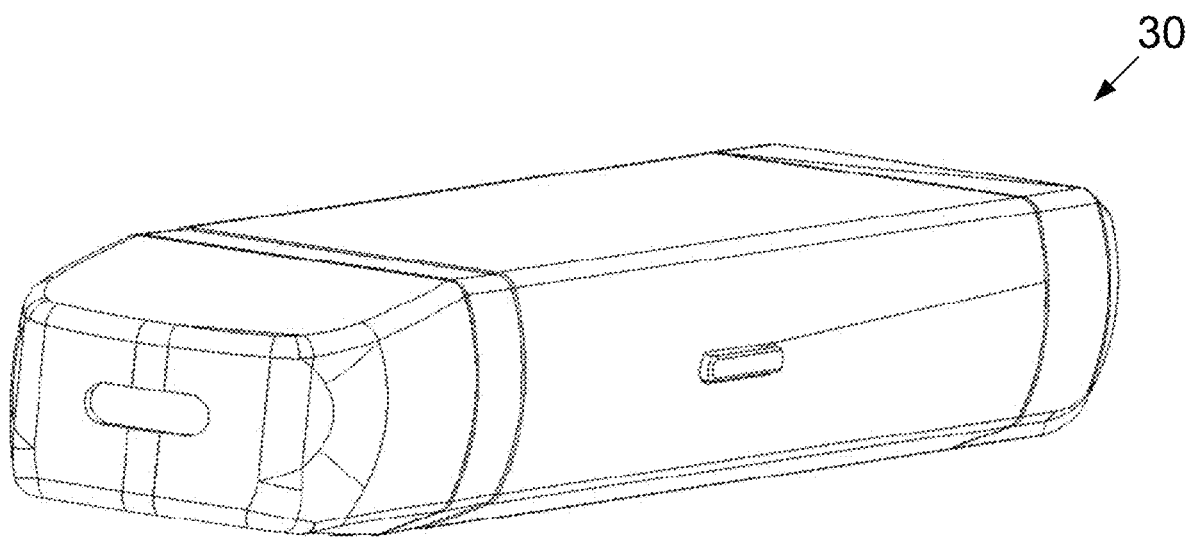
Figure 12B:
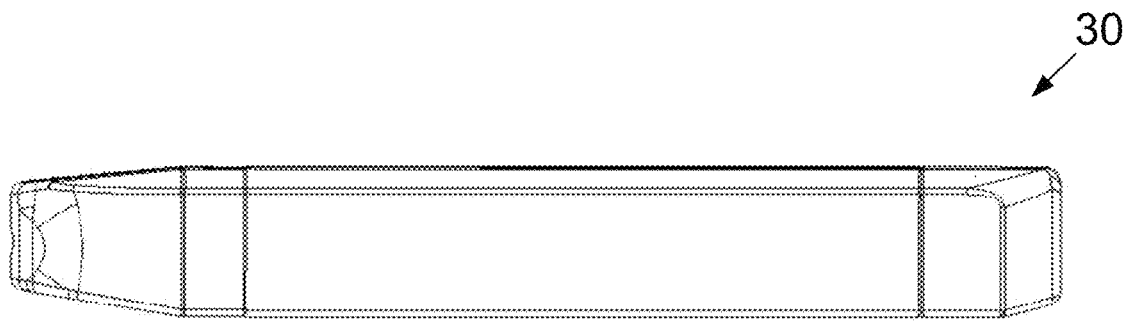
FIG. 12b is a line drawing of the view seen in FIG. 10b.

In some embodiments, the vibrating mesh is configured to create a fine particle low velocity aerosol which is well suited for central and deep lung deposition. By producing a fine particle, low velocity aerosol, one or more preferred electronic devices of the invention advantageously can produce an aerosol that is adapted to target small airways in the management of asthma and COPD.

Additionally, some embodiments, a pump system is utilized to pump or push the liquid to be aerosolized into contact with the vibrating mesh whereby droplets of the liquid are created on the other side of the vibrating mesh on the order of 1 to 4 microns. While it is contemplated that a capillary pump may be used (wherein the liquid is drawn into contact with the mesh material through capillary action), electronic devices of the invention also may preferably comprise a pump system that is powered by an electrical power source of the device, such as batteries and, preferably, rechargeable batteries. Such a pump system preferably comprises a piezoelectric motor. In some embodiments, however, an active pump system is not used, and the liquid may be gravity-fed to a vibrating mesh or other vibrating structure. Thus, a gravitational pump may be used in such embodiments. This is particularly contemplated when an electronic device of the invention is used in a generally upright position as a nebulizer for drug delivery. In most preferred embodiments, however, the electronic device is orientation-agnostic and generally works as intended in any orientation relative to the directional forces of gravity.

Turning now to drawings, in FIGS. 1-8 of the '005 Publication, a preferred embodiment of an electronic device in the form of a "vaporizer" is illustrated in accordance with one or more aspect and features of the invention. Other forms of an electronic device in accordance with the present include vapes, vape pens, and nebulizers. Other terminology may be given to electronic devices of the present invention. In any event, electronic devices of the present invention produce an aerosol for inhalation whatever commercial or consumer name may be given.

Specifically, FIG. 1 of the '005 Publication is a perspective view of a preferred embodiment of a vaporizer 10 in accordance with one or more aspect and features of the invention; FIG. 2 of the '005 Publication is a partial view of the vaporizer 10 of FIG. 1 of the '005 Publication showing in closeup a counter, battery indicator, and mouthpiece thereof; FIG. 3 of the '005 Publication is another perspective view of the vaporizer 10 of FIG. 1 of the '005 Publication; FIG. 4 of the '005 Publication is still yet another perspective view of the vaporizer 10 of FIG. 1 of the '005 Publication; FIG. 5 of the '005 Publication is a perspective view of the other side of the vaporizer 10 seen in FIG. 1 of the '005 Publication; FIG. 6 of the '005 Publication is a perspective view of one of two opposite ends of the vaporizer 10 of FIG. 1 of the '005 Publication, which illustrated end comprises the mouthpiece 12 of the vaporizer; and FIG. 7 of the '005 Publication is an exploded view of the vaporizer 10 of FIG. 1 of the '005 Publication. The bladder 14 can be seen illustrated in blue with the piezo mesh disk 16 and electrical contacts 18 attached to form the mesh assembly 20. The mesh assembly is retained within a body of the cartridge 22, which cartridge is seen to have a perforated band in FIG. 7 of the '005 Publication.

Furthermore, FIG. 8 of the '005 Publication is a vapor cloud that is produced by a push of the button of the vaporizer 10 of FIG. 1 of the '005 Publication, which vapor cloud preferably has a known quantity of the substance to be inhaled per push of the button/aerosolizing cycle of the vaporizer.

Another preferred embodiment of an electronic device in the form of a vaporizer 30 is illustrated in FIGS. 1*a*-12*b*. Specifically, FIG. 1*a* is a solid, perspective view of an end of a second preferred embodiment of a vaporizer in accordance with one or more aspects and features of the invention; FIG. 1*b* is another solid, perspective view of the vaporizer of FIG. 1*a*; FIG. 1*c* is a solid, perspective view of an end of the vaporizer opposite to the end shown in FIGS. 1*a* and 1*b*; FIG. 2*a* is a solid line drawing of the view seen in FIG. 1*a*; FIG. 2*b* is a solid line drawing of the view seen in FIG. 1*b*; FIG. 2*c* is a solid line drawing of the view seen in FIG. 1*c*; FIG. 3*a* is a line drawing of the view seen in FIG. 1*a*; FIG. 3*b* is a line drawing of the view seen in FIG. 1*b*; FIG. 3*c* is a line drawing of the view seen in FIG. 1*c*; FIG. 4*a* is a solid, perspective view of the opposite end of the second preferred embodiment, which end is the subject of focus in FIG. 1*c*; FIG. 4*b* is another solid, perspective view of the end of the vaporizer of FIG. 4*a*; FIG. 4*c* is another solid, perspective view of the end of the vaporizer of FIG. 4*a*; FIG. 5*a* is a solid line drawing of the view seen in FIG. 4*a*; FIG. 5*b* is a solid line drawing of the view seen in FIG. 4*b*; FIG. 5*c* is a solid line drawing of the view seen in FIG. 4*c*; FIG. 6*a* is a line drawing of the view seen in FIG. 4*a*; FIG. 6*b* is a line drawing of the view seen in FIG. 4*b*; FIG. 6*c* is a line drawing of the view seen in FIG. 4*c*; FIG. 7*a* is a solid, perspective view of a side of the vaporizer of FIG. 4*a*, which side includes the button; FIG. 7*b* is a solid, plan view of a top end of the vaporizer of FIG. 4*a*; FIG. 7*c* is a solid, plan view of the bottom end of the vaporizer of FIG. 4*a*; FIG. 8*a* is a solid line drawing of the view seen in FIG. 7*a*; FIG. 8*b* is a solid line drawing of the view seen in FIG. 7*b*; FIG. 8*c* is a solid line drawing of the view seen in FIG. 7*c*; FIG. 8*a* is a line drawing of the view seen in FIG. 8*a*; FIG. 9*b* is a line drawing of the view seen in FIG. 7*b*; FIG. 9*c* is a line drawing of the view seen in FIG. 7*c*; FIG. 10*a* is a solid perspective view of the vaporizer of FIG. 4*a*; FIG. 10*b* is another solid side view of the vaporizer of FIG. 4*a*; FIG. 11*a* is a solid line drawing of the view seen in FIG. 10*a*;

FIG. 11b is a solid line drawing of the view seen in FIG. 10b; FIG. 12a is a line drawing of the view seen in FIG. 10a; and FIG. 12b is a line drawing of the view seen in FIG. 10b.

FIGS. 21a-21c of the '005 Publication collectively illustrate filling of a bladder 32 of the cartridge after the bladder has been installed in the cartridge by injecting fluid directly into the bladder using a needle 34 of an injector 36. Thereafter, the cartridge is secured to the main body chassis 38 of the vaporizer, as illustrated in FIGS. 21d-21i of the '005 Publication. This may be accomplished by an end-user when replacing a depleted cartridge with a new cartridge included in a pack of disposable cartridges purchased by the user, or during assembly of a vaporizer for sale to a user during manufacture and assembly of the vaporizer. The injection site when filling the bladder preferably is at a distal end of the bladder relative to a mouth of the bladder where a liquid is maintained in contact with the mesh material; however, alternative injection sites are contemplated. Indeed, the bladder of FIGS. 27d and 27e includes a radial arm by which the bladder is filled from a side of the bladder rather than bottom of the bladder.

FIGS. 21d-21i of the '005 Publication collectively illustrate mounting of the cartridge to a base of the vaporizer of FIGS. 1-8 of the '005 Publication.

FIG. 22 of the '005 Publication is a perspective view of a preferred embodiment of a self-healing, silicone bladder 40 after injection molding thereof in accordance with one or more aspects and features of the invention. The bladder of FIG. 22 of the '005 Publication has a capacity of about 2.5 milliliters. In other embodiments, the volume of the bladder is as much as 0.35 milliliters.

Figure 13:
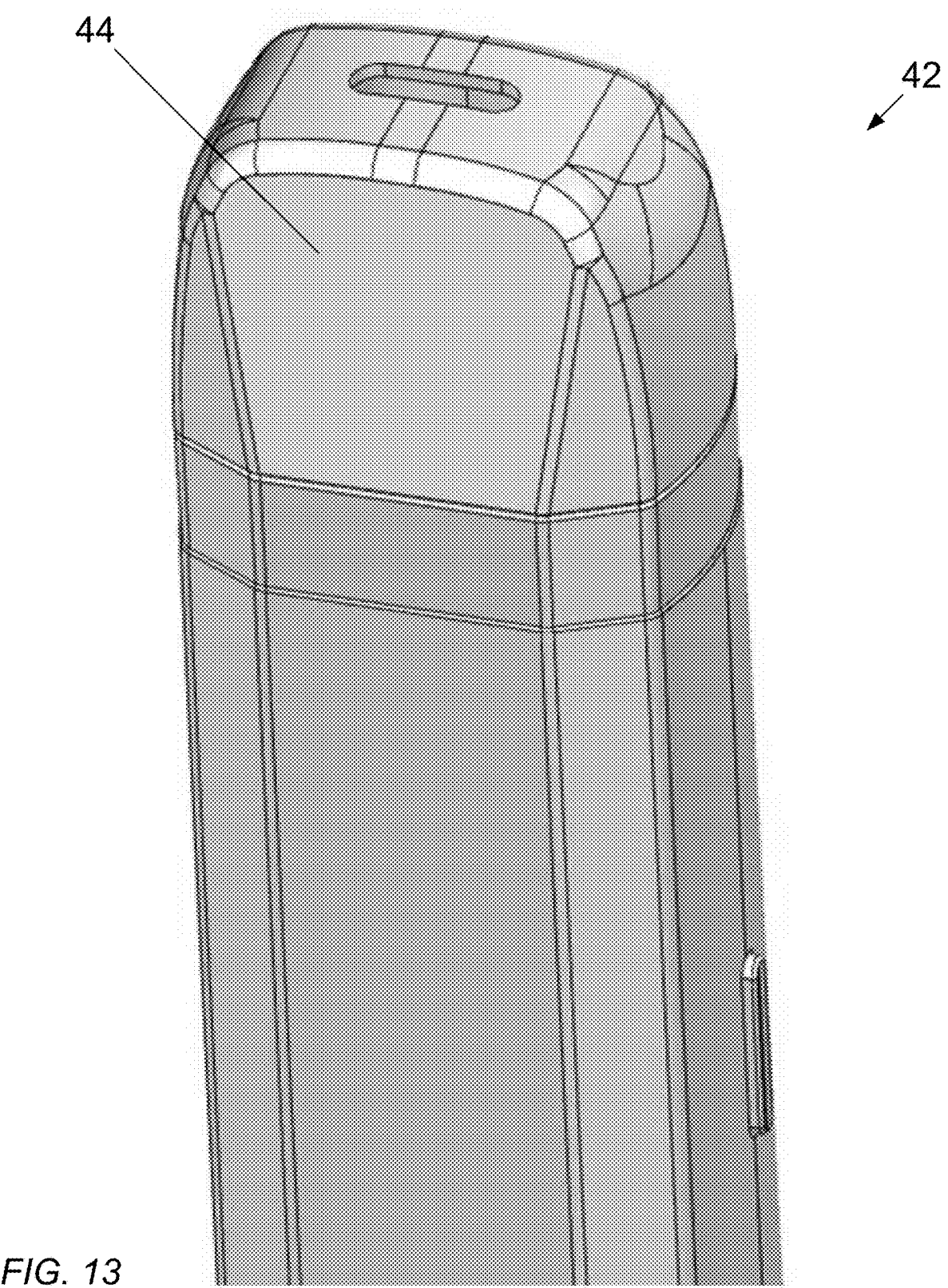
FIG. 13 is a partial perspective view of an end of a preferred embodiment of a vaporizer in accordance with one or more aspects and features of the invention, which end comprises a mouthpiece of the vaporizer.
Figure 14:
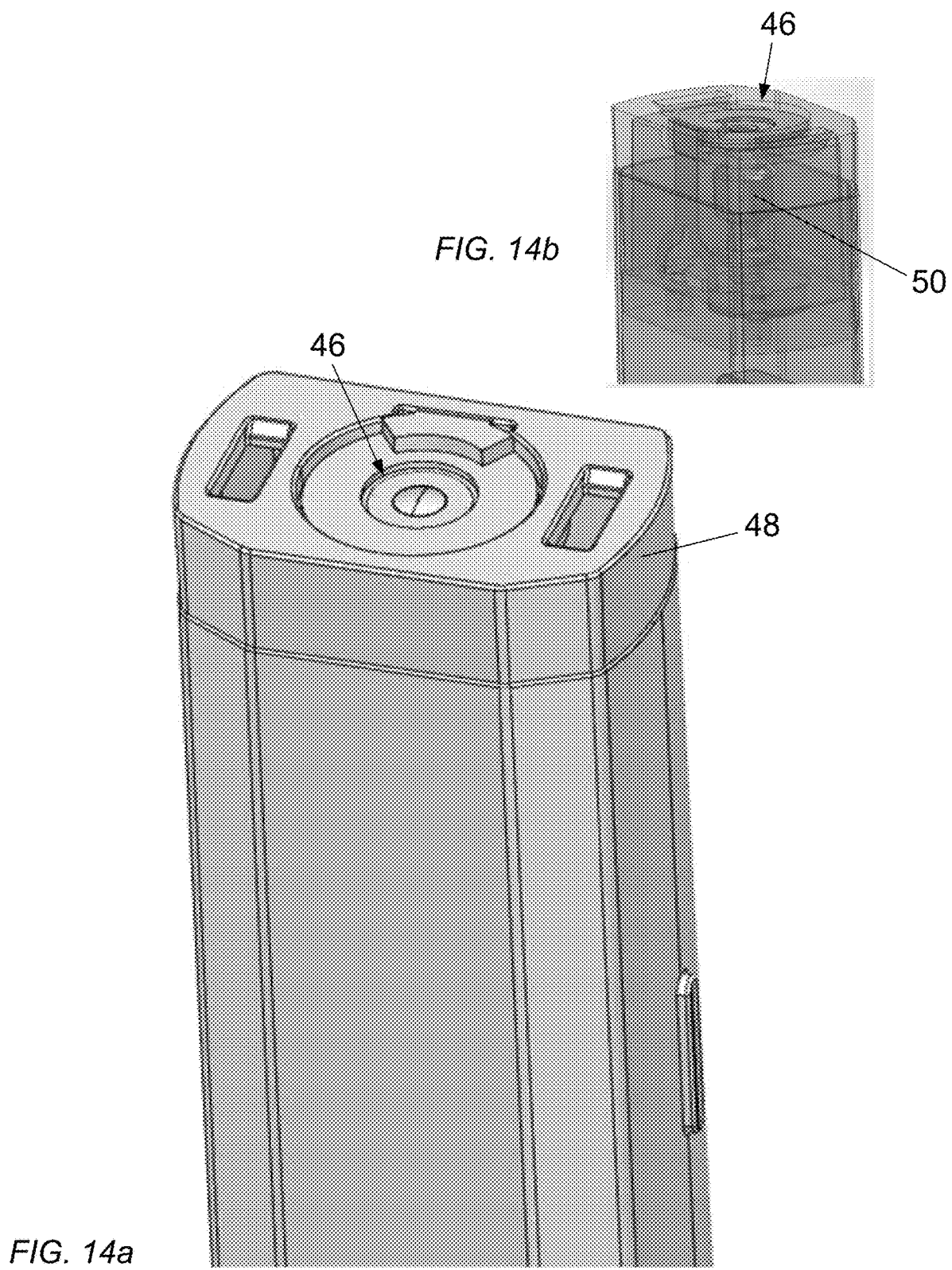
FIG. 14a is a view of the vaporizer as seen in FIG. 13 wherein the mouthpiece has been removed to reveal a piezo mesh disk of FIG. 13.
FIG. 14b is a transparent view of the vaporizer as seen in FIG. 14a, which reveals a bladder and the mesh assembly including the piezo mesh disk contained within a cartridge body in accordance with one or more aspects and features of the invention.
Figure 15:
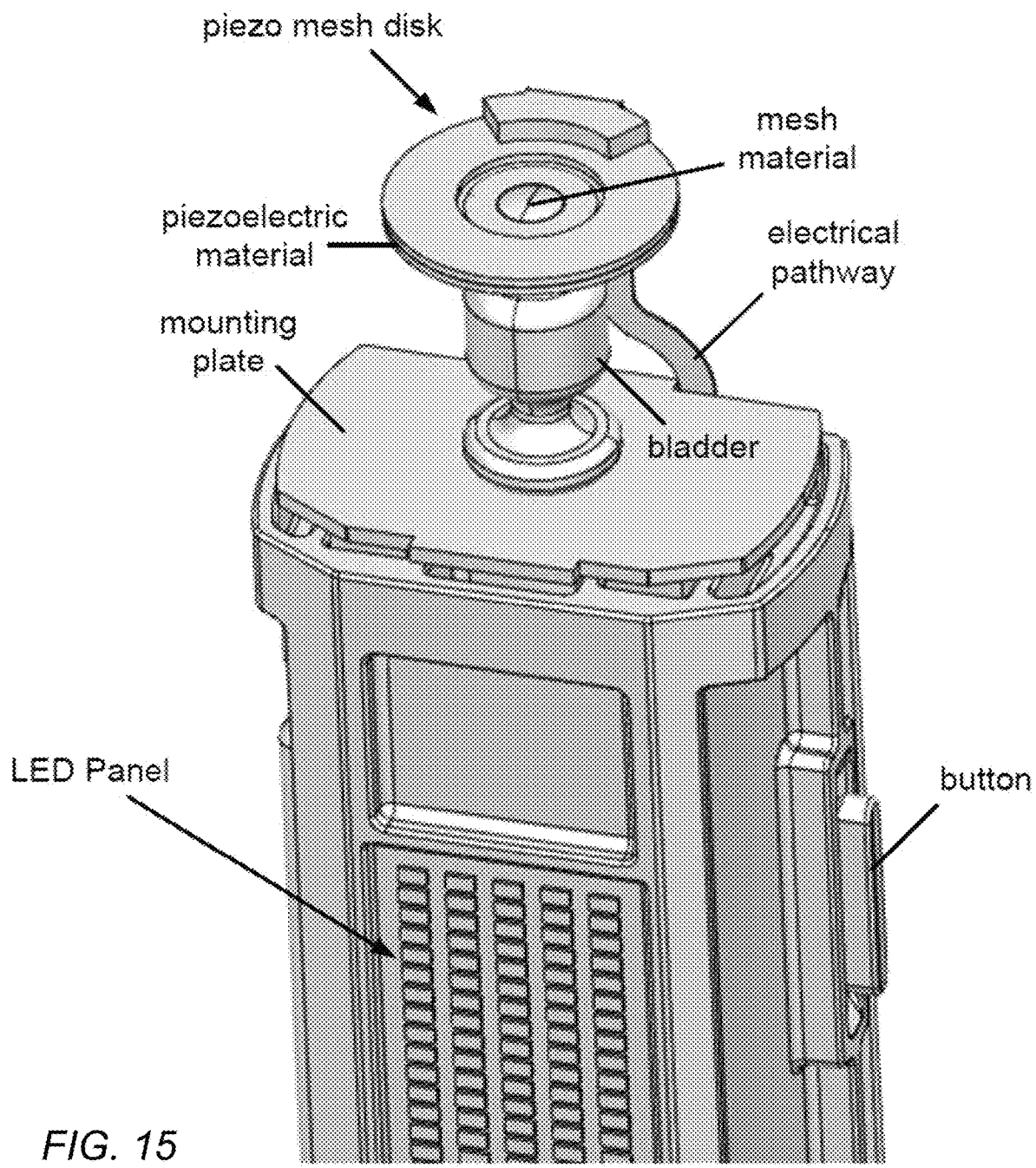
FIG. 15 is a perspective front view of the end of the vaporizer as seen in FIG. 14a, wherein the cartridge body and a main body casing have been removed to reveal the bladder secured to a mounting plate of the cartridge that, in turn, is secured to a main body chassis of the vaporizer.
Figure 16:
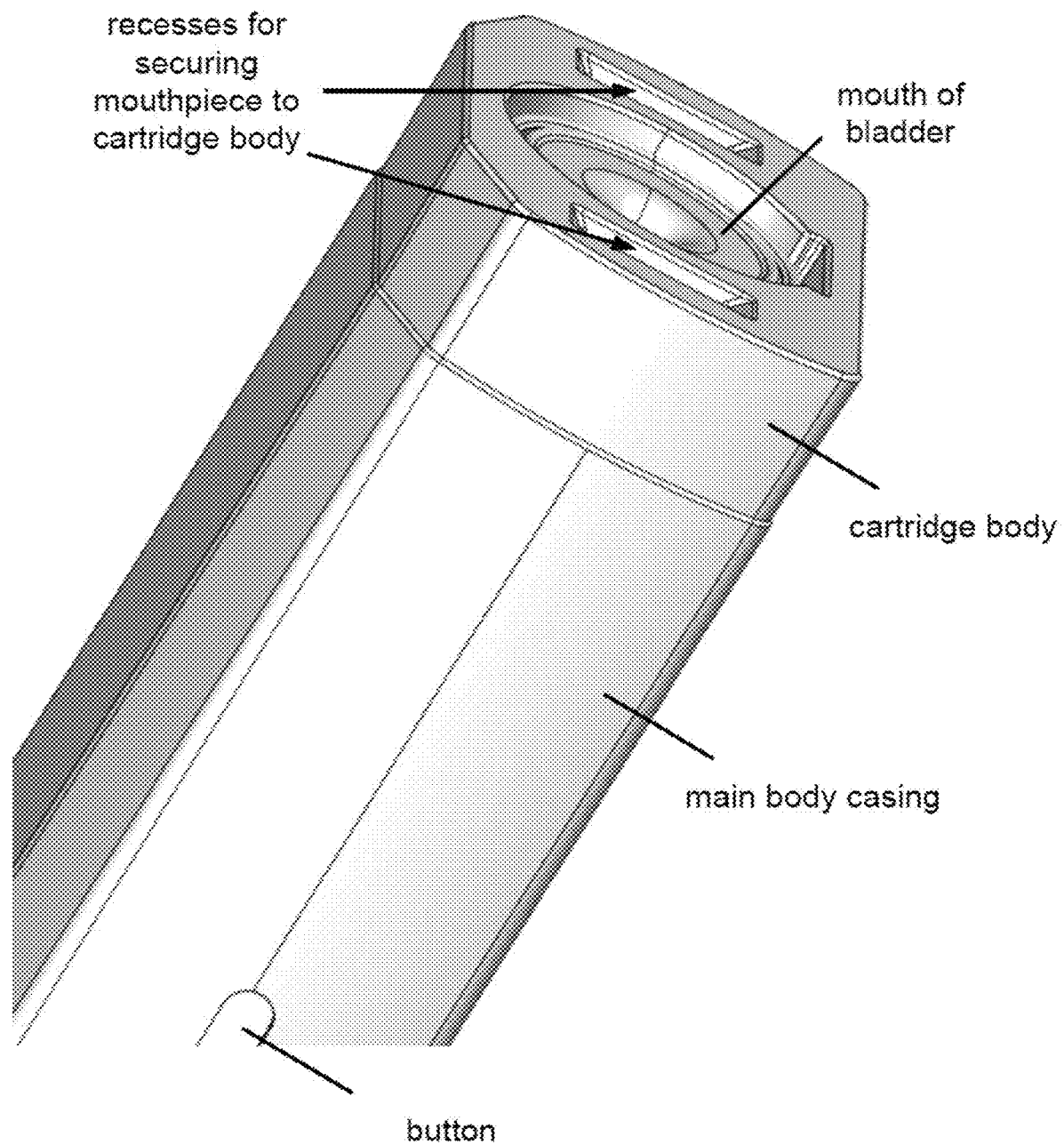
FIG. 16 is another view of the vaporizer as seen in FIG. 14a, wherein the piezo mesh disk has been removed to reveal a mouth of the bladder.
Figure 17A:
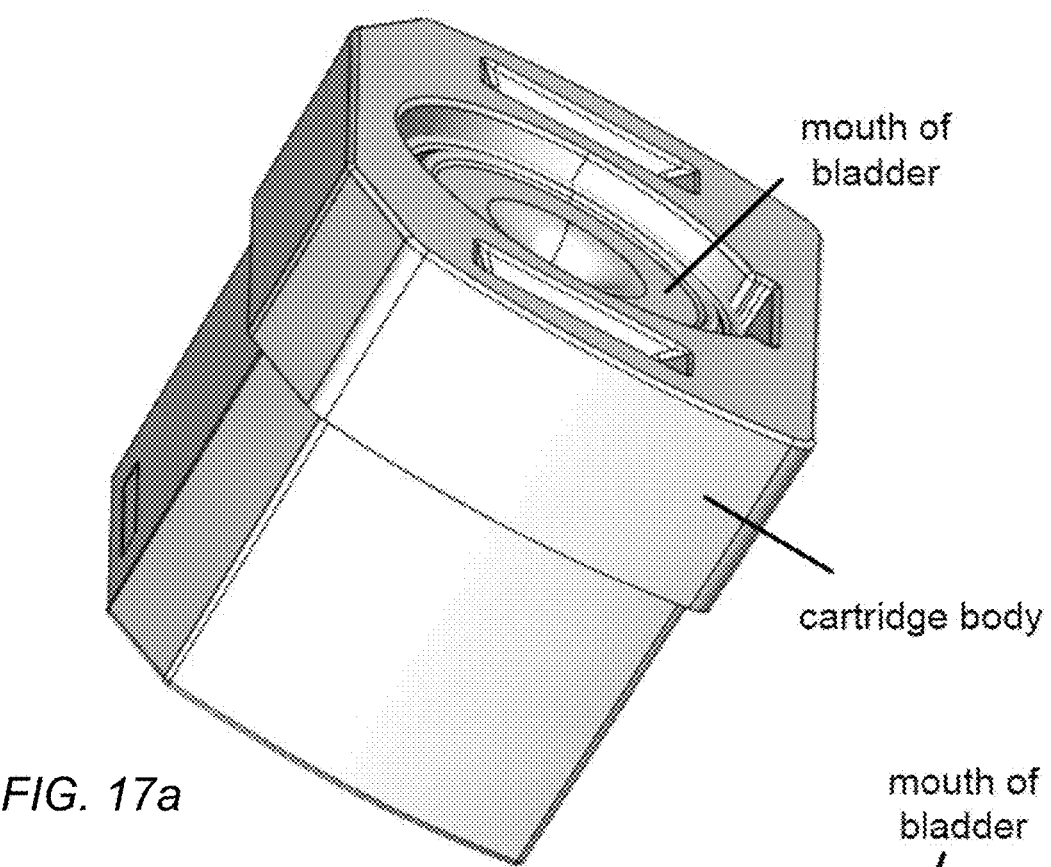
FIG. 17a is another view of the vaporizer as seen in FIG. 16, wherein just the cartridge body and bladder are shown.
Figure 17B:
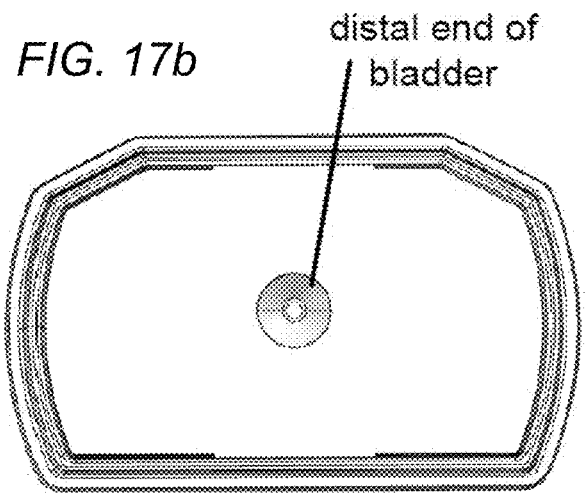
Figure 17C:
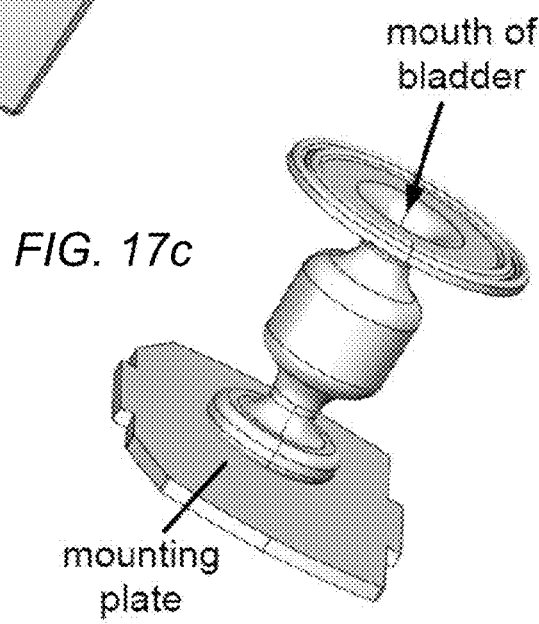
FIG. 17c is a perspective view of the bladder of the cartridge of FIG. 17a, which bladder is seen secured to the cartridge mounting plate.
Figure 17D:
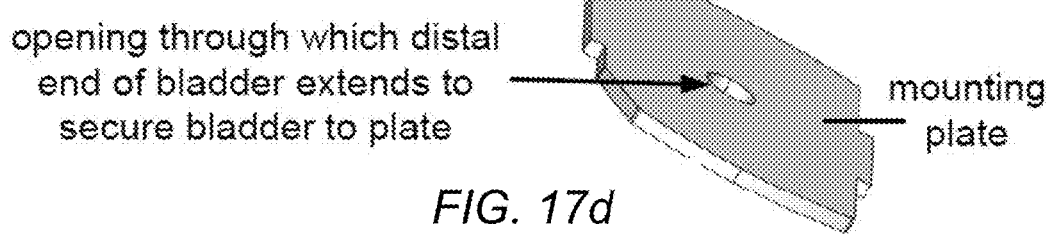
FIG. 17d is a perspective view of just the cartridge mounting plate as seen in FIG. 17c.
Figure 18A:
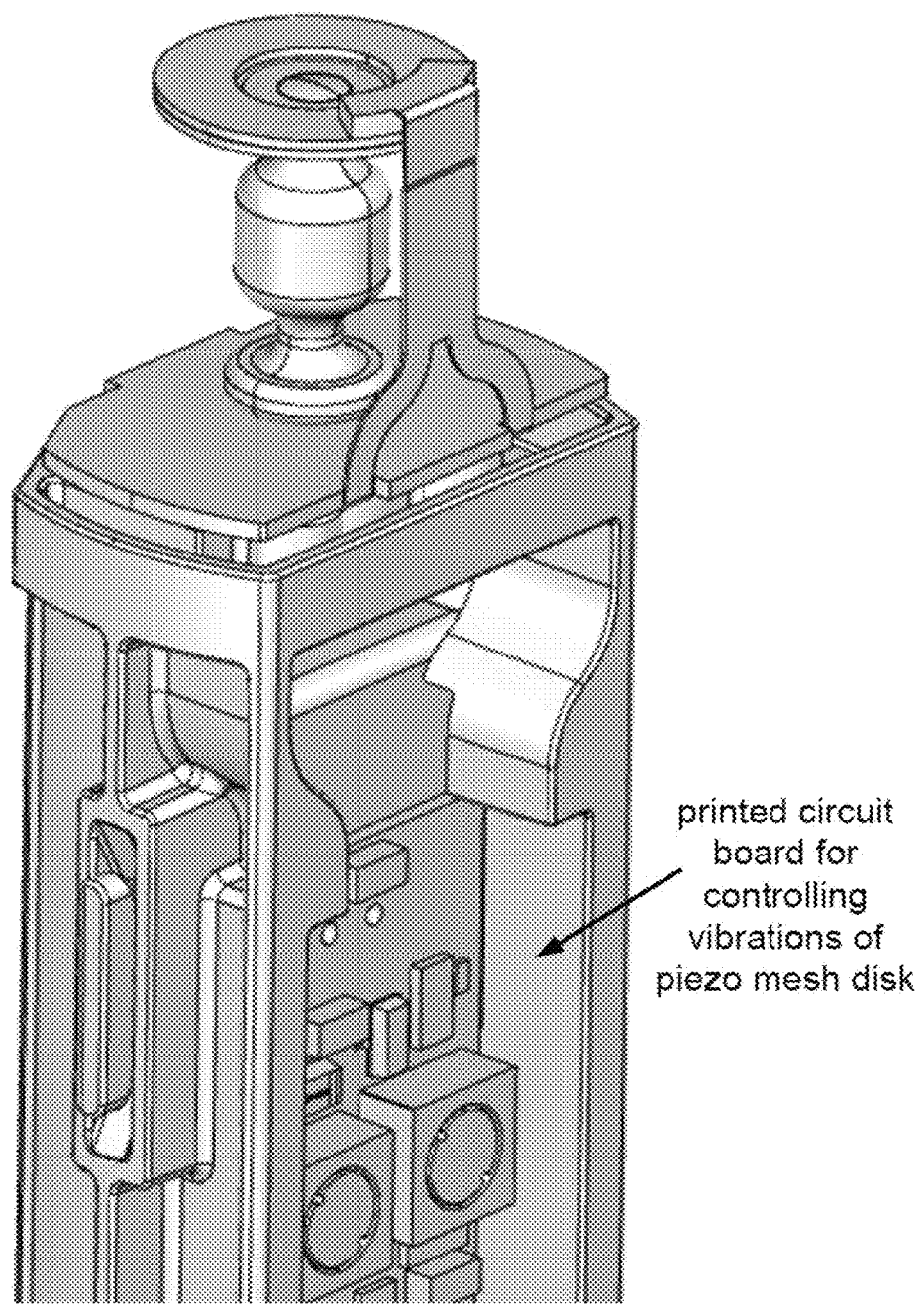
FIG. 18a is a perspective back view of the vaporizer as seen in FIG. 15.
Figure 18E:
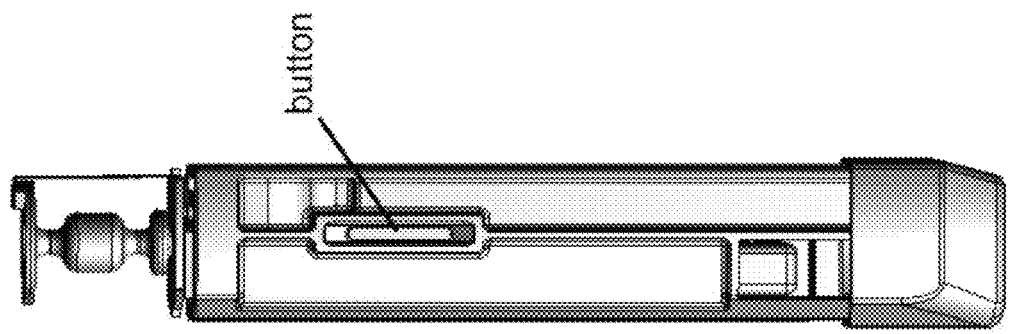
Figure 18D:
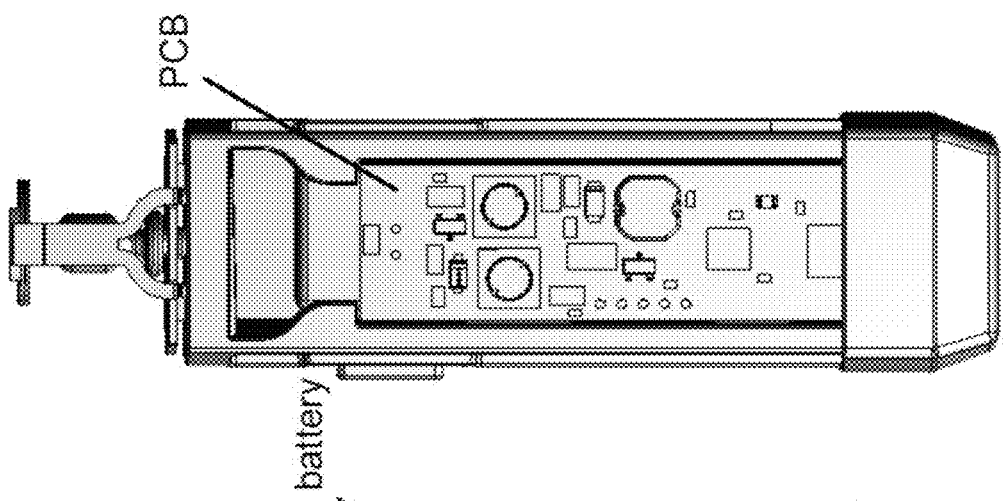
Figure 18C:
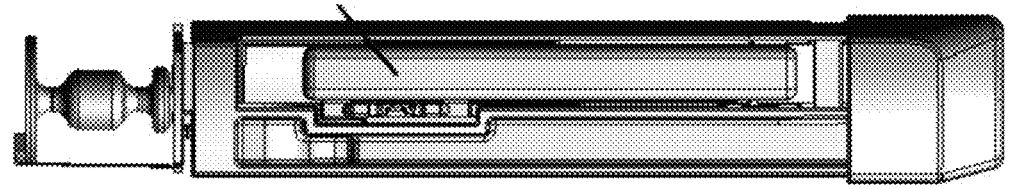
Figure 18B:
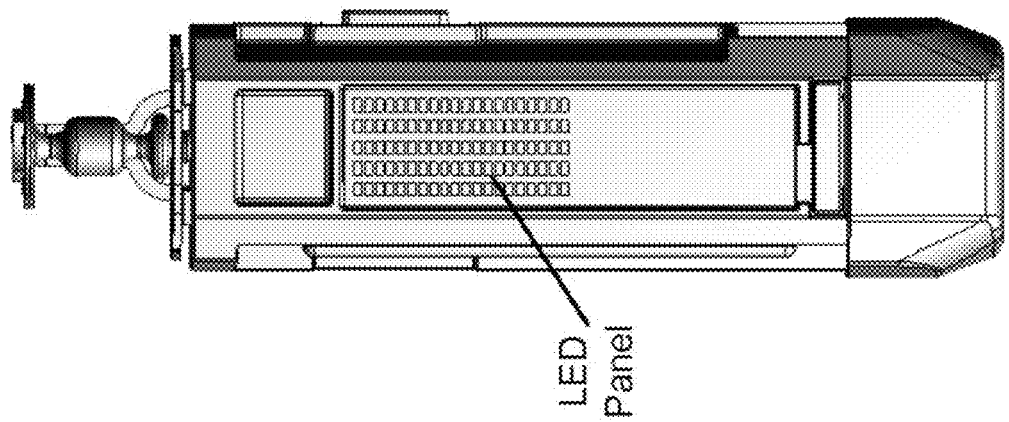

A third preferred embodiment of an electronic device in the form of a vaporizer 42 is illustrated in FIGS. 13-20i. In particular, FIG. 13 is a partial perspective view of an end of a preferred embodiment of a vaporizer in accordance with one or more aspects and features of the invention, which end comprises a mouthpiece 44 of the vaporizer; FIG. 14a is a view of the vaporizer as seen in FIG. 13 wherein the mouthpiece has been removed to reveal a piezo mesh disk 46. As seen in FIG. 14a, the piezo mesh disk is received with a cartridge body 48; FIG. 14b is a transparent view of the vaporizer as seen in FIG. 14a, which reveals a bladder 50 and the mesh assembly including the piezo mesh disk contained within the cartridge body in accordance with one or more aspects and features of the invention; FIG. 15 is a perspective front view of the end of the vaporizer as seen in FIG. 14a, wherein the cartridge body and a main body casing have been removed to reveal the bladder secured to a mounting plate of the cartridge that, in turn, is secured to a main body chassis of the vaporizer. An LED panel secured to the main body chassis of the vaporizer also is revealed in FIG. 15. The main body casing preferably is translucent, at least in the area covering and extending over the LED panel, whereby lighting from the LED panel passes through the main body casing for reading of the LED display but whereby the LED panel itself is otherwise concealed and hidden from sight, as represented for example in FIG. 3 of the '005 Publication; FIG. 16 is another view of the vaporizer as seen in FIG. 14a, wherein the piezo mesh disk has been removed to reveal a mouth of the bladder; FIG. 17a is another view of the vaporizer as seen in FIG. 16, wherein just the cartridge body and bladder are shown; FIG. 17b is a bottom plan view of the cartridge as seen in FIG. 17a; FIG. 17c is a perspective view of the bladder of the cartridge of FIG. 17a, which bladder is seen secured to the cartridge mounting plate; FIG. 17d is a perspective view of just the cartridge mounting plate as seen in FIG. 17c; FIG. 18a is a perspective back view of the vaporizer as seen in FIG. 15; FIG. 18b is an elevational front view of the vaporizer as seen in FIG. 18a; FIG. 18c is an elevational first side view of the vaporizer as seen in FIG. 18a; FIG. 18d is an elevational back view of the vaporizer as seen in FIG. 18a; FIG. 18e is an elevational second side view of the vaporizer as seen in FIG. 18a; FIG. 19a is a bottom perspective view of the bladder and mesh assembly, the cartridge mounting plate, and magnets by which the mounting plate is secured to the main body chassis; FIG. 19b is a top perspective view of the bladder and mesh assembly, the cartridge mounting plate, and magnets seen in FIG. 19a; FIG. 19c is a back perspective view of the bladder and the mesh assembly, the cartridge mounting plate, and magnets of FIG. 19a; FIG. 19d is a perspective elevational view of the bladder and the mesh assembly, the cartridge mounting plate, and magnets of FIG. 19a; FIG. 19e is another back perspective view of the bladder and the mesh assembly, the cartridge mounting plate, and magnets of FIG. 19a; FIG. 19f is a back elevational view of the bladder and the mesh assembly, the cartridge mounting plate, and magnets of FIG. 19a; FIG. 20a is a front perspective view of the bladder and the mesh assembly of FIG. 19a without the cartridge mounting plate and magnets; FIG. 20b is a bottom perspective view of the bladder and the mesh assembly of FIG. 20a; FIG. 20c is a back perspective view of the bladder and the mesh assembly of FIG. 20a; FIG. 20d is a back perspective view of the mesh assembly of FIG. 20a without the bladder; FIG. 20e is a back perspective view of the bladder of FIG. 20a without the mesh assembly; FIG. 20f is a bottom plan view of the bladder of FIG. 20e; FIG. 20g is a side elevational view of the bladder of FIG. 20e; FIG. 20h is a bottom perspective view of the bladder of FIG. 20e; and FIG. 20i is a top plan view of the bladder of FIG. 20a.

Other alternatives to the cartridges and bladders disclosed above are contemplated within the scope of the present invention and, indeed, are contemplated as forming part of other preferred embodiments of electronic devices of the invention. For example, FIG. 21a is a bottom perspective view of an alternative bladder 62 secured to the cartridge mounting plate 64 of FIG. 19a; and FIG. 21b is an exploded view of the alternative bladder 62 and mounting plate 64 of FIG. 21a.

FIG. 21c is yet another alternative bladder 62 secured to the cartridge mounting plate 64 of FIG. 19a, which view is a shaded line drawing; and FIG. 21d is a solid view of the view of FIG. 21c.

Figure 22E:
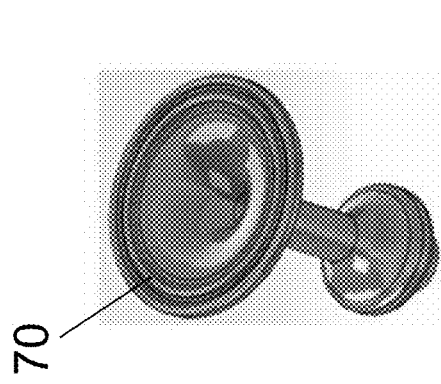
Figure 22F:
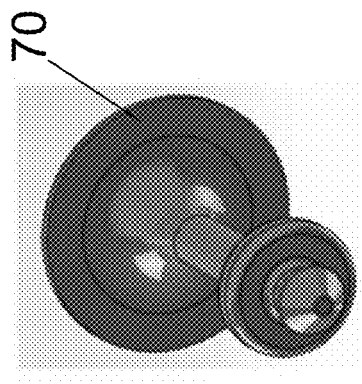
FIG. 22f is a bottom perspective view of the bladder of FIG. 22e.
Figure 22C:
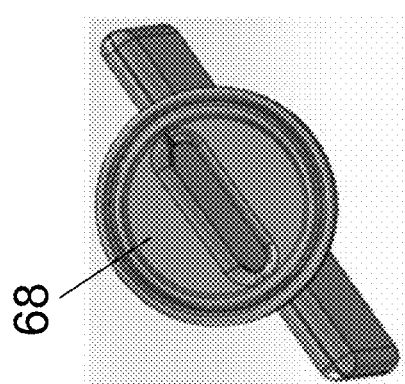
Figure 22D:
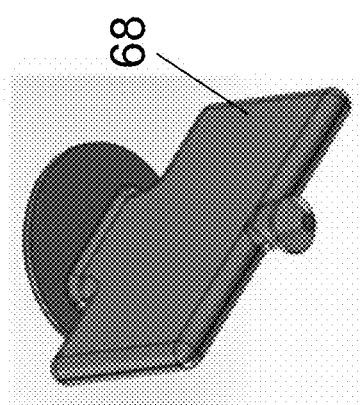
FIG. 22d is a bottom perspective view of the bladder of FIG. 22c.
Figure 22A:
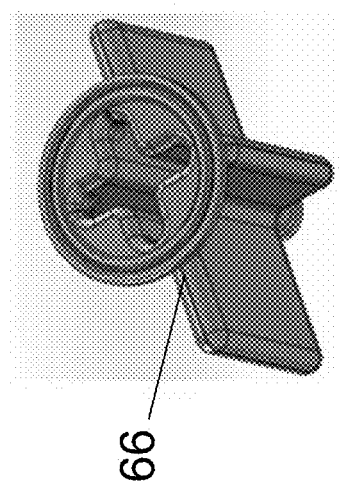
Figure 22B:
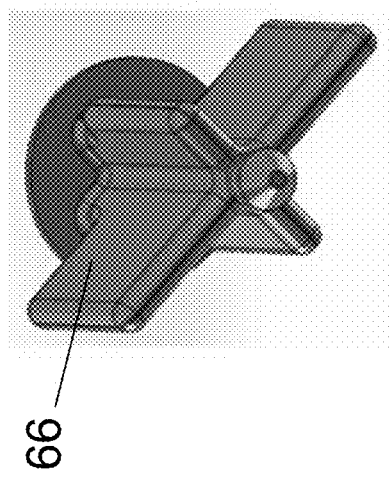
Figure 29A:
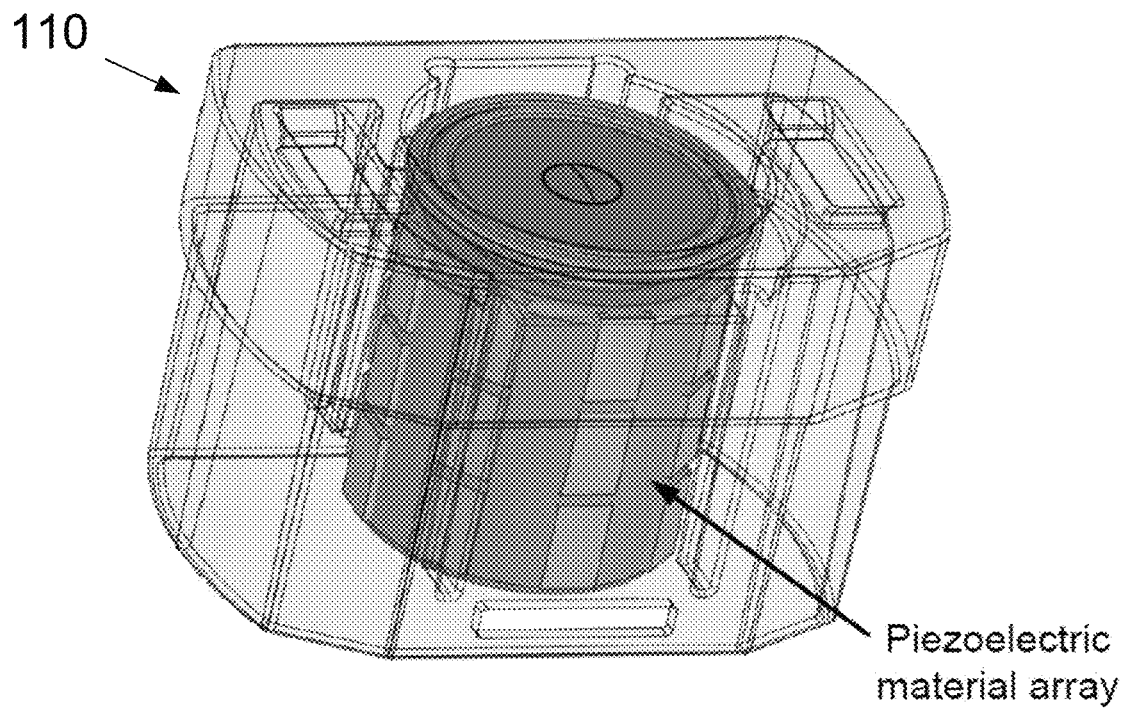
FIG. 29a is a top perspective view of an alternative cartridge for use with the vaporizer of FIG. 13 illustrating in solid view piezoelectric materials, mesh material, and bladder thereof.
Figure 29B:
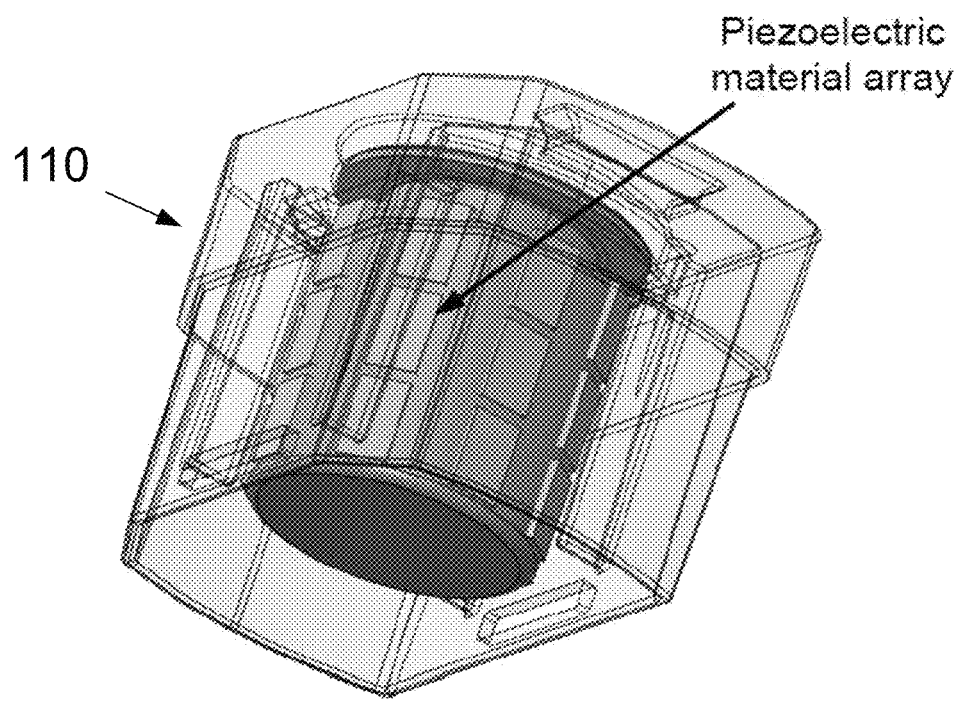
Figure 30A:
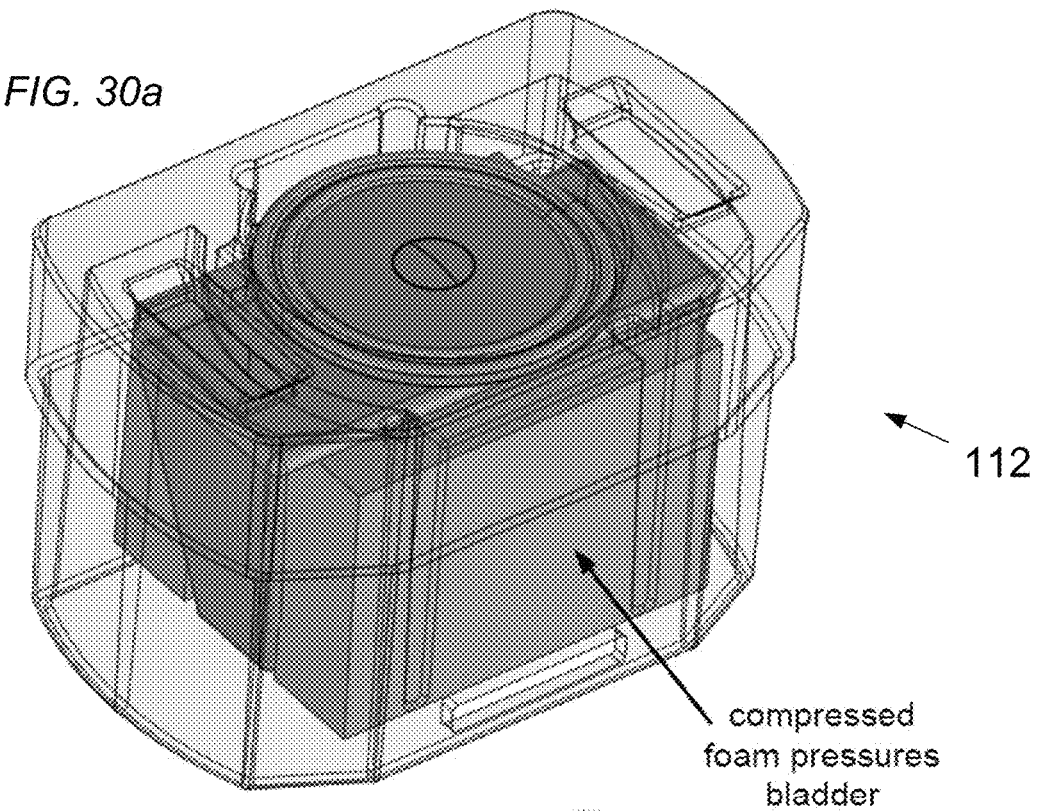
FIG. 30a is a top perspective view of an alternative cartridge for use with the vaporizer of FIG. 13 illustrating in solid view a piezoelectric material, mesh material, bladder, and foam inserts.
Figure 30B:
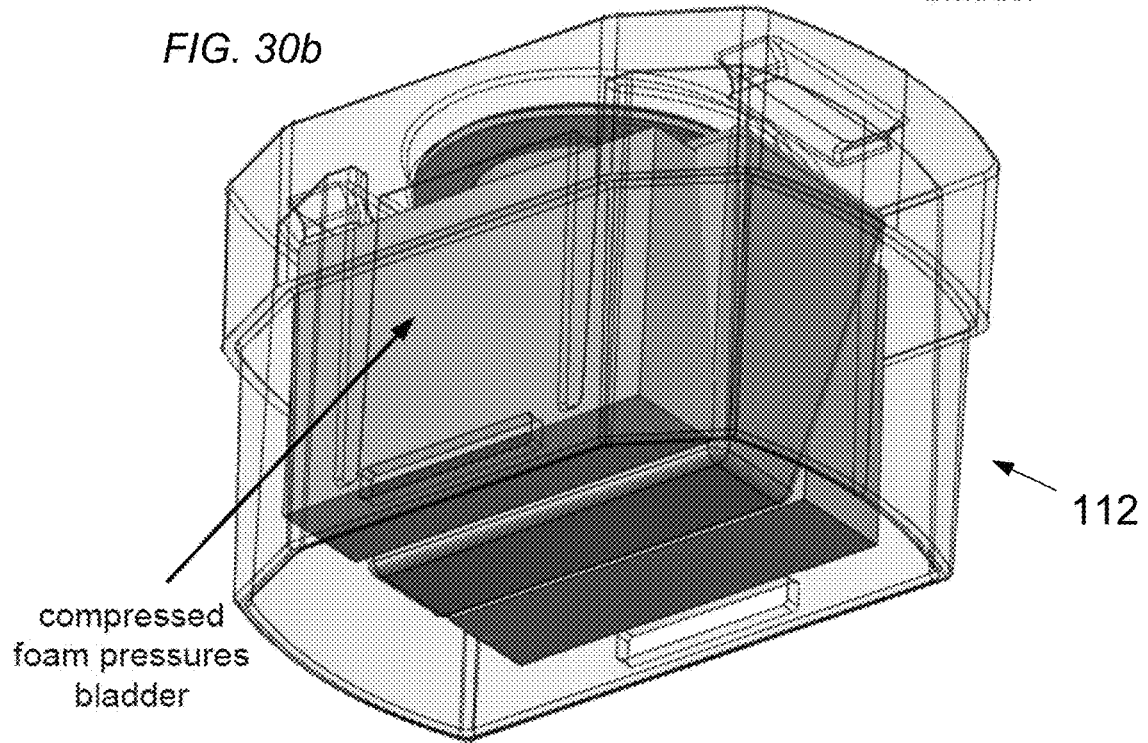

Additionally, FIG. 22a is a top perspective view of another alternative bladder 66 for use with the cartridge mounting plate of FIG. 19a; FIG. 22b is a bottom perspective view of the bladder of FIG. 22a; FIG. 22c is a top perspective view of another alternative bladder 68 for use with the cartridge mounting plate of FIG. 19a; FIG. 22d is a bottom perspective view of the bladder 68 of FIG. 22c; FIG. 22e is a top perspective view of another alternative bladder 70 for use with the cartridge mounting plate of FIG. 19a; and FIG. 22f is a bottom perspective view of the bladder 70 of FIG. 22e.

With particular regard to bladder shapes and geometries, including corrugated bladders, FIG. 23a is a top plan view of another alternative bladder 72 for use with the cartridge mounting plate of FIG. 19a; FIG. 23b is a bottom perspective view of the bladder 72 of FIG. 23a; FIG. 23c is a top plan view of another alternative bladder 74 for use with the cartridge mounting plate of FIG. 19a; FIG. 23d is a bottom perspective view of the bladder 74 of FIG. 23c; FIG. 23e is a top plan view of another alternative bladder 76 for use with the cartridge mounting plate of FIG. 19*a*; FIG. 23*f* is an elevational side view of the bladder 76 of FIG. 23*e*; FIG. 23*g* is a top plan view of another alternative bladder 78 for use with the cartridge mounting plate of FIG. 19*a*; and FIG. 23*h* is a bottom perspective view of the bladder 78 of FIG. 23*g*.

An example of a vaporizer 80 utilizing the bladder of FIG. 21*a* is seen in FIG. 24*a*, which is a wire frame illustration of the vaporizer illustrating in solid view use of the bladder of FIG. 21*a*. Furthermore, FIG. 24*b* is a transparent, top perspective view of a cartridge body 82 including mesh assembly illustrating in solid view use of the bladder of FIG. 21*a*; and FIG. 24*c* is a bottom perspective view of the cartridge body 82 of FIG. 24*b*.

FIG. 24*d* is a bottom perspective view of a cartridge 84 illustrating in solid view use of the bladder of FIG. 21*c*. FIG. 24*e* is a top perspective view of the cartridge of FIG. 24*d*.

Figure 32:
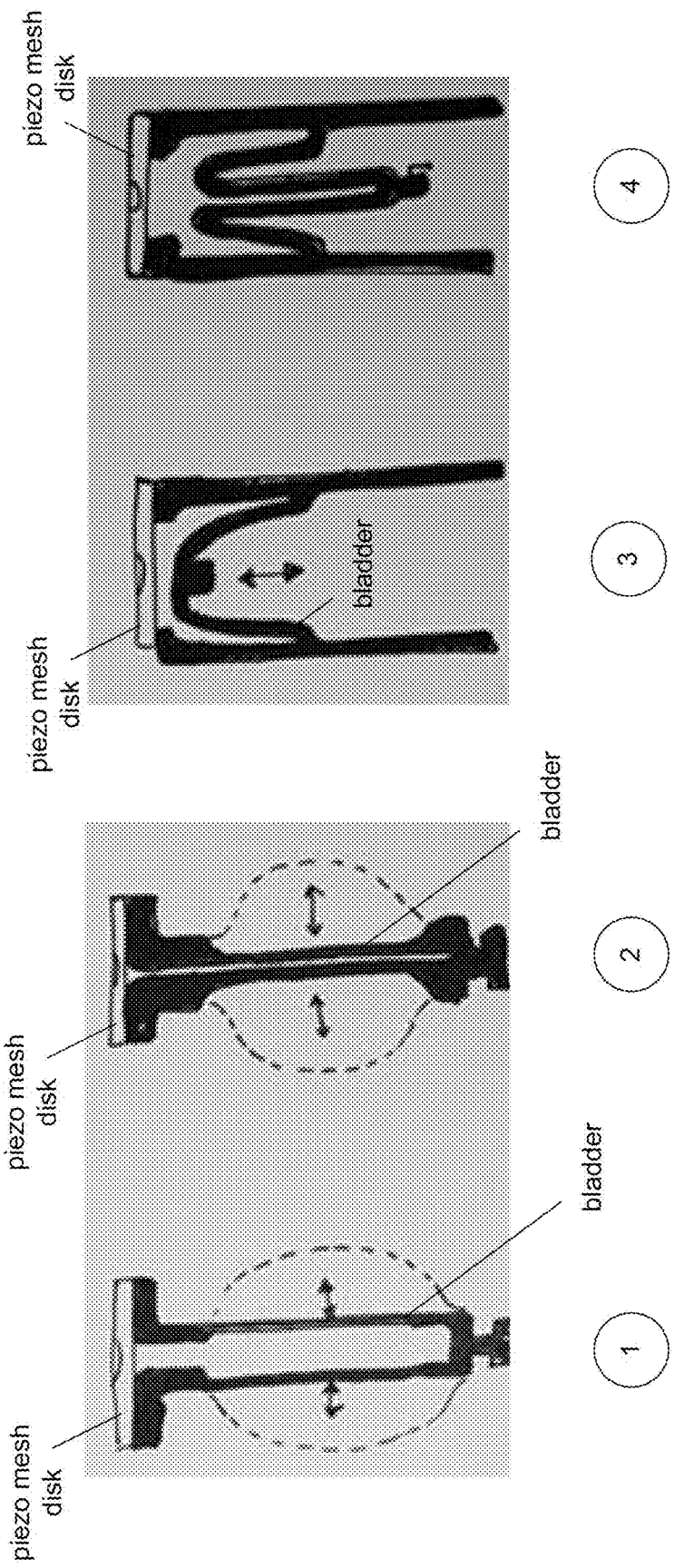
FIG. 32 additionally illustrates four additional low pressure bladder concepts that are contemplated for use in some preferred embodiments of the invention.

Different various methodologies for supplying liquid to the mesh assembly at a generally uniform pressure and so as to keep the liquid in continuous contact with the mesh material are disclosed in the alternative embodiments of cartridges seen in FIGS. 25*a* through 30*b*. FIG. 31 additionally sets forth other potential means for causing the liquid to contact the mesh material, which are shown in contrast to gravity fed systems. FIG. 32 additionally illustrates four additional low pressure bladder concepts that are contemplated for use in some preferred embodiments of the invention.

For example, FIG. 25*a* is a perspective view of an alternative cartridge 90 for use with the vaporizer of FIG. 13 illustrating in solid view a piezoelectric material, mesh material, bladder, and a mechanism for driving fluid from the bladder to the mesh material for aerosolizing; FIG. 25*b* is a perspective view of the other side of the cartridge of FIG. 25*a*; and FIG. 25*c* is a side elevational view of the cartridge of FIG. 25*a*.

FIG. 25*d* is a perspective view of an alternative cartridge 92 for use with the vaporizer of FIG. 13 illustrating in solid view a piezoelectric material, mesh material, bladder, and a mechanism for driving fluid from the bladder to the mesh material for aerosolizing. FIG. 25*e* is a view of the cartridge of FIG. 25*d* without the mechanism of FIG. 25*d*; and FIG. 25*f* is another view of the cartridge of FIG. 25*e* from a side opposite to the side of the view of FIG. 25*e*.

FIG. 26*a* is a top perspective view of an alternative cartridge 94 for use with the vaporizer of FIG. 13 illustrating in solid view a piezoelectric material, mesh material, bladder, and a mechanism for driving fluid from the bladder to the mesh material for aerosolizing. FIG. 26*b* is a bottom perspective view of the cartridge of FIG. 26*a*.

FIG. 26*c* is a top perspective view of an alternative cartridge 96 for use with the vaporizer of FIG. 13 illustrating in solid view a piezoelectric material, mesh material, bladder, and a mechanism for driving fluid from the bladder to the mesh material for aerosolizing.

FIG. 26*d* is a bottom perspective view of yet another alternative cartridge 98 for use with the vaporizer of FIG. 13 illustrating in solid view a piezoelectric material, mesh material, bladder, and a mechanism for driving fluid from the bladder to the mesh material for aerosolizing. FIG. 26*e* is a top perspective view of the cartridge of FIG. 26*d* without the mechanism of FIG. 26*d*.

FIG. 26*f* is a top perspective view of yet another alternative cartridge 100 for use with the vaporizer of FIG. 13 illustrating in solid view a piezoelectric material, mesh material, bladder, and a mechanism for driving fluid from the bladder to the mesh material for aerosolizing.

FIG. 27*a* is an elevational view of an alternative cartridge 102 for use with the vaporizer of FIG. 13 illustrating in solid view a bladder thereof. FIG. 27*b* is a top perspective view of the cartridge of FIG. 27*a*; and FIG. 27*c* is a bottom perspective view of the cartridge of FIG. 27*a*. The bladder, which folds or collapses in an accordion-like fashion, preferably comprises folds lines and is made of silicone.

FIG. 27*d* is a bottom perspective view of yet another alternative cartridge 104 for use with the vaporizer of FIG. 13 illustrating in solid view a bladder thereof which is similar to the bladder of FIG. 27*a*, but which includes a radial arm for side filling of liquid through injection at an injection site that is on a side of the cartridge rather than at the bottom of the cartridge. FIG. 27*e* is a top perspective view of the cartridge of FIG. 27*d*.

FIG. 28*a* is top perspective view of an alternative cartridge 106 for use with the vaporizer of FIG. 13 illustrating in solid view a piezoelectric material, mesh material, and bladder thereof; and FIG. 28*b* is a bottom perspective view of the cartridge of FIG. 28*a*. The bladder of these figures has a large volume is shown open or exposed. A mechanism for pressing against the bladder for expelling or driving the liquid therein into constant contact with the mesh material of the piezo mesh disk is preferably utilized, such mechanism being any of those disclosed herein.

FIG. 28*c* is top perspective view of yet another alternative cartridge 108 for use with the vaporizer of FIG. 13 illustrating in solid view a piezoelectric material, mesh material, and bladder thereof. FIG. 28*d* is another top perspective view of the cartridge of FIG. 28*c*; and FIG. 28*e* is a bottom perspective view of the cartridge of FIG. 28*c*. The bladder of this cartridge is the same as that of FIGS. 28*a*-28*b* with the exception that the bladder is contained within a chamber the conforms to the filled shape of the bladder. The chamber is open at the bottom, as seen in FIG. 28*e*. Use of a chamber facilitates use of a fluid, such as a gas or a secondary liquid, to be used for pressuring and collapsing the bladder.

FIG. 29*a* is a top perspective view of an alternative cartridge 110 for use with the vaporizer of FIG. 13 illustrating in solid view piezoelectric materials, mesh material, and bladder thereof; and FIG. 29*b* is a bottom perspective view of the cartridge of FIG. 29*a*. The cartridge in these figures comprises a piezoelectric array located around the bladder. Each member of the array preferable is actuated in a sequence that drives the liquid toward the mouth of the bladder into contact with the mesh material of the piezo mesh disk. For example, the sequence of actuation can constrict the bladder beginning at the distal end with the constriction working its way toward the mouth, similar to intestinal movement.

FIG. 30*a* is a top perspective view of an alternative cartridge 112 for use with the vaporizer of FIG. 23 illustrating in solid view a piezoelectric material, mesh material, bladder, and foam inserts or blocks.

FIG. 30*b* is a bottom perspective view of the cartridge of FIG. 40*a*. This cartridge comprises foam that is compressed when the bladder is filled. The compression of the foam preferable will pressure the bladder and drive liquid into constant contact with the mesh material of the piezo mesh disk. The foam may be an open cell foam.

Other contemplated ways of pumping, pushing, or otherwise forcing the liquid into contact with the vibrating mesh include using a solenoid pump, a capillary tube or plurality of capillary tubes, and a vacuum pump. Gravity may also be used when the electronic device is not intended to be orientation-agnostic in use, but such use is not preferred.

In each instance regardless of the manner in which the liquid is pushed from the cartridge into contact with the vibrating mesh, the liquid preferably is supplied to the vibrating mesh at a generally constant pressure whereby a generally uniform aerosol is produced. This is preferably done regardless of the orientation of the electronic device. The electronic device also preferably comprises a reservoir for the liquid. In some embodiments, the reservoir is an anti-pyrolysis vape reservoir with no smoldering and no combustion. In some embodiments, the liquid of the device features a thermostable liquid carrier.

Circuitry shown in the form of a printed circuit board or "PCB" in FIG. 18*d*, for example, preferably is included in each electronic device for controlling actuation of the vibrating mesh. A printed circuit board may comprise an application specific integrated circuit. The actuation and resulting vibrations/oscillations preferably are consistent for consistently generating the aerosol, with minimal variations or fluctuations in frequency and amplitude. The circuitry also preferably controls actuation of the mechanism—when an active mechanism—for pushing the liquid into contact with the vibrating mesh at a generally constant pressure. A microcontroller also may be included.

Additionally, with regard to more aspects and features of the present invention, the mesh material preferably has opening diameters of 1-2 microns, or 1,000-2,000 nanometers; when actuated, the flow rate of the liquid from the bladder to the vibrating mesh material is preferably about 0.25 milliliters per minute; preferred overall dimensions of a vaporizer are about 16 millimeters by 25 millimeters by 110 millimeters; and a vibrating mesh preferably remains in direct contact with the liquid for consistent production of the aerosol.

Furthermore, the bladder preferably physically contacts and forms a seal with the piezo mesh disk so that liquid from the bladder does not leak from the bladder. Specifically, a top flange of the bladder preferably services as a gasket or glad seal to the underside of the piezo mesh disk. The bottom end of the bladder preferably comprises the fill site and also serves to anchor and mechanically hold bladder in its position within the cartridge.

Additionally, the bladder preferably contains the volume of liquid behind the mesh at a relatively low pressure regardless of orientation as the volume is depleted with use. The seal is believed to fail at pressures above about 0.3 psi and, therefore, the liquid preferably is driven from the bladder into contact with the mesh material at less than 0.3 psi. The pressure at which the liquid is supplied to the mesh material therefore has been found to be very low.

When the liquid is an aqueous mixture (e.g., water or saline), the liquid preferably contacts the mesh material at a pressure less than about 0.3 psi. It is believed that higher pressure will lead to leaking and failure of the mesh material to produce a desired aerosol consistent with a vapor cloud. Higher pressure indeed may likely lead to the fluid flowing through perforations of the mesh material and flooding or wetting the other side of the mesh material causing the mesh material to not function correctly in producing the desired aerosol until dry. Higher pressure also may result in stretching and deformation of the wall so the bladder, resulting in mechanical failure.

The bladder also preferably acts as a capillary pump in addition to serving as a reservoir for the liquid.

Many preferred electronic devices of the invention are orientation agnostic, meaning that the desired aerosol is produced regardless of the direction an electronic device is held when used relative to the forces of gravity.

Disposable cartridges in accordance with preferred embodiments of the invention each comprises a mesh assembly including aperture plate and electronic contacts, a bladder, and a mouthpiece.

In accordance with a feature of the invention, the bladder has a hardness of about 40 durometer.

While alternatives such as pumps, drives, pistons, and wicking solutions are disclosed for causing the liquid in the bladder to be in contact with the mesh material, the bladder is believed to be the simplest mechanism and therefore is preferred. Furthermore, the bladder preferably is formed from a self-healing silicone material and can be filled with a syringe without injecting air into the bladder. This process preferably is automated and occurs during assembly of cartridges and/or vaporizers.

In some preferred embodiments, the bladder comprises corrugated walls and is formed from a flexible material and has flexibility such that the bladder changes volume without initially stretching of the material from which it is formed. Moreover, the volume of the bladder preferably is extremely low of nothing when the bladder is in a natural, fully relaxed (or collapsed) state. When fully collapsed, the bladder preferably provides some capillary benefit to extract the last amount of liquid from the bladder. To this end, it is believed that the vibrating mesh is able to create a light vacuum which is instrumental in fully evacuating the bladder of the liquid contained therein.

In some preferred embodiments of the invention, the electronic device comprises a vibrating mesh nebulizer coupled with a capillary-effect/vacuum pump system (corrugated silicone bladder), that acts as an orientation agnostic "liquid drive", whereby the vaporizer is able to be held in any direction and still function properly.

In at lease some preferred embodiments, the corrugated bladder acts both as the capillary/vacuum pump as well as the liquid reservoir, ensuring that the liquid is in constant contact with the vibrating mesh, without disturbing the oscillations of the mesh material when the piezoelectric material is actuated.

Bladders disclosed also are believed to provide a range of interior surface areas relative to volume and pressure for desired supply of the liquid to the mesh material and proper operation of the vaporizer. Indeed, other shapes and geometries may not enable the capillary action of the bladder, the orientation-agnostic character of the operation of the vaporizer, and the proper oscillation of the mesh material (i.e., too much pressure and leaking of the fluid can mute oscillations of the mesh material, inhibiting aerosolizing of the liquid in a vaping form). Flexibility of design also allows corrugated walls and flexibility of the material the bladder allows changes in volume without initially stretching the material, which is preferred. Thus, in at least some preferred embodiments, the volume of a natural state or relaxed state of the bladder is basically zero. When all fully collapses some capillary benefit should be obtained in order to extract last amount of liquid from the bladder, especially when combined with the light vacuum provided by the vibrating mesh.

Additionally, while the top flange of the bladder serves as a gasket or glad seal to the underside of the mesh, the bottom distal end or "post" of the bladder that preferably serves the fill sight also mechanically holds the bladder in position when secured to the mounting plate of the cartridge.

With regard to additional aspects, features and embodiments of the invention, and with reference to FIGS. 33-35, a preferred active ingredient delivery system for inhalation is contemplated to be capable of accommodating and delivering a range of different types of active ingredients to the body through the pulmonary system. Active ingredients capable of delivery using one or more delivery systems described herein include, but are not limited to, pharmaceutical compounds, tetrahydrocannabinol (THC), cannabidiol (CBD), and nicotine. The following description of embodiments sets forth one or more active ingredient delivery systems largely within the context of delivering THC and/or CBD, but it should be understood that active ingredient delivery systems described herein are also usable for delivery of nicotine, pharmaceuticals, micronutrients, and other types of active ingredients by inhalation and are not limited to delivery of THC/CBD.

THC and CBD are two of several different cannabinoids found in plants of the *Cannabis* genus. Using extraction techniques, THC and CBD can be isolated from the plant matrix for medicinal and/or recreational use. THC and CBD interact with different receptors in the human brain and, thus, cause a different treatment or effect in the user. For purposes of the below discussion, THC and CBD may be referenced together as "THC/CBD." It should be understood that, as used herein, "THC/CBD" refers to a cannabinoid-based active ingredient that includes both THC and CBD, THC without CBD, or CBD without THC.

THC and CBD are hydrophobic molecules that do not readily mix with aqueous solutions like water. To facilitate delivery to the human body, THC/CBD molecules are encapsulated into nanoparticles comprising oil droplets of the THC/CBD active ingredient surrounded by one or more encapsulation agents, such as surfactants or emulsifiers, which shield the oil droplets from the surrounding aqueous environment. The shielded oil droplets can then mix into aqueous solutions. One example of such a mixture is a nanoemulsion, where the oil phase includes the hydrophobic THC/CBD molecules shielded by one or more surfactants from the surrounding aqueous phase.

Figure 33:
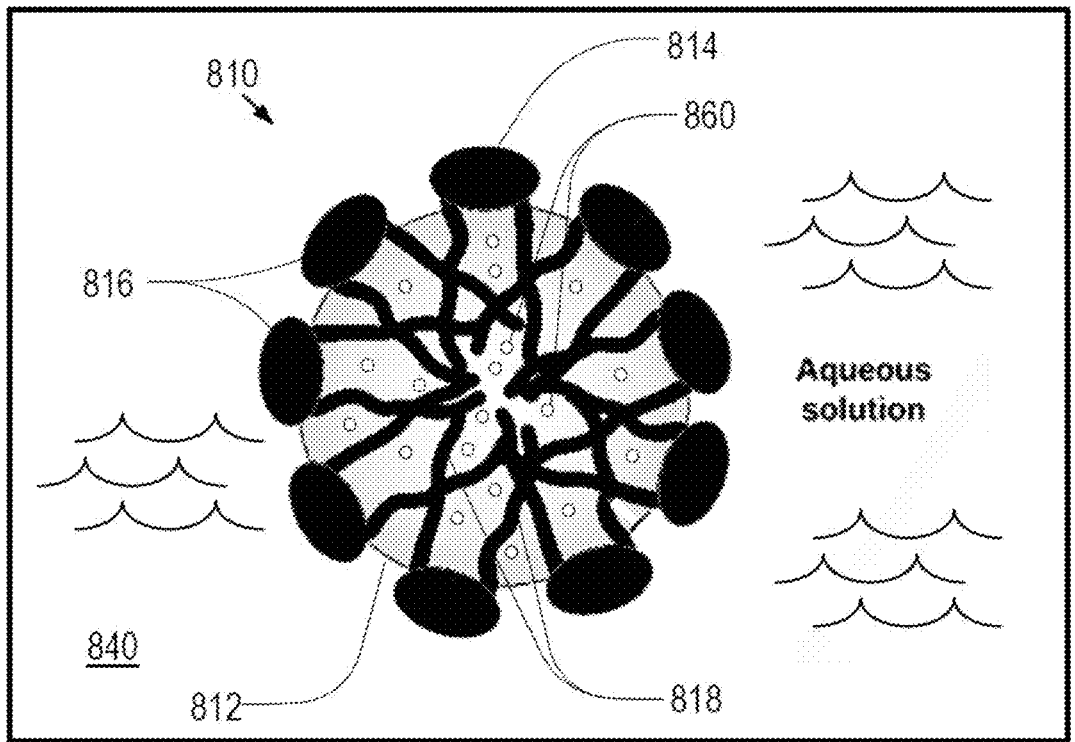
FIG. 33 is a schematic diagram of an active ingredient pulmonary delivery nanoparticle in the form of a micelle in accordance with one or more aspects of the invention.

FIG. 33 is a schematic diagram of an active ingredient pulmonary delivery nanoparticle in the form of a micelle 810 in accordance with one or more aspects of the invention. In FIG. 33, the hydrophobic droplet 812 comprised of oil containing THC/CBD molecules is surrounded by a monolayer 814 of one or more encapsulation agents, which forms an aggregate. In at least some embodiments, the monolayer 814 is a lipid-based monolayer. Molecules forming the monolayer 814 include hydrophilic heads 816 that are in contact with the surrounding aqueous solution 840 and hydrophobic tails 818 that extend toward the micelle center. The hydrophilic heads 816 form the boundary of the monolayer 814 that facilitates isolation of the hydrophobic component, including the hydrophobic active ingredient 860, to permit mixing of the micelle 810 into the aqueous solution 840. As shown in FIG. 33, the micelle 810 is largely spherical in shape, although non-spherical shapes are also possible. As shown in FIG. 33, the micelle 810 and the aqueous solution 840 are contained within a cartridge 800.

Figure 34:
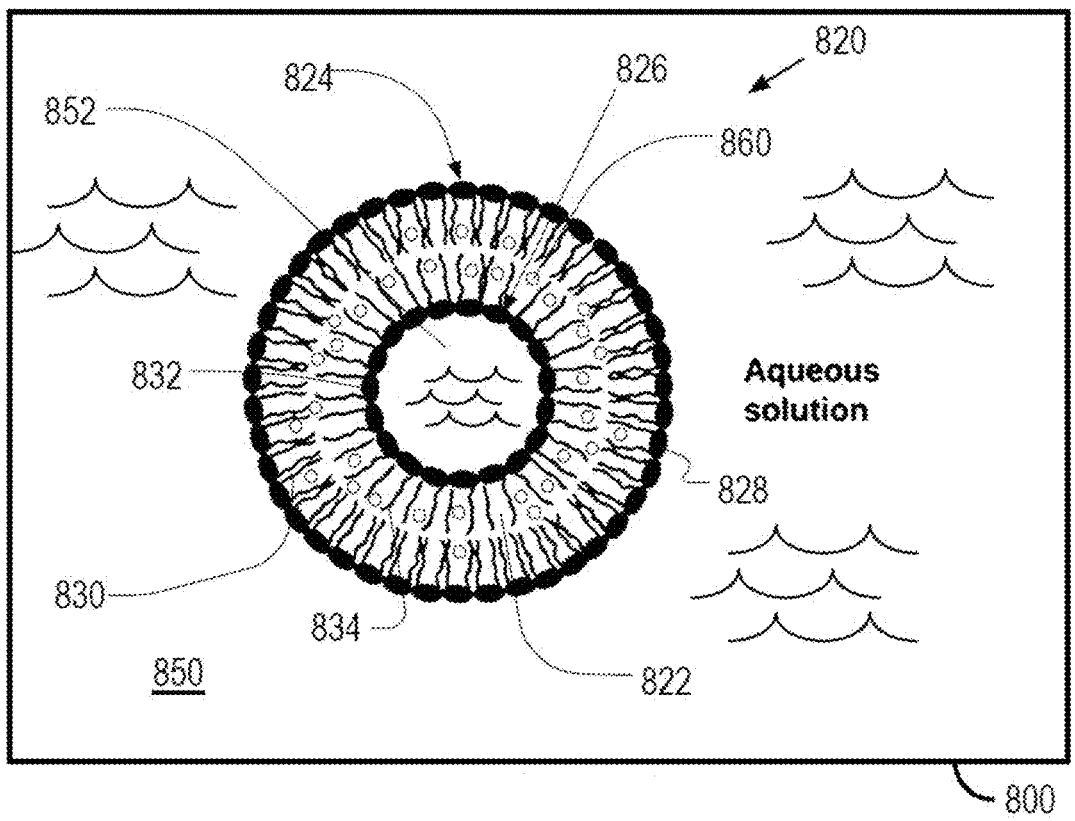
FIG. 34 is a schematic diagram of an active ingredient pulmonary delivery nanoparticle in the form of a liposome carrying an active ingredient within a bilayer in accordance with one or more aspects of the invention.

FIG. 34 is a schematic diagram of an active ingredient pulmonary delivery nanoparticle in the form of a liposome 820 carrying an active ingredient 860 within a bilayer in accordance with one or more aspects of the invention. In FIG. 34, the oil component resides in a hydrophobic area 822 of the liposome 820 between a bilayer of one or more encapsulation agents. In at least some embodiments, the bilayer is a lipid-based bilayer. Molecules that form the outer layer 824 of the bilayer include hydrophilic heads 828 that are in contact with the surrounding aqueous solution 850 and hydrophobic tails 830 that extend into the hydrophobic area 822 between the layers 822,824. Lipid molecules that form the inner layer 826 of the bilayer include hydrophilic heads 832 that are in contact with the aqueous solution 852 at the center of the liposome 820 and hydrophobic tails 834 that extend into the hydrophobic area 822 of the bilayer. The hydrophilic heads 828,832 form the boundaries of the bilayer that facilitate isolation of the hydrophobic area, which includes the hydrophobic active ingredient 860. With the hydrophobic area 822 isolated, the liposome 820 can be mixed into the surrounding aqueous solution 850. As indicated in FIG. 34, the liposome 820 is largely spherical in shape, although non-spherical shapes are also possible. As shown in FIG. 34, the liposome 820 and the surrounding aqueous solution 850 are contained within a cartridge 800.

Liquid mixtures that include active ingredient delivery nanoparticles in accordance with FIG. 33 or 34 include an active ingredient, an encapsulation agent, and an aqueous solution. As described herein, one contemplated active ingredient includes THC/CBD molecules, although a wide range of other active ingredients are contemplated to be deliverable to the human pulmonary system in accordance with the invention, including, but not limited to, pharmaceutical compounds, micronutrients, and nicotine. Encapsulation agents to encapsulate hydrophobic active ingredient molecules are compounds with a hydrophobic region and a hydrophilic region. It is contemplated that encapsulation agents include, but are not limited to, lipids, polymers, and surfactants. Encapsulation agents can be used singly or in combination with each other. The aqueous solution is a medium that can be selected and formulated to achieve an osmotic balance with respect to human physiology. In at least some embodiments, the aqueous solution is a 0.9% saline solution, which is understood to provide a preferred osmotic balance with human physiology of the lungs. Furthermore, a 0.9% saline solution as the aqueous medium facilitates a safer user experience, particularly when the liquid mixture is aerosolized.

With respect to polymers as encapsulation agents, it is contemplated that polymers include, but are not limited to, poly(lactic-co-glycolic) acid (PLGA), polylactic acid (PLA), polyglycolic acid (PGA), polycaprolactone (PCL), and polyhydroxybutyrate (PHB).

With respect to surfactants as encapsulation agents, it is contemplated that surfactants include, but are not limited to: high purity polyoxyethylene sorbitan monooleate (also known by its trade name, SUPER REFINED® Polysorbate 80); polyoxyethylene sorbitan monooleate; (also known by its trade name, TWEEN® Polysorbate 80); polyoxyethylene sorbitan monostearate (also known by its trade name TWEEN® Polysorbate 60); polyoxyethylene sorbitan monopalmitate (also known by its trade name TWEEN® Polysorbate 40); polyoxyethylene sorbitan monolaurate (also known by its trade name TWEEN® Polysorbate 20); lecithin; dipalmitoylphosphatidylcholine (DPPC); 1,2-distearoyl-sn-glycero-3-phosphocholine (DSPC); sorbitan monostearate (also known by its trade name SPAN 60); and sorbitan monopalmitate (also known by its trade name SPAN 40). When using one or more surfactants as an encapsulating agent, a ratio of surfactant combinations is determined by hydrophilic-lipophilic balance (HLB) values inherent to each surfactant. The combination of surfactants yields a weighted average HLB value that can be used to match the target application in order to enhance or optimize mixing of nanoparticles containing the active ingredient into the aqueous solution. For example, an HLB value measuring from approximately 8 to approximately 16 is satisfactory for oil-in-water emulsions.

In at least some embodiments, the encapsulating agent includes a high purity or high-grade surfactant, which is understood to enhance the shelf-life of the resulting mixture as well as to improve the efficacy and safety of the resulting mixture. One such high purity surfactant that can be used in the formulation is high purity polyoxyethylene sorbitan monooleate, which is also known by its trade name, SUPER REFINED® Polysorbate 80. SUPER REFINED® Polysorbate 80 is manufactured and sold by Croda International Plc of the United Kingdom.

A ratio of the surfactant relative to the active ingredient affects the size of the resulting nanoparticles (e.g., micelles and/or liposomes that contain the active ingredient). In various embodiments, it is contemplated that the surfactant-to-active-ingredient ratio can range from approximately 0.1:1 to approximately 10:1. Size of the resulting nanoparticles that contain the active ingredient affects a variety of characteristics of the final product, including pulmonary deposition of the active ingredient, absorption of the active ingredient, and the product shelf-life.

Figure 35:
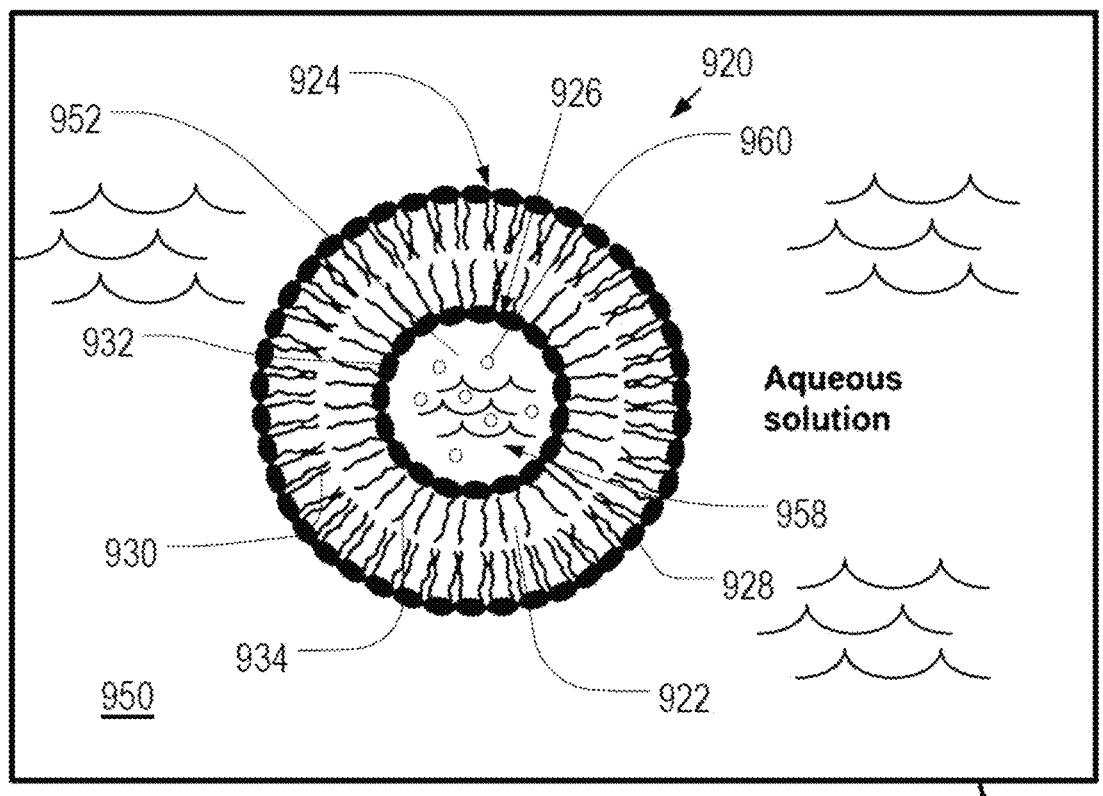
FIG. 35 is a schematic diagram of an active ingredient pulmonary delivery nanoparticle in the form of a liposome carrying an active ingredient in a hydrophilic core in accordance with one or more aspects of the invention.

In at least some embodiments, a process for producing a liquid mixture that includes active-ingredient nanocarriers in accordance with FIGS. 33-35 is accomplished using a microfluidics approach. Microfluidics involves utilizing a network of channels having very small dimensions to process the liquid mixture in order to achieve homogeneous mixture with consistently-sized nanoparticles. In one such embodiment, a microfluidizer is utilized to achieve the desired nanoparticle dispersal and uniform mixture with consistently-sized nanoparticles. During a processing step using a microfluidizer, it is contemplated that a temperature of the liquid mixture does not exceed a temperature threshold of 65° C. By not exceeding a predetermined temperature threshold, the risk of generating harmful HPHCs in the mixture via heat is reduced, thereby enhancing consumer safety. Additionally, processing the liquid mixture using a microfluidizer facilitates processing without the use of chemical solvents, which further reduces the risk of generating harmful HPHCs in the final liquid mixture. Still further, use of a microfluidics approach helps to maintain sterility in the materials used to produce the final liquid mixture, which also enhances consumer safety.

Using a microfluidics approach, the processed liquid includes nanoparticles of a uniformly small size and a low polydispersity index (PDI) value. In at least some embodiments, it is contemplated that THC/CBD nanoparticles in the final liquid mixture have an average diameter less than 1,000 nanometers or, alternatively, have a dimension that is no larger than 1,000 nanometers. It is believed that nanoparticles of this scale provide enhanced pulmonary deposition of the active ingredient into the alveolar lung region, which facilitates increased pulmonary absorption. Furthermore, nanoparticles of this scale enhance the stability of the final liquid mixture, which increases its shelf-life. Additionally, in at least some embodiments, it is contemplated that the final liquid mixture has a PDI value measuring less than 0.3. The PDI value provides a measurement of the broadness of size distribution. A low PDI value is indicative of a high level of particle size uniformity in a mixture. In accordance with contemplated embodiments of the invention, the PDI value is 0.3 or less, which is believed to indicate a liquid mixture with increased stability and enhanced shelf-life. A PDI measurement scale assigns a value of 0.0 to a population of particles where the particles have a perfectly uniform size and a value of 1.0 to a highly polydisperse population of particles with multiple size populations.

In at least some embodiments, it is contemplated that the pH of the final liquid mixture can be adjusted to accommodate a specific objective. For example, in some embodiments, a pH value of the final liquid mixture that is greater than approximately 3 and less than approximately 10 can improve the inhalation experience for the user by reducing a cough reaction. In preferred embodiments, a pH value of the final liquid mixture that is greater than approximately 5.5 and less than approximately 8, more preferably, is about 6.5, so as to match the pH of the human respiratory tract, improve consumer safety, enhance pulmonary absorption of the active ingredient, and enhance or optimize shelf-life of the liquid.

The final liquid mixture includes many THC/CBD-encapsulated nanoparticles that are uniformly suspended in an aqueous solution for downstream aerosolization by an aerosolizing device for inhalation. Such devices may include, for example, vaporizers and nebulizers.

In at least some embodiments, the encapsulated molecules are chemically bonded to other molecules in a conjugated system. Establishing a conjugated system with chemical bonds between the active ingredient molecules and other molecules facilitates more efficient encapsulation of the active ingredients via the techniques described herein. In some contemplated embodiments, then THC/CBD molecules are chemically bonded with molecules of stearic acid and/or oleic acid. Establishing a conjugated system, as described herein, is understood to enhance or optimize encapsulation of THC/CBD molecules as well as other drugs or pharmaceutical compounds.

It is contemplated that formulations and methods as described herein can be applied to hydrophobic drugs or compounds other than THC/CBD. It is further contemplated that formulations and methods as described herein can be applied to hydrophilic drugs or compounds with modifications. One such modification includes encapsulating the hydrophilic drug or compound into a hydrophilic core of a liposomal nanoparticle. Another such modification includes conjugation of the hydrophilic drug or compound to a hydrophobic molecule (such as by chemical bonding) in order to achieve an overall hydrophobic compound capable of being encapsulated in the manner as set forth in FIGS. 33 and 34.

Regarding encapsulation of a hydrophilic drug or compound into a hydrophilic core of a liposomal nanoparticle, reference is made to FIG. 35, which is a schematic diagram of an active ingredient pulmonary delivery nanoparticle in the form of a liposome 920 carrying a hydrophilic active ingredient 960 in a hydrophilic core 958 in accordance with one or more aspects of the invention. In FIG. 35, the hydrophobic component resides in a hydrophobic area 922 of the liposome 920 between a bilayer of one or more encapsulation agents. In at least some embodiments, the bilayer is a lipid-based bilayer. Molecules that form the outer layer 924 of the bilayer include hydrophilic heads 928 that are in contact with the surrounding aqueous solution 950 and hydrophobic tails 930 that extend into the hydrophobic area 922 of the bilayer. Lipid molecules that form the inner layer 926 of the bilayer include hydrophilic heads 932 that are in contact with the aqueous solution 952 at the core 958 of the liposome 920 and hydrophobic tails 934 that extend into the hydrophobic area 922 of the bilayer. The hydrophilic heads 928,932 form the barriers of the bilayer that facilitate isolation of the hydrophobic area 922. The hydrophilic active ingredient 960 is contained within the hydrophilic core 958. With the hydrophobic area 922 isolated, the liposome 920 can be mixed into the surrounding aqueous solution 950. As indicated in FIG. 35, the liposome 920 is largely spherical in shape, although non-spherical shapes are also possible. Also, the liposome 920 and the surrounding aqueous solution 950 are contained within a cartridge 800.

In at least some embodiments, it is further contemplated that the aqueous solution of the product can be buffered to mitigate pH over time. In this respect, it is contemplated that a saline solution can be converted to a phosphate buffer saline solution. Buffering the solution with the addition of a buffering agent can enhance consistency of the product, increase the shelf-life, and enhance the consumer experience when the product is aerosolized during use.

In at least some embodiments, it is further contemplated that additives can be included in the aqueous solution of the product. Contemplated additives include, but are not limited to antioxidants (such as ascorbic acid, sodium ascorbate, or others) and preservatives (such as antimicrobials). In some respects, additives can provide a safer consumer experience when the product is aerosolized during use. In other respects, additives can enhance the shelf-life of the product.

Additives can also be used to enhance or complement the user experience. For example, additives can be included to enhance or complement the smell/taste during inhalation of the aerosolized product. Additives to enhance or complement the smell/taste during inhalation include, but are not limited to, menthol and mint. Furthermore, additives can be included to enhance or complement the inhalation sensation during inhalation of the aerosolized product. An additive that enhances or complements the inhalation sensation might mimic a throat hit sensation commonly associated with nicotine inhalation or the sensation might trigger a feeling of smoothness for the consumer.

In at least some embodiments, it is further contemplated that a carrier or diluent solution is used in connection with the active ingredient to increase stability of the resulting product. Additionally, a carrier or diluent solution can enhance manufacturing process efficiency with respect to the ability to encapsulate the active ingredient when forming the nanoparticles. One contemplated carrier or diluent solution includes a medium-chain triglyceride (MCT) oil.

While many aspects and features relate to, and are described in, the context of THC/CBD delivery systems, the invention is not limited to use only in pulmonary delivery of THC/CBD, as will become apparent from the following summaries and detailed descriptions of aspects, features, and one or more embodiments of the invention.

Based on the foregoing description, it will be readily understood by those persons skilled in the art that the invention has broad utility and application. Electronic devices of the invention can be utilized to deliver liquids comprising supplements, drugs, or therapeutically effective amounts of pharmaceuticals using an aerosol having particles of a size that can easily be inhaled. The aerosol can be used, for example, by a patient within the bounds of an inhalation therapy, whereby the liquid containing a supplement, therapeutically effective pharmaceutical, or drug reaches the patient's respiratory tract upon inhalation. Desired compounds such as nicotine, flavoring, and supplements like B12, can be received by a person through inhalation without the toxic byproducts like formaldehyde—a recognized Group 1 Carcinogen for caner—that is currently being created during heating in conventional vapes. Electronic devices of the invention further can be used in the marijuana industries, but only where legal, for delivery of cannabinoids and CBD oils and the like. Moreover, many embodiments and adaptations of the invention other than those specifically described herein, as well as many variations, modifications, and equivalent arrangements, will be apparent from or reasonably suggested by the invention and the foregoing descriptions thereof, without departing from the substance or scope of the invention.

It further will be appreciated from the foregoing that at least some preferred embodiments of the invention represent a portable, orientation-agnostic vibrating mesh nebulizer. It further will be appreciated from the foregoing that at least some preferred embodiments emit an aerosol that is—sensorially speaking—equivalent to vapor, i.e., not a mist but instead that which is generated by traditional vapes, thereby providing an enjoyable consumer product for those who are accustomed to vaping.

Accordingly, while the invention has been described herein in detail in relation to one or more preferred embodiments, it is to be understood that this disclosure is only illustrative and exemplary of the invention and is made merely for the purpose of providing a full and enabling disclosure of the invention. The foregoing disclosure is not intended to be construed to limit the invention or otherwise exclude any such other embodiments, adaptations, variations, modifications or equivalent arrangements, the invention being limited only by the claims appended hereto and the equivalents thereof

What is claimed is:

1. An electronic device for producing an aerosol for inhalation by a person, comprising:
   (a) a cartridge comprising a cartridge body and a mouthpiece secured to the cartridge body in covering relation to a top of the cartridge body;
   (b) a silicone bladder containing a liquid, wherein the silicone bladder is contained within the cartridge body with a bottom of the silicone bladder being secured to a plate defining a bottom of the cartridge body and a mouth of the silicone bladder being arranged within an opening in a wall defining the top of the cartridge body;
   (c) a mesh assembly comprising a mesh material and a piezoelectric material, and located at the mouth of the silicone bladder within the opening in the wall defining the top of the cartridge body, wherein a flange of the mouth of the silicone bladder forms a seal with an underside of the mesh assembly such that the liquid does not leak from the silicone bladder, and wherein the mesh material is configured to vibrate when the piezoelectric material is actuated whereby the aerosol is produced when the mesh material contacts the liquid of the silicone bladder such that the aerosol may be inhaled through the mouthpiece secured in covering relation to the top of the cartridge body; and
   (d) a base housing comprising circuitry and a power supply for actuating the mesh assembly, wherein the cartridge is partially received within a recess of an end of the base housing and removably mounted within the recess, the plate of the cartridge body being magnetically attached to the base housing.

2. The electronic device of claim 1, wherein electrical contacts of the mesh assembly interface with electrical contacts connecting to the circuitry and power supply when the cartridge is mounted onto the end of the base housing of the electronic device.

3. The electronic device of claim 1, wherein the silicone bladder contains between about 1 ml and 3 ml of the liquid.

4. The electronic device of claim 1, wherein the mesh assembly comprises a piezo mesh disk.

5. The electronic device of claim 1, wherein the mesh assembly comprises an annular ring and wherein the mesh material is located within the area bounded by the annual ring.

6. The electronic device of claim 1, wherein the mesh material is flat.

7. The electronic device of claim 1, wherein the mesh material is dome-shaped.

8. The electronic device of claim 1, wherein the mesh material is constructed from a metal alloy.

9. The electronic device of claim 1, wherein the mesh material is produced by electroplating.

10. The electronic device of claim 1, wherein the mesh material is produced by laser cutting.

11. The electronic device of claim 1, wherein the mesh material is in the form of a mesh plate.

12. The electronic device of claim 1, wherein the cartridge is a single-use, disposable cartridge.

13. The electronic device of claim 1, wherein the liquid comprises a nanoemulsion, each of a plurality of nanoparticles of the nanoemulsion comprising an encapsulation of the substance to be delivered into the body through respiration.

14. The electronic device of claim 1, wherein a bottom end of the silicone bladder extends through an opening in the plate and mechanically anchors the silicone bladder contained within the cartridge body.

15. The electronic device of claim 1, wherein the silicone bladder is configured to receive an injection of the liquid by a syringe extending through a wall of the silicone bladder when the silicone bladder is secured to the plate and contained within the cartridge body.

16. The electronic device of claim 1, wherein the silicone bladder has a hardness of about 40 durometer.

17. The electronic device of claim 1, wherein the plate of the cartridge body is magnetically attached by magnets to a main body chassis of the base housing.

* * * * *